(12) United States Patent
Gordon-Kamm et al.

(10) Patent No.: US 10,947,550 B2
(45) Date of Patent: Mar. 16, 2021

(54) AP2 DOMAIN TRANSCRIPTION FACTOR ODP2 (OVULE DEVELOPMENT PROTEIN 2) AND METHODS OF USE

(71) Applicant: PIONEER HI-BRED INTERNATIONAL, INC., Johnston, IA (US)

(72) Inventors: William J Gordon-Kamm, Urbandale, IA (US); Timothy G Helentjaris, Tucson, AZ (US); Keith S Lowe, Johnston, IA (US); Bo Shen, Johnston, IA (US); Mitchell C Tarczynski, West Des Moines, IA (US); Peizhong Zheng, Carmel, IN (US)

(73) Assignee: PIONEER HI-BRED INTERNATIONAL, INC.

( * ) Notice: Subject to any disclaimer, the term of this patent is extended or adjusted under 35 U.S.C. 154(b) by 14 days.

(21) Appl. No.: 16/142,766

(22) Filed: Sep. 26, 2018

(65) Prior Publication Data

US 2019/0017061 A1   Jan. 17, 2019

Related U.S. Application Data

(60) Continuation of application No. 15/131,181, filed on Apr. 18, 2016, now Pat. No. 10,113,175, which is a division of application No. 13/790,641, filed on Mar. 8, 2013, now Pat. No. 9,340,796, which is a continuation of application No. 12/503,482, filed on Jul. 15, 2009, now Pat. No. 8,420,893, which is a continuation of application No. 11/045,802, filed on Jan. 28, 2005, now Pat. No. 7,578,529.

(60) Provisional application No. 60/541,122, filed on Feb. 2, 2004.

(51) Int. Cl.
   C12N 15/82     (2006.01)
   A01H 1/08      (2006.01)
   C07K 14/415    (2006.01)

(52) U.S. Cl.
   CPC ........... *C12N 15/8243* (2013.01); *A01H 1/08* (2013.01); *C07K 14/415* (2013.01); *C12N 15/8201* (2013.01); *C12N 15/8205* (2013.01); *C12N 15/8209* (2013.01); *C12N 15/8223* (2013.01); *C12N 15/8231* (2013.01); *C12N 15/8233* (2013.01); *C12N 15/8245* (2013.01); *C12N 15/8247* (2013.01); *C12N 15/8261* (2013.01); *C12N 15/8287* (2013.01); *Y02A 40/146* (2018.01)

(58) Field of Classification Search
   None
   See application file for complete search history.

(56) References Cited

U.S. PATENT DOCUMENTS

| | | |
|---|---|---|
| 6,093,874 A | 7/2000 | Jofuku et al. |
| 6,512,165 B1 | 1/2003 | Ross et al. |
| 7,151,170 B1 | 12/2006 | Boutilier et al. |
| 7,256,322 B2 | 8/2007 | Lowe et al. |
| 7,348,468 B1 | 3/2008 | Cahoon et al. |
| 7,414,172 B2 | 8/2008 | Pages et al. |
| 7,579,529 B2 | 8/2009 | Gordon-Kamm et al. |
| 7,700,829 B2 | 4/2010 | Zuo et al. |
| 7,816,580 B2 | 10/2010 | Zuo et al. |
| 8,420,893 B2 | 4/2013 | Gordon-Kamm |
| 2003/0049835 A1 | 3/2003 | Helliwell et al. |
| 2003/0082813 A1 | 5/2003 | Zuo et al. |
| 2003/0135889 A1 | 7/2003 | Ross et al. |
| 2004/0166563 A1 | 8/2004 | Lowe et al. |
| 2004/0247620 A1 | 12/2004 | Julien |
| 2005/0044595 A1 | 2/2005 | Arias et al. |
| 2007/0271628 A1 | 11/2007 | Lowe et al. |
| 2011/0016751 A1 | 7/2011 | Gordon-Kamm et al. |
| 2011/0165679 A1 | 7/2011 | Gordon-Kamm et al. |

FOREIGN PATENT DOCUMENTS

| | | |
|---|---|---|
| EP | 1 033 405 A2 | 9/2000 |
| EP | 1 054 891 A1 | 11/2000 |
| EP | 1 057 891 A | 12/2000 |
| EP | 1 094 112 A2 | 4/2001 |
| EP | 1 185 656 A1 | 3/2002 |
| WO | 1998/007842 A | 2/1998 |
| WO | 1999/015178 | 4/1999 |
| WO | 1999/021574 | 4/1999 |
| WO | 1999/041974 | 8/1999 |
| WO | 2000/040694 A | 7/2000 |
| WO | 2000/075330 | 12/2000 |
| WO | 2001/023575 A2 | 4/2001 |

(Continued)

OTHER PUBLICATIONS

Bowie et al (1990, "Deciphering the Message in Protein Sequences: Tolerance to Amino Acid Substitutions", Science 247:1306-1310).*
McConnell et al, (2001, "Radial Patterning of *Arabidopsis* Shoots By Class III HD-ZIP and KANADI Genes", Nature 411 (6838):709-713).*
Kano-Murakami et al (1993, "A Rice Homeotic Gene, OSH1, Causes Unusual Phenotypes in Transgenic Tobacco", FEBS 334:365-368).*

(Continued)

*Primary Examiner* — Stuart F Baum

(57) ABSTRACT

Methods and compositions for modulating plant development are provided. Nucleotide sequences and amino acid sequences encoding Ovule Development Protein 2 (ODP2) proteins are provided. The sequences can be used in a variety of methods including modulating development, developmental pathways, altering oil content in a plant, increasing transformation efficiencies, modulating stress tolerance, and modulating the regenerative capacity of a plant. Transformed plants, plant cells, tissues, and seed are also provided.

16 Claims, 6 Drawing Sheets

Specification includes a Sequence Listing.

(56) References Cited

FOREIGN PATENT DOCUMENTS

| | | |
|---|---|---|
| WO | 2002/059294 A1 | 8/2002 |
| WO | 2002/097059 A2 | 12/2002 |
| WO | 2003/001902 A2 | 1/2003 |
| WO | 2003/002751 A2 | 1/2003 |
| WO | 2003/037072 A2 | 5/2003 |
| WO | 2005/063990 A2 | 7/2005 |
| WO | 2009/132057 A1 | 10/2009 |

OTHER PUBLICATIONS

Boutilier, Kim, et al.: "Ectopic Expression of Baby Boom Triggers a Conversion from Vegetative to Embryonic Growth", The Plant Cell, Aug. 2002 (Aug. 2002), vol. 14, No. 8, pp. 1737-1749.
Bowie, J. U., et al.: "Deciphering the Message in Protein Sequences: Tolerance to Amino Acid Substitutions", Science, 1990, vol. 247, pp. 1306-1310.
Feng, Q., et al.: "Sequence and Analysis of Rice Chromosome 4", Nature, 2002, vol. 420, pp. 316-320.
GenBank Report for Accession No. AAD30633, Direct Submission on Oct. 30, 2002.
GenBank Report for Accession No. AAL47205, Direct Submission on May 31, 2002.
GenBank Report for Accession No. AAM33800, Direct Submission on Oct. 10, 2002.
GenBank Report for Accession No. AAM33801, Direct Submission on Oct. 10, 2002.
GenBank Report for Accession No. AAM33803, Direct Submission on Oct. 10, 2002.
GenBank Report for Accession No. AY062108, Direct Submission on Oct. 31, 2002.
GenBank Report for Accession No. AY062180: "Oryza sativa ovule development aintegumenta-like protein BNM3 (BNM3) gene, complete cds", Jun. 3, 2002 (Jun. 3, 2002).
GenBank Report for Accession No. AY062180, Direct Submission on Oct. 31, 2001.
GenBank Report for Accession No. BAB02492, Direct Submission on Feb. 14, 2004.
GenBank Report for Accession No. BAB89946, Direct Submission on Aug. 31, 2004.
GenBank Report for Accession No. CAE02944, Direct Submission on Apr. 16, 2005.
GenBank Report for Accession No. CAE05555, Direct Submission on Apr. 16, 2015.
GenBank Report for Accession No. CC603221, 2003.
GenBank Report for Accession No. CC667986: "OGUHN41TV ZM_0.7_1.5_KB *Zea mays* genomic clone ZMMBMa0441H10, genomic survey sequence", Jun. 20, 2003 (Jun. 20, 2003).
GenBank Report for Accession No. CL960366: "OsIFCC004330 *Oryza sativa* Express Library *Oryza sativa* (indica cultivar-group) genomic, genomic survey sequence", Sep. 22, 2004 (Sep. 22, 2004).
GenBank Report for Accession No. F96549, Direct Submission on Mar. 31, 2001.
GenBank Report for Accession No. NP175530, Direct Submission on Feb. 23, 2005.
GenBank Report for Accession No. NP197245, Direct Submission on Feb. 23, 2005.
Gidoni, D., et al.: "Embryonal recombination and germline inheritance of recombined FRT loci mediated by constitutively expressed FLP in tobacco", Euphytica, 2001, vol. 121, pp. 145-156.
Huang, X. Q., et al.: "High-frequency plant regeneration through callus initiation from mature embryos of maize (*Zea Mays* L)", Plant Cell Rep, 2004, vol. 22, pp. 793-800.
Invitrogen Corporation, "Gateway pDONR Vectors", User Manual, Version E, 2007, retrieved from http://wolfson.huji.ac.il/expression/gatway_pdonr_vectors_pdf, XP002627486.
Kamiya, N., et al.: "Isolation and Characterization of Rice WUSCHEL-type Homeobox Gene that is specifically Expressed in the Central Cells of a Quiescent Center in the Root Apical Meristem", The Plant Journal, 2003, vol. 35, pp. 429-441.
Kizis, Dimosthenis, et al.: "Role of AP2/EREBP transcription factors in gene regulation during abiotic stress", FEBS Letters, Jun. 8, 2001 (Jun. 8, 2001), vol. 498, No. 2-3, pp. 187-189.
Marsch-Martinez, N., et al.: "Bolita, an *Arabidopsis* AP2/ERF-Like Transcription Factor that Affects Cell Expansion and Proliferation/Differentiation Pathway", Plant Molecular Biology, 2006, vol. 62, pp. 825-843.
Mayer, K., et al.: "Role of WUSCHEL in Regulating Stem Cell Fate in the *Arabidopsis* Shoot Meristem", CELL, 1998, vol. 95, pp. 805-815.
McConnell, J. R., et al.: "Role of PHABULOSA and PHAVOLUTA in determining Radial Patterning in Shoots", Nature, 2001, vol. 411, pp. 709-713.
Mizukami, Yukiko, et al.: "Plant organ size control: Aintegumenta regulates growth and cell numbers during organogenesis", PNAS Proceedings of the National Academy of Sciences of USA, National Academy of SICENCT, Jan. 18, 2000 (Jan. 18, 2000) vol. 97, No. 2, pp. 942-947.
Nardmann, J., et al.: "The Shoot Stem Cell Niche in Angiosperms: Expression patters of WUS Orthologues in Rice and Maize Imply Major Modification in the Course of Mono- and Dicot Evolution", Mol. Viol. Evol., 2006, vol. 23, No. 12, pp. 2492-2504.
Ouakfaoui, S., et al.: "Control of Somatic Embryogenesis and Embryo Development by AP2 Transcription Factors", Plant Molecular Biology, 2010, Published Online Aug. 27, 2010 (with supplementary materials).
Riechmann, Jose Luis, et al.: "The AP2EREBP Family of Plant Transcription Factors", Biological Chemistry, Jun. 6 (Jun. 1998), vol. 379, pp. 633-646.
Sasakl, T., et al.: "The Genome Sequence and Structure of Rice Chromosome 1", Nature, 2002, vol. 420, pp. 312-316.
Sato, S., et al.: "Structural Analysis of *Arabidopsis Thaliana* Chromosome 3. I. Sequence Features of the Regions of 4,504,864 by Covered by Sixty P1 and TAC Clones", DNA Research, 2000, vol. 7, pp. 131-135.
Srinivasan, C., et al.: "Heterologous expression of the Baby Boom AP2/ERF transcription factor enhances the regeneration capacity of tobacco (*Nicotiana tabacum* L.)", Planta, 2007, vol. 225, pp. 341-351.
Theologis, A., et al.: "Sequence and Analysis of Chromosome 1 of the Plant *Arabidopsis Thaliana*", Nature, 2000, vol. 408, pp. 816-820.
Topfer, R., et al.: "Uptake and Transient Expression of Chimeric Genes in Seed-Derived Embryos", The Plant Cell, 1989, vol. 1, pp. 133-139.
Wang, Andrew S., "Callus induction and plant generation from maize mature embryos", Plant Cell Reports, 1987, vol. 6, pp. 360-362.
U.S. Appl. No. 61/291,257, filed Dec. 30, 2009.
U.S. Appl. No. 12/982,180, filed Dec. 30, 2010.
U.S. Appl. No. 14/087,775, filed Nov. 22, 2013.
International Search Report and Written Opinion, International Application No. PCT/US2005/003135 dated Nov. 10, 2005.
International Search Report and Written Opinion, International Application No. PCT/US2010/062531 dated Sep. 5, 2011.

* cited by examiner

```
                         1                                                  50
         ZM-ODP2    (1)  MATVNNWLAFSLSPQELPPSQTTDSTLISAAT--------ADHVSGDVCFN
   OsAnt(BAB89946)  (1)  MATMNNWLAFSLSPQDQLPPSQTNSTLISAAAT--TTTAGDSSTGDVCFN
   OSBNM(AAL47205)  (1)  MATMNNWLAFSLSPQDQLPPSQTNSTFISAAAT--TTTAGDSSTGDVCFN
   OSODP(CAE05555)  (1)  MASADNWLGFSLSGQGNPQHHQNGSFSAAGDA-------AIDISGSGDFYG
   AtODP(NP_197245) (1)  MNSMNNWLGFSLSPHDQNHHRTDVDSSTTRTA--------VDVAGGYCFDL
   AtBBM(AAM33803)  (1)  MNSMNNWLGFSLSPHDQNHHRTDVDSSTTRTA--------VDVAGGYCFDL
   BnBBM1(AAM33800) (1)  --MNNNWLGFSLSPYEQNHHRKDVYSSTTTTV--------VDVAGEYCYDP
   BnBBM2(AAM33801) (1)  --MNNNWLGFSLSPYEQNHHRKDVCSSTTTTA--------VDVAGEYCYDP
   AtODP(NP_175530) (1)  -MNSNNWLAFPLSPTHSSLPPHIHSSQNSHFNLGLVNDNIDNPFQNQGWN
   AtODP(BAB02492)  (1)  -----------------------------------MDNPFQTQEWN
   AtODP(AAD30633)  (1)  ----------------------------------------------
        Consensus  (1)  M S NNWLGFSLSP DQ      S   S   A           VD A      F 51                                                 100
         ZM-ODP2   (44)  IPQDWSMRGSELSALVAEPKLEDFLGGISFS-EQHHKANCNMIPSTSSTV
   OsAnt(BAB89946) (49)  IPQDWSMRGSELSALVAEPKLEDFLGGISFSEQQHHGGKGGVIPSSAAA
   OSBNM(AAL47205) (49)  IP-------------------------QAHPS-----------
   OSODP(CAE05555) (45)  LPTPDAHHIGMAGEDAPYGVMDAFNRGTHETQDWAMRGLDYGGGSSDLSM
   AtODP(NP_197245)(44)  AAPSDESSAVQTSFLSPFGVTLEAFTRDN---NSHSRDWDINGGACNNIN
   AtBBM(AAM33803) (44)  AAPSDESSAVQTSFLSPFGVTLEAFTRDN---NSHSRDWDINGGACNTLT
   BnBBM1(AAM33800)(42)  TAASDESSAIQTSFPSPFGVVVDAFTRDN----NSHSRDWDINGCACNNIH
   BnBBM2(AAM33801)(42)  TAASDESSAIQTSFPSPFGVVLDAFTRDN---NSHSRDWDINGSACNNIH
   AtODP(NP_175530)(50)  MINPHGGGGE----GGEVPKVADFLGVS----KSGDHHTDHNLVPYNDIH
   AtODP(BAB02492) (12)  MINPHGGGGDE---GGEVPKVADFLGVS----KPDENQS-------NHLV
   AtODP(AAD30633) (1)   MINPHGGGGE----GGEVPKVADFLGVS----KSGDHHTDHNLVPYNDIH
        Consensus (51)  I        G    S    V DF          NSH R  D N    A N I 101                                                150
         ZM-ODP2   (93)  CYASSGASTGYHHQLYHQPTSSALHFADSVMVASSAGVHDGGAMLSAAAA
   OsAnt(BAB89946) (99)  CYASSGSSV---GYLYPPPSSSLQFADSVMVATSSPVVAHDGVSGGGMV
   OSBNM(AAL47205) (56)  ----------------------------------------------
   OSODP(CAE05555) (95)  LVGSSGGGRRTVAGDGVGEAPKLENFLDGNSFSDVHGQAAGGYLYSGSAV
   AtODP(NP_197245)(91)  NNEQNG------------P--KLENFLGRTTTIYNTNETVVDGNG------
   AtBBM(AAM33803) (91)  NNEQNG------------P--KLENFLGRTTTIYNTNETVVDGNG-----
   BnBBM1(AAM33800)(89)  NDEQDG------------P--KLENFLGRTTTIYNTNENVGDGSGS----
   BnBBM2(AAM33801)(89)  NDEQDG------------P--KLENFLGRTTTIYNTNENVGDIDGS-----
   AtODP(NP_175530)(92)  QTNAS------------------DYYFQTNSLLP-----------
   AtODP(BAB02492) (48)  AYNDS------------------DYYFHTNSLMPS---V--------
   AtODP(AAD30633) (43)  QTNAS------------------DYYFQTNSLLP-----------
        Consensus (101) N   SG              P     ENF   S   I 151                                                200
         ZM-ODP2  (143)  NGVA--GAASANGGGIGLSMIKNWLRSQPAPMQPRVAAAEGAQGLSLSMN
   OsAnt(BAB89946)(146)  SAAA--AAAASGNGGIGLSMIKNWLRSQPAPQP----------AQALSLSMN
   OSBNM(AAL47205) (56)  -------TPAIGNGGIGLSMIKNWLRSQPAPQP---------AQALSLSMN
   OSODP(CAE05555)(145)  GGAGGYSNGGCGGGTIELSMIKTWLRSNQSQQQP-------SPPQHADQG
   AtODP(NP_197245)(122) ---DCGGGDGGGGGSLGLSMIKTWLSNHSVANANH------------
   AtBBM(AAM33803)(122)  ---DCGGGDGGGGGSLGLSMIKTWLSNHSVANANH------------
   BnBBM1(AAM33800)(121) ---GCYGGGDGGGGSLGLSMIKTWLRNQPVDNVDN-----------
   BnBBM2(AAM33801)(121) ---GCYGGGDGGGGSLGLSMIKTWLRNQPVDNVDN-----------
   AtODP(NP_175530)(108) ----------------TVVTCASNAPNN-----------
   AtODP(BAB02492) (66)  -----------QSNDVVVAACDSNTPNNSSY--------
   AtODP(AAD30633) (59)  ----------------TVVTCASNAPNN-----------
        Consensus (151)         GG    GGG IGLSMIKTWLRNQP       N
```

FIG. 1A

```
                             201                                                  250
         ZM-ODP2       (191) MAGTTQGAAG--MPLLAGERAR-----APESVSTSAQGGAVVVTAPKEDS
    OsAnt(BAB89946)    (186) MAGTTTAQGGGAMALLAGAGERGRTTPASESLSTSAHGATTATMAGGRKE
    OSBNM(AAL47205)    ( 91) MAGTTTAQGGGAMALLAGAGERGRTTPASESLSTSAHGATTATMAGGRKE
    OSODP(CAE05555)    (188) MSTDASASSYACSDVLVGSCGGGG---AGGTASSHGQGLALSMSTGSVAA
    AtODP(NP_197245)   (154) ------------------------------QDNGNGARGLSLSMNSSTS-D
    AtBBM(AAM33803)    (154) ------------------------------QDNGNGARGLSLSMNSSTS-D
    BnBBM1(AAM33800)   (153) ------------------------------QENGNAAKGLSLSMNSSTSCD
    BnBBM2(AAM33801)   (153) ------------------------------QENGNGAKGLSLSMNSSTSCD
    AtODP(NP_175530)   (120) --------------------------YELQESAHNLQSLTLSMGSTGA-A
    AtODP(BAB02492)    ( 86) --------------------------HELQESAHNLQSLTLSMGTT----
    AtODP(AAD30633)    ( 71) --------------------------YELQESAHNLQSLTLSMGSTGA-A
         Consensus     (201)                            QE S  A GLTLSM SS S D 251                                                  300
         ZM-ODP2       (234) G----GSGVAGALVAVSTDTGGS-----GGASADNTARKTVDTFGQRTSIYR
    OsAnt(BAB89946)    (236) INEEGSGSAGAVVAVGSESGGSGAVVEAGAAAAAARKSVDTFGQRTSIYR
    OSBNM(AAL47205)    (141) INEEGSGSAGAVVAVGSESGGSGAVVEAGAAAAAARKSVDTFGQRTSIYR
    OSODP(CAE05555)    (235) AG--GGGAVVAAESSSSENKRVDSP-GGAVDGAVPRKSIDTFGQRTSIYR
    AtODP(NP_197245)   (174) SNNYNNNDDVVQEKTIVDVVET---------TPK--KTIESFGQRTSIYR
    AtBBM(AAM33803)    (174) SNNYNNNDDVVQEKTIVDVVET---------TPK--KTIESFGQRTSIYR
    BnBBM1(AAM33800)   (174) NNNDSNNNVVAQGKTIDDSVEA---------TPK--KTIESFGQRTSIYR
    BnBBM2(AAM33801)   (174) NNNYSSNNLVAQGKTIDDSVEA---------TPK--KTIESFGQRTSIYR
    AtODP(NP_175530)   (143) AAEVATVKASPAETSADNSSSTTNTSGGAIVEATPRRTLETFGQRTSIYR
    AtODP(BAB02492)    (106) AGNNVVDKASPSETTGDNAS--G-GALAVVETATPRRALDTFGQRTSIYR
    AtODP(AAD30633)    ( 94) AAEVATVKASPAETSADNSSSTTNTSGGAIVEATPRRTLETFGQRTSIYR
         Consensus     (251) AN  GS  A  A E T  DS T      GA   A  RKTIETFGQRTSIYR 301                                                  350
         ZM-ODP2       (277) GVTRHRWTGRYEAHLWDNSCRREGQTRKGRQVYLGGYDKEEKAARAYDLA
    OsAnt(BAB89946)    (286) GVTRHRWTGRYEAHLWDNSCRREGQTRKGR---QGGYDKEEKAAPAYDLA
    OSBNM(AAL47205)    (191) GVTRHRWTGRYEAHLWDNSCRREGQTRKGR---QGGYDKEEKAARAYDLA
    OSODP(CAE05555)    (282) GVTRHRWTGRYEAHLWDNSCRREGQSRKGR---QGGYDKEDKAARAYDLA
    AtODP(NP_197245)   (213) GVTRHRWTGRYEAHLWDNSCKREGQTRKGR---QGGYDKEEKAAPAYDLA
    AtBBM(AAM33803)    (213) GVTRHRWTGRYEAHLWDNSCKREGQTRKGRQVYLGGYDKEEKAARAYDLA
    BnBBM1(AAM33800)   (213) GVTRHRWTGRYEAHLWDNSCKREGQTRKGRQVYLGGYDKEEKAARAYDLA
    BnBBM2(AAM33801)   (213) GVTRHRWTGRYEAHLWDNSCKREGQTRKGRQVYLGGYDKEEKAARAYDLA
    AtODP(NP_175530)   (193) GVTRHRWTGRYEAHLWDNSCRREGQSRKGR---QGGYDKEEKAARAYDLA
    AtODP(BAB02492)    (153) GVTRHRWTGRYEAHLWDNSCRREGQSRKGR---QGGYDKEDKAARSYDLA
    AtODP(AAD30633)    (144) GVTRHRWTGRYEAHLWDNSCRREGQSRKGR---QGGYDKEEKAARAYDLA
         Consensus     (301) GVTRHRWTGRYEAHLWDNSCRREGQTRKGR   QGGYDKEEKAARAYDLA 351                                                  400
         ZM-ODP2       (327) ALKYWGATTTTNFPVSNYEKELEDMKHMTRQEFVASLRRKSSGFSRGASI
    OsAnt(BAB89946)    (333) ALKYWGPTTTNFPVNNYEKELEEMKHMTRQEFVASLRRKSSGFSRGASI
    OSBNM(AAL47205)    (238) ALKYWGPTTTNFPVNNYEKELEEMKHMTRQEFVASLRRKSSGFSRGASI
    OSODP(CAE05555)    (329) ALKYWGTTTTTNFPMSNYEKELEEMKHMTRQEYIAHLRRNSSGFSRGASK
    AtODP(NP_197245)   (260) ALKYWGPTTTTNFPLSEYEKEVEEMKHMTRQEYVASLRRKSSGFSRGASI
    AtBBM(AAM33803)    (263) ALKYWGPTTTTNFPPLSEYEKEVEEMKHMTRQEYVASLRRKSSGFSRGASI
    BnBBM1(AAM33800)   (263) ALKYWGTTTTTNFPPMSEYEKEVEEMKHMTRQEYVASLRRKSSGFSRGASI
    BnBBM2(AAM33801)   (263) ALKYWGTTTTTNFPPMSEYEKEIEEMKHMTRQEYVASLRRKSSGFSRGASI
    AtODP(NP_175530)   (240) ALKYWGPSTTNFPITNYEKEVEEMKNMTRQEFVASIRRKSSGFSRGASM
    AtODP(BAB02492)    (200) ALKYWGPSTTNFPITNYEKEVEEMKHMTRQEFVAAIRPKSSGFSRGASM
    AtODP(AAD30633)    (191) ALKYWGPSTTNFPITNYEKEVEEMKNMTRQEFVASIRRKSSGFSRGASM
         Consensus     (351) ALKYWGPTTTTNFPISNYEKEVEEMKHMTRQEFVASLRRKSSGFSRGASI
```

FIG. 1B

```
                              551                                              450
         ZM-ODP2       (377)  YRGVTRHHQHGRWQARIGRVAGNKDLYLGTFSTQEEAAEAYDIAAIKFRG
  OsAnt(BAB89946)      (383)  YRGVTRHHQHGRWQARIGRVAGNKDLYLGTFSTQEEAAEAYDIAAIKFRG
  OSBNM(AAL47205)      (288)  YRGVTRHHQHGRWQARIGRVAGNKDLYLGTFSTQEEAAEAYDIAAIKFRG
  OSODP(CAE05555)      (379)  YRGVTRHHQHGRWQARIGRVAGNKDIYLGTFSTEEEAAEAYDIAAIKFRG
  AtODP(NP_197245)     (310)  YRGVTRHHQHGRWQARIGRVAGNKDLYLGTFGTQEEAAEAYDIAAIKFRG
  AtBBM(AAM33803)      (313)  YRGVTRHHQHGRWQARIGRVAGNKDLYLGTFGTQEEAAEAYDIAAIKFRG
  BnBBM1(AAM33800)     (313)  YRGVTRHHQHGRWQARIGRVAGNKDLYLGTFGTQEEAAEAYDIAAIKFRG
  BnBBM2(AAM33801)     (313)  YRGVTRHHQHGRWQARIGRVAGNKDLYLGTFGTQEEAAEAYDIAAIKFRG
  AtODP(NP_175530)     (290)  YRGVTRHHQHGRWQARIGRVAGNKDLYLGTFSTEEEAAEAYDIAAIKFRG
  AtODP(BAB02492)      (250)  YRGVTRHHQHGRWQARIGRVAGNKDLYLGTFSTEEEAAEAYDIAAIKFRG
  AtODP(AAD30633)      (241)  YRGVTRHHQHGRWQARIGRVAGNKDLYLGTFSTEEEAAEAYDIAAIKFRG
        Consensus      (401)  YRGVTRHHQHGRWQARIGRVAGNKDLYLGTFSTQEEAAEAYDIAAIKFRG 551                                              500
         ZM-ODP2       (427)  LNAVTNFDMSRYDVKSILDSSALPIG-SAAKRLKEAEAAASAQHHHAGVV
  OsAnt(BAB89946)      (433)  LNAVTNFDMSRYDVKSILDSAALPVG-TAAKRLKDAEAAA----------
  OSBNM(AAL47205)      (338)  LNAVTNFDMSRYDVKSILDSAALPVG-TAAKRLKDAEAAA----------
  OSODP(CAE05555)      (429)  LNAVTNFDMSRYDVKSILDSSTLPVG-GAARRLKEAEVAA--------A-
  AtODP(NP_197245)     (360)  LSAVTNFDMNRYNVKAILESPSLPIG-SSAKRLKDVNNPVP---------
  AtBBM(AAM33803)      (363)  LSAVTNFDMNRYNVKAILESPSLPIG-SSAKRLKDVNNPVP---------
  BnBBM1(AAM33800)     (363)  LTAVTNFDMNRYNVKAILESPSLPIG-SAAKRLKEANRPVPS--------
  BnBBM2(AAM33801)     (363)  LTAVTNFDMNRYNVKAILESPSLPIG-SAAKRLKEANRPVPS--------
  AtODP(NP_175530)     (340)  LNAVTNFEINRYDVKAILESNTLPIGGGAAKRLKEAQALESSRKR-----
  AtODP(BAB02492)      (300)  LNAVTNFEINRYDVKAILESSTLPIGGGAAKRLKEAQALESSRKRE----
  AtODP(AAD30633)      (291)  LNAVTNFEINRYDVKAILESNTLPIGGGAAKRLKEAQALESSRKR-----
        Consensus      (451)  LNAVTNFDMNRYDVKAILES SLPIG SAAKRLKEANA     S 551                                              550
         ZM-ODP2       (476)  SYDVGRIASQLGDGGALA-AAYGAHYHG-AAWPTIAFQPGAAS----T
  OsAnt(BAB89946)      (472)  AYDVGRIASHLGGDGAYA-AHYGHHHHSAAAAWPTIAFQAAAAPPPHAA
  OSBNM(AAL47205)      (377)  AYDVGRIASHLGGDGAYA-AHYGHHHHSAAAAWPTIAFQAAAAPPPHAA
  OSODP(CAE05555)      (469)  AAGGGVIVSHLADGG---------VGGYYYG----CGPTIAFGGGGQQPAPLA
  AtODP(NP_197245)     (400)  ---AMMISNNVSESAN------NVSGWQNTAFQHHQGMDLSLLQQQQERYV
  AtBBM(AAM33803)      (403)  ---AMMISNNVSESAN------NVSGWQNTAFQHHQGMDLSLLQQQQERYV
  BnBBM1(AAM33800)     (404)  ---MMMISNNVSESEN------SASGWQNAAVQHHQGVDLSLLHQHQERYN
  BnBBM2(AAM33801)     (404)  ---MMMISNNVSESEN------NASGWQNAAVQHHQGVDLSLLQQHQERYN
  AtODP(NP_175530)     (385)  --EEMIALGSNFHQYGAASGSSSVASSSRLQLQPYPLSIQQPFEHLHHHQP
  AtODP(BAB02492)      (346)  --AEMIALGSSFQYGGGSS-TGSGSTSSRLQLQPYPLSIQQPLEPFLSLQN
  AtODP(AAD30633)      (336)  --EEMIALGSNFHQYGAASGSSSVASSSRLQLQPYPLSIQQPFEHLHHHQP
        Consensus      (501)      DMM ISSNL E GA A      SG    A Q HP I  Q 551                                              600
         ZM-ODP2       (518)  GLYHPYAQQPMRGGGWCKQEQDHAVIAAAHSLQDLHHLNLG--AAGAHDF
  OsAnt(BAB89946)      (520)  GLYHPYAQPLR----GWCKQEQDHAVIAAAHSLQDLHHLNLG--AAAAAHD
  OSBNM(AAL47205)      (425)  GLYHPYAQPLR---GWCKQEQDHAVIAAGHSLQDLHHLNLG--AAAAAHD
  OSODP(CAE05555)      (509)  VHYPSYGQASGT----WCKPE-QDAVIAAGHCATDLQHLHLGSGGAAATHN
  AtODP(NP_197245)     (442)  GYYN-GGNLST------------ESTRVCFKQEEEQQHFLRN--SPSHMTN
  AtBBM(AAM33803)      (445)  GYYN-GGNLST------------ESTRVCFKQEEEQQHFLRN--SPSHMTN
  BnBBM1(AAM33800)     (446)  GYYYNGGNLST------------ESARACFKQEDDQHHFLSN--TQSLMTN
  BnBBM2(AAM33801)     (446)  GYYYNGGNLSS------------ESARACFKQEDDQHHFLSN--TQSLMTN
  AtODP(NP_175530)     (434)  LLTLQNNN------------DISQYHDSFSYIQTQLHLHQQ-QTNNYLQ
  AtODP(BAB02492)      (394)  NDISHYNNNA---------HDSSSFNHHSYIQTQLHLHQQ-TNNYLQQ
  AtODP(AAD30633)      (385)  LLTLQNNN------------DISQYHDSFSYIQTQLHLHQQ-QTNNYLQ
        Consensus      (551)  G Y  GN              S   AAF IQDQ HL N     S     N
```

FIG. 1C

```
                           601                                                 650
         ZM-ODP2    (566)  FSAGQQAAAAAMHGLGSIDSASLEHSTGSNSVVYNGGVGDSNGASAVGGS
    OsAnt(BAB89946) (565)  FFS---QAMQQQHGLGSIDNASLEHSTGSNSVVYNGDNG--------GGG
    OSBNM(AAL47205) (470)  FFS---QAMQQQHGLGSIDNASLEHSTGSNSVVYNGDNG--------GGG
   OSODP(CAE05555)  (554)  FFQ-----QPASS------------------SAVYGNGGG--------GG
   AtODP(NP_197245) (478)  VDHHS--------------------STSDDSVTVCGNVVS-------YGG
    AtBBM(AAM33803) (481)  VDHHS--------------------STSDDSVTVCGNVVS-------YGG
    BnBBM1(AAM33800)(483)  IDHQS--------------------SVSDDSVTVCGNVVG-------YGG
    BnBBM2(AAM33801)(483)  IDHQS--------------------SVSDDSVTVCGNVVG-------YGG
   AtODP(NP_175530) (470)  SSS-----------------------HTSQLYNAYLQS-N------PGL
    AtODP(BAB02492) (433)  QSSQ----------------------NSQLYNAYLHS-N-----PAL
    AtODP(AAD30633) (421)  SSS-----------------------HTSQLYNAYLQS-N------PGL
         Consensus  (601)  S                         S       SVVYNG V          GG 651                                                 700
         ZM-ODP2    (616)  GGGYMMPMSAAGATTTSAMVSHEQVHARAYDEAKQAAQMGYESYLVNAEN
    OsAnt(BAB89946) (604)  GGYIMAPMSAVSATATAVASSHDHG------GDGGKQVQMGYDSYLVGADA
    OSBNM(AAL47205) (509)  GGYIMAPMSAVSATATAVASSHDHG------GDGGKQVQMGYDSYLVGADA
   OSODP(CAE05555)  (573)  GNAFMMPMGAVVAAADHGGQSSAYGG----GDESGRLVVGYDGVVDPYAA
   AtODP(NP_197245) (501)  YQGFAIPVGTSVNYDPFTAAEIAYN------------AR-NHYYYAQHQQ
    AtBBM(AAM33803) (504)  YQGFAIPVGTSVNYDPFTAAEIAYN------------AR-NHYYYAQHQQ
    BnBBM1(AAM33800)(506)  YQGFAAPV-----NCDAYAASEFDYN------------AR-NHYYFAQQQQ
    BnBBM2(AAM33801)(506)  YQGFAAPV-----NCDAYAASEFDYN------------AR-NHYYFAQQQQ
   AtODP(NP_175530) (489)  LHGFVS-----DNNNTSG------------FLGNNGIGIGSSSTVGSSAE
    AtODP(BAB02492) (453)  LHGLVSTS-IVDNNNNNGGSSSGSYNTAA---FLGNHGIGIGSSSTVGS---T
    AtODP(AAD30633) (440)  LHGFVS-----DNNNTSG------------FLGNNGIGIGSSSTVGSSAE
         Consensus  (651)       GFMAPM     N    GAS     Y         G   IAIG  SYVA 701                                             745
         ZM-ODP2    (666)  NGGGRMSAWGTVVSAAAAAASSNDNMAADVGHGGAQLFSVWNDT
    OsAnt(BAB89946) (649)  YGGGGAGRMPSWAMTPASAPAATSSSDMTGVCHG-AQLFSVWNDT
    OSBNM(AAL47205) (554)  YGGGGAGRMPSWAMTPASAPAATSSSDMTGVCHG-AQLFSVWNDT
   OSODP(CAE05555)  (619)  MRSAYELSQGSSSSSVSVAKAANGYPDNWSSPFNGMG--------
   AtODP(NP_197245) (538)  QQQIQQSPGGDFPVAISNNHSSNMYFHGEGGGEG-APTFSVWNDT
    AtBBM(AAM33803) (541)  QQQIQQSPGGDFPVAISNNHSSNMYFHGEGGGEG-APTFSVWNDT
    BnBBM1(AAM33800)(539)  TQ---QSPGGDFPAAMTNNVGSNMYYHGEGGGEV-APTFTVWNDN
    BnBBM2(AAM33801)(539)  TQ----HSPGGDFPAAMTNNVGSNMYYHGEGGGEV-APTFTVWNDN
   AtODP(NP_175530) (522)  EEFPAVKVDYDMPPSGGATGYGGWNSGESAQGSNPGGVFTMWNE-
    AtODP(BAB02492) (498)  EEFPTVKTDYDMPSSDGTGGYSGWTS-ESVQGSNPGGVFTMWNE-
   AtODP(AAD030633) (473)  EEFPAVKVDYDMPPSGGATGYGGWNSGESAQGSNPGGVFTMWNE-
         Consensus  (701)           GDFP A A    AS         G G    A  LFSVWND
```

FIG. 1D

```
                              1                                                  50
ZM-ODP2_unmodifiedPEP    (1)  ░░░░░░░░░░░░░░░░░░░░░░░░ILAA░░░░░░░░░░░░░░░░░░░░
ZM-ODP2_modifiedPEP_id_97.3 (1) ░░░░░░░░░░░░░░░░░░░░░░ILAA░░░░░░░░░░░░L░░░░░
ZM-ODP2_modifiedPEP_id_92.4 (1) ░I░░░░░░░░I░░░░░░░░░IL░A░░░░░░░░░░░░L░░░░░
ZM-ODP2_modifiedPEP_id_87.3 (1) ░I░░░░░░░░I░░░░░░░░░IL░G░░░░░I░░░░░░L░░░░░
ZM-ODP2_modifiedPEP_id_82.4 (1) ░I░░░░░░░░I░░░░░░░░░IL░G░░░░I░░░░░░░L░░░░░
                  Consensus (1) MATINNWLAFSLSPQEIPPSQTTDSTILSAATADHISGDVCFNLPQDWSM
                              51                                                 100
ZM-ODP2_unmodifiedPEP   (51)  ░░░░A░V░A░░░░░░░░░░░░░░A░░░░░░░░░░░V░A░░░A░
ZM-ODP2_modifiedPEP_id_97.3 (51) ░░I░AIVA░░I░░I░░L░░░░░A░░░░░L░░░░░░V░A░░A░
ZM-ODP2_modifiedPEP_id_92.4 (51) ░░I░AIIA░░I░░I░░L░░░░░A░░░░░L░░░░░I░A░░A░
ZM-ODP2_modifiedPEP_id_87.3 (51) ░░I░GII░░I░I░I░GL░░░░GV░░░░L░░░░░I░G░░G░
ZM-ODP2_modifiedPEP_id_82.4 (51) ░░I░GII░░I░I░I░GL░░░░GV░░░░L░░░░░I░G░░G░
                  Consensus (51) RGSEISAIIAEPKIEDFIGGLSFSEQHHKANCNMLPSTSSTICYASSGAS
                              101                                                150
ZM-ODP2_unmodifiedPEP  (101)  ░░░░░░░░░░AL░A░V░A░░A░V░░A░░AAA░V░AA░
ZM-ODP2_modifiedPEP_id_97.3 (101) ░░I░░░░AI░A░VVA░AV░░A░I░AAA░V░AA░
ZM-ODP2_modifiedPEP_id_92.4 (101) ░░I░░░░AI░A░I░IA░A░I░GA░I░AAA░IA░AA░
ZM-ODP2_modifiedPEP_id_87.3 (101) ░░I░░░░GI░G░I░IG░G░I░GG░GGGG░I░GG░
ZM-ODP2_modifiedPEP_id_82.4 (101) ░░I░░░░GI░G░I░IG░G░I░GG░GGGG░I░GG░
                  Consensus (101) TGYHHQIYHQPTSSAIHFADSIMIASSAGIHDGGAMISAAAANGIAGAAS
                              151                                                200
ZM-ODP2_unmodifiedPEP  (151)  A░░░░░░░░A░░░░VAAA░A░L░L░░A░░░░AA░
ZM-ODP2_modifiedPEP_id_97.3 (151) A░░░░░░░░A░░░░VAAA░A░I░I░░A░░░AA░
ZM-ODP2_modifiedPEP_id_92.4 (151) A░░░░░░░░A░░░░░IAAA░A░I░I░░A░░░AA░
ZM-ODP2_modifiedPEP_id_87.3 (151) ░░░░░░░░░░░░░░░GG░G░I░I░G░░░G░
ZM-ODP2_modifiedPEP_id_82.4 (151) ░░░░░░░░░░░░░░░GG░G░I░I░░░░G░
                  Consensus (151) ANGGGIGLSMIKNWLRSQPAPMQPRIAAAEGAQGISISMNMAGTTQGAAG
                              201                                                250
ZM-ODP2_unmodifiedPEP  (201)  ░LLA░A░A░░V░A░AVV░A░░░░VA░AVVAV░
ZM-ODP2_modifiedPEP_id_97.3 (201) ░LLA░A░A░░V░A░AVV░A░░░░VA░AVVAV░
ZM-ODP2_modifiedPEP_id_92.4 (201) ░IVA░A░A░I░A░AIII░A░░░░LAAVLAL░
ZM-ODP2_modifiedPEP_id_87.3 (201) ░IV░░░░░I░G░GIII░A░░░░LAAVLAL░
ZM-ODP2_modifiedPEP_id_82.4 (201) ░IV░░░░░I░G░GIII░G░░░░L░GVLGL░
                  Consensus (201) MPIVAGERARAPESISTSAQGGAIIITAPKEDSGGSGLAGAVLALSTDTG
                              251                                                300
ZM-ODP2_unmodifiedPEP  (251)  ░░░A░A░░A░░░░░░░░░░░░░░░░░░░░░░
ZM-ODP2_modifiedPEP_id_97.3 (251) ░░░A░A░░A░░░░░░░░░░░░░░░░░░░░░
ZM-ODP2_modifiedPEP_id_92.4 (251) ░░░A░A░░A░░░░░░░░░░░░░░░░░░░░░
ZM-ODP2_modifiedPEP_id_87.3 (251) ░░░A░A░░A░░░░░░░░░░░░░░░░░░░░░
ZM-ODP2_modifiedPEP_id_82.4 (251) ░░░G░G░░░░░░░░░░░░░░░░░░░░░░░░
                  Consensus (251) GSGGASADNTARKTVDTFGQRTSIYRGVTRHRWTGRYEAHLWDNSCRREG
                              301                                                350
ZM-ODP2_unmodifiedPEP  (301)  ░░░░░░░░░░░░░░░░░░░░░░░░░░░░░░░
ZM-ODP2_modifiedPEP_id_97.3 (301) ░░░░V░░░░░░░░░░░░░░░░░░░░░░░░░
ZM-ODP2_modifiedPEP_id_92.4 (301) ░░░░░░░░░░░░░░░░░░░░░░░░░░░░░░
ZM-ODP2_modifiedPEP_id_87.3 (301) ░░░░░░░░░░░░░░░░░░░░░░░░░░░░░░
ZM-ODP2_modifiedPEP_id_82.4 (301) ░░░░░░░░░░░░░░░░░░░░░░░░░░░░░░
                  Consensus (301) QTRKGRQVYLGGYDKEEKAARAYDLAALKYWGATTTTNFPVSNYEKELED
                              351                                                400
ZM-ODP2_unmodifiedPEP  (351)  ░░░░░░░░░░░░░░░░░░░░░░░░░░░░░░░
ZM-ODP2_modifiedPEP_id_97.3 (351) ░░░░░░░░░░░░░░░░░░░░░░░░░░░░░░
ZM-ODP2_modifiedPEP_id_92.4 (351) ░░░░░░░░░░░░░░░░░░░░░░░░░░░░░░
ZM-ODP2_modifiedPEP_id_87.3 (351) ░░░░░░░░░░░░░░░░░░░░░░░░░░░░░░
ZM-ODP2_modifiedPEP_id_82.4 (351) ░░░░░░░░░░░░░░░░░░░░░░░░░░░░░░
                  Consensus (351) MKHMTRQEFVASLRRKSSGFSRGASIYRGVTRHHQHGRWQARIGRVAGNK
                              401                                                450
ZM-ODP2_unmodifiedPEP  (401)  ░░░░░░░░░░░░░░░░░░░░░░░░░░░░░░░
ZM-ODP2_modifiedPEP_id_97.3 (401) ░░░░░░░░░░░░░░░░░░░░░░░░░░░░░░
ZM-ODP2_modifiedPEP_id_92.4 (401) ░░░░░░░░░░░░░░░░░░░░░░░░░░░░░░
ZM-ODP2_modifiedPEP_id_87.3 (401) ░░░░░░░░░░░░░░░░░░░░░░░░░░░░░░
ZM-ODP2_modifiedPEP_id_82.4 (401) ░░░░░░░░░░░░░░░░░░░░░░░░░░░░░░
                  Consensus (401) DLYLGTFSTQEEAAEAYDIAAIKFRGLNAVTNFDMSRYDVKSILDSSALP
```

FIG. 2A

```
                              451                                                    500
ZM-ODP2_unmodifiedPEP    (451) ▓▓▓▓▓▓▓▓▓▓▓AA▓A▓▓▓▓A▓▓▓▓▓▓▓▓A▓▓▓▓▓▓A▓AAA▓▓A▓
ZM-ODP2_modifiedPEP_id_97.3 (451) ▓A▓▓▓▓▓▓▓▓AA▓A▓▓▓▓A▓▓▓▓▓▓VA▓▓▓▓▓▓▓A▓AAA▓▓A▓
ZM-ODP2_modifiedPEP_id_92.4 (451) ▓▓▓▓▓▓▓▓▓▓AA▓A▓▓▓▓A▓LL▓▓▓L▓▓VA▓▓V▓▓▓▓AVAAA▓▓A▓
ZM-ODP2_modifiedPEP_id_87.3 (451) ▓▓▓▓▓▓▓▓▓▓AA▓A▓▓▓▓A▓LL▓▓▓L▓▓VA▓▓V▓▓▓▓AVAAA▓▓A▓
ZM-ODP2_modifiedPEP_id_82.4 (451) ▓▓▓▓▓▓▓▓▓▓▓▓▓▓▓▓▓▓▓▓LL▓▓▓L▓▓V▓▓▓V▓▓▓▓GV▓▓▓▓▓▓
               Consensus (451) IGSAAKRLKEAEAAASAQHHHAGLLSYDLGRVASQVGDGGAVAAAYGAHY
                              501                                                    550
ZM-ODP2_unmodifiedPEP    (501) ▓▓AA▓▓▓▓A▓▓▓AA▓▓▓▓▓▓▓▓▓▓▓▓▓▓▓▓▓▓▓▓▓AV▓AAA▓▓
ZM-ODP2_modifiedPEP_id_97.3 (501) ▓AA▓▓VA▓▓▓AA▓▓▓▓V▓▓▓A▓▓▓▓▓▓▓▓▓▓▓▓▓▓AV▓AAA▓▓
ZM-ODP2_modifiedPEP_id_92.4 (501) ▓AA▓▓VA▓▓▓AA▓▓V▓▓▓A▓▓▓▓▓▓▓▓▓▓▓▓▓▓ALVAAA▓▓V▓
ZM-ODP2_modifiedPEP_id_87.3 (501) ▓AA▓▓VA▓▓▓AA▓▓V▓▓▓A▓▓▓▓▓▓▓▓▓▓▓▓▓▓HALVAAA▓▓V▓
ZM-ODP2_modifiedPEP_id_82.4 (501) ▓▓▓▓▓V▓▓▓▓▓▓▓▓V▓▓▓▓▓▓▓▓▓▓▓▓▓▓▓▓▓▓GLV▓▓▓▓▓V▓
               Consensus (501) HGAAWPTVAFQPGAASTGVYHPYAQQPMRGGGWCKQEQDHALVAAAHSVQ
                              551                                                    600
ZM-ODP2_unmodifiedPEP    (551) ▓▓▓▓▓▓▓▓AA▓A▓▓▓▓▓A▓▓▓AAAA▓▓▓▓▓L▓▓▓▓L▓▓▓▓▓▓▓▓
ZM-ODP2_modifiedPEP_id_97.3 (551) ▓▓▓▓▓▓▓▓AA▓A▓▓▓▓▓A▓▓▓AAAA▓▓▓▓▓V▓▓▓▓▓▓▓▓▓▓▓▓
ZM-ODP2_modifiedPEP_id_92.4 (551) ▓V▓▓V▓V▓AA▓A▓▓▓▓▓A▓▓▓AAAA▓▓▓V▓▓V▓▓▓▓V▓▓▓▓▓▓
ZM-ODP2_modifiedPEP_id_87.3 (551) ▓V▓▓V▓V▓AA▓A▓▓▓▓▓A▓▓▓AAAA▓▓▓V▓▓V▓▓▓▓V▓▓▓▓▓▓
ZM-ODP2_modifiedPEP_id_82.4 (551) ▓V▓▓V▓V▓G▓▓▓▓▓▓▓▓G▓▓▓G▓▓▓▓▓▓▓V▓▓V▓▓▓▓▓▓▓▓▓▓
               Consensus (551) DVHHVNVGAAGAHDFFSAGQQAAAAAMHGVGSVDSASVEHSTGSNSVVYN
                              601                                                    650
ZM-ODP2_unmodifiedPEP    (601) ▓▓▓▓▓▓▓▓▓▓▓▓▓▓▓▓▓▓▓▓▓▓▓▓▓▓▓▓▓▓▓▓V▓▓▓▓▓▓▓▓▓
ZM-ODP2_modifiedPEP_id_97.3 (601) ▓▓V▓▓▓▓▓▓▓V▓▓▓▓▓▓▓▓▓▓▓▓▓▓▓▓▓▓▓▓▓V▓QV▓AAA▓▓
ZM-ODP2_modifiedPEP_id_92.4 (601) ▓▓L▓▓▓▓▓▓▓L▓▓▓▓▓▓▓▓▓▓▓▓▓▓▓▓▓▓▓L▓▓▓V▓▓▓▓▓▓▓
ZM-ODP2_modifiedPEP_id_87.3 (601) ▓▓L▓▓▓▓▓▓▓L▓▓▓▓▓▓▓▓▓▓▓▓▓▓▓▓▓▓▓L▓▓▓▓L▓▓▓▓▓▓
ZM-ODP2_modifiedPEP_id_82.4 (601) ▓▓L▓▓▓▓▓▓▓L▓▓▓▓▓▓▓▓▓▓▓▓▓▓▓▓▓▓▓L▓▓▓▓L▓▓▓▓▓▓
               Consensus (601) GGLGDSNGASALGGSGGGYMMPMSAAGATTTSAMLSHEQVHARAYDEAKQ
                              651                                                    700
ZM-ODP2_unmodifiedPEP    (651) ▓▓▓▓▓▓▓▓▓▓▓▓▓▓▓▓▓▓▓▓▓▓▓▓▓▓▓VV▓▓▓▓▓▓▓▓▓▓▓▓▓▓
ZM-ODP2_modifiedPEP_id_97.3 (651) ▓▓▓▓▓▓▓▓▓▓▓▓▓▓▓▓▓▓▓▓▓▓▓▓▓▓▓VV▓▓▓▓▓▓▓▓▓▓▓▓▓▓
ZM-ODP2_modifiedPEP_id_92.4 (651) ▓▓▓▓▓▓▓▓▓▓▓▓▓▓▓▓▓▓▓▓▓▓▓▓▓▓▓VV▓▓▓▓▓▓▓▓▓▓▓▓▓▓
ZM-ODP2_modifiedPEP_id_87.3 (651) ▓▓▓▓▓▓▓▓▓▓▓▓▓▓▓▓▓▓▓▓▓▓▓▓▓▓▓LL▓▓▓▓▓▓▓▓▓▓▓▓▓▓
ZM-ODP2_modifiedPEP_id_82.4 (651) ▓▓▓▓▓▓▓▓▓▓▓▓▓▓▓▓▓▓▓▓▓▓▓▓▓▓▓LL▓▓▓▓▓▓▓▓▓▓▓▓▓▓
               Consensus (651) AAQMGYESYLVNAENNGGGRMSAWGTVVSAAAAAAASSNDNMAADVGHGG
                              701
ZM-ODP2_unmodifiedPEP    (701) ▓▓▓▓▓▓▓▓
ZM-ODP2_modifiedPEP_id_97.3 (701) ▓▓▓▓▓▓▓▓
ZM-ODP2_modifiedPEP_id_92.4 (701) ▓▓▓▓▓▓▓▓
ZM-ODP2_modifiedPEP_id_87.3 (701) ▓▓▓▓▓▓▓▓
ZM-ODP2_modifiedPEP_id_82.4 (701) ▓▓▓▓▓▓▓▓
               Consensus (701) AQLFSVWNDT
```

FIG. 2B

AP2 DOMAIN TRANSCRIPTION FACTOR ODP2 (OVULE DEVELOPMENT PROTEIN 2) AND METHODS OF USE

CROSS-REFERENCE TO RELATED APPLICATIONS

This application is a continuation of U.S. application Ser. No. 15/131,181, filed Apr. 18, 2016, now U.S. Pat. No. 10,113,175, which is a Division of U.S. application Ser. No. 13/790,641, filed Mar. 8, 2013, now U.S. Pat. No. 9,340,796, which is a continuation of U.S. application Ser. No. 12/503,482, filed on Jul. 15, 2009, now U.S. Pat. No. 8,420,893, which is a continuation of U.S. application Ser. No. 11/045,802, filed on Jan. 28, 2005, now U.S. Pat. No. 7,579,529, which claims priority to U.S. Provisional Application No. 60/541,122, filed on Feb. 2, 2004, all of which are hereby incorporated by reference in their entireties.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1759USCNT4 SequenceListing created on Sep. 25, 2018 and having a size of 146 kilobytes and is filed concurrently with the specification. The sequence listing contained in this ASCII formatted document is part of the specification and is herein incorporated by reference in its entirety.

FIELD OF THE INVENTION

The invention relates to the field of the genetic manipulation of plants, particularly the modulation of gene activity and development in plants.

BACKGROUND OF THE INVENTION

Cell division plays a crucial role during all phases of plant development. The continuation of organogenesis and growth responses to a changing environment requires precise spatial, temporal and developmental regulation of cell division activity in meristems. Such control of cell division is also important in organs themselves for example, leaf expansion, and secondary growth. A complex network controls cell proliferation in eukaryotes. Various regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions. The regulation of cell division impacts a variety of developmental pathways including transformation and plant regeneration.

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming.

For example, it is difficult to obtain a culture response from some maize genotypes. Typically, a suitable culture response has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be more efficiently introduced into and evaluated directly into inbreds. Accordingly, methods are needed in the art to increase transformation efficiencies of plants.

Influencing cell cycle and cell division can also affect various developmental pathways in a plant. Pathways of interest include those that influence embryo development. The AP2/ERF family of proteins is a plant-specific class of putative transcription factors that have been shown to regulate a wide-variety of developmental processes and are characterized by the presence of a AP2/ERF DNA binding domain. The AP2/ERF proteins have been subdivided into two distinct subfamilies based on whether they contains one (ERF subfamily) or two (AP2 subfamily) DNA binding domains.

One member of the AP2 family that has been implicated in a variety of critical plant cellular functions is the Baby Boom protein (BBM). The BBM protein from *Arabidopsis* is preferentially expressed in seed and has been shown to play a central role in regulating embryo-specific pathways. Overexpression of BBM has been shown to induce spontaneous formation of somatic embryos and cotyledon-like structures on seedlings. See, Boutiler et al. (2002) *The Plant Cell* 14:1737-1749. Thus, members of the AP2 protein family promote cell proliferation and morphogenesis during embryogenesis. Such activity finds potential use in promoting apomixis in plants.

Apomixis refers to the production of a seed from the maternal ovule tissue in the absence of egg cell fertilization (Koltunow (1995) *Plant Physiol* 108:1345-1352). Apomixis is a valuable trait for crop improvement since apomictic seeds give rise to clonal offspring and can therefore be used to genetically fix hybrid lines. The production of hybrid lines is intensive and costly. Production of seed through apomixis avoids these problems in that once a hybrid has been produced, it can be maintained clonally, thereby eliminating the need to maintain and cross separate parent lines. The use of apomictic seeds also eliminates the use of cuttings or tissue culture techniques to propagate lines, reduces the spread of disease which are easily spread through vegetative-propagated tissues and in many species reduces the size of the propagule leading to lower shipping and planting costs. Methods are therefore needed for the efficient production of apomictic seed.

Members of the APETALA2 (AP2) family of proteins play critical roles in a variety of important biological events including development, plant regeneration, cell division, etc. Accordingly, it is valuable to the field of agronomic development to identify and characterize novel AP2 family members and develop novel methods to modulate embryogenesis, transformation efficiencies, oil content, starch content and yield in a plant.

BRIEF SUMMARY OF THE INVENTION

Methods and compositions are provided to modulate plant development using DNA, RNA or protein derived from the maize AP2 family member ZmODP2. The present invention provides an isolated polypeptide comprising an amino acid sequence selected from the group consisting of: (a) the polypeptide comprising the amino acid sequence of SEQ ID NO:2, 26, or 28; (b) the polypeptide having at least 50%, sequence identity to SEQ ID NO:2, 26, or 28, wherein the polypeptide has Ovule Development Protein 2 (ODP2)

activity; (c) the polypeptide encoded by a polynucleotide that hybridizes under stringent conditions to a polynucleotide comprising the complement of SEQ ID NOS:1, 3, 25, or 27, wherein the stringent conditions comprise hybridization in 50% formamide, 1 M NaCl, 1% SDS at 37° C., and a wash in 0.1×SSC at 60° C. to 65° C.; and, (d) the polypeptide having at least 70 consecutive amino acids of SEQ ID NO:2, 26, or 28, wherein the polypeptide retains ODP2 activity.

Further compositions of the invention include an isolated polynucleotide selected from the group consisting of: (a) the polynucleotide comprising SEQ ID NO:1, 3, 25 or 27; (b) the polynucleotide encoding the amino acid sequence of SEQ ID NO:2, 26 or 28; (c) the polynucleotide having at least 50% sequence identity to SEQ ID NO:1, 3, 25 or 27, wherein the polynucleotide encodes a polypeptide having ODP2 activity; (d) the polynucleotide having at least 200 consecutive nucleotides of SEQ ID NO:1, 3, 25 or 27 or a complement thereof; and, (e) the polynucleotide that hybridizes under stringent conditions to the complement of the polynucleotide of (a), wherein the stringent conditions comprise hybridization in 50% formamide, 1 M NaCl, 1% SDS at 37° C., and a wash in 0.1×SSC at 60° C. to 65° C. Nucleotide constructs comprising the polynucleotide of the invention are also provided.

Additional compositions of the invention include plants having a heterologous polynucleotide of the invention operably linked to a promoter that drives expression in the plant. The plant can be a plant cell, a plant part, a seed, or a grain. Methods are provided to modulate development in a plant. In one embodiment, the plant of the invention has an altered oil phenotype. In specific embodiments the oil content of the plant is decreased. In other embodiments, starch production of the plant is modified. In specific embodiments, the starch content of the plant is increased. In another embodiment, the regenerative capacity of the plant is modified. In yet another embodiment, the plant produces an asexually derived embryo. In still another embodiment, the transformation efficiency of the plant is increased. In another embodiment, the seed set is increased or maintained during periods of abiotic stress. In still another embodiment, haploid embryos are produced from male or female gametes.

Methods of the invention comprise methods for modulating the activity and/or level of a polypeptide in a plant. This method comprises providing to the plant an ODP2 sequence of the invention.

The present invention further provides a method for altering the oil phenotype in a plant. The method comprises providing to the plant an ODP2 sequence of the invention; and, thereby altering the oil phenotype of the plant.

The present invention further provides a method for modifying starch production in a plant. The method comprises providing to the plant an ODP2 sequence of the invention; and, thereby modifying starch production of the plant.

The present invention further provides a method for producing asexually derived embryos. The method comprises introducing into a plant ODP2 sequence of the present invention; and, thereby producing asexually derived embryos. The asexually derived embryos can be somatic embryos, adventitious embryos, or gametophytic embryos.

The present invention also provides a method for modifying the regenerative capacity of a plant. The method comprises introducing into the plant an ODP2 nucleotide sequence of the invention, and thereby modifying the regenerative capacity of the plant.

The present invention also provides a method of transforming a plant. The method comprises providing to target plant an ODP2 sequence of the invention, and, transforming into the target plant a nucleotide sequence of interest. The regenerative capacity can be modified to include tissues normally not amenable to culture including but not limited to leaves, stems, and mature seed.

The invention further provides a method for increasing transformation efficiency in a plant. The method comprises providing to the plant an ODP2 nucleotide sequence of the invention, and thereby increasing the transformation efficiency of the plant.

The invention further provides a method for increasing or maintaining yield in a plant under abiotic stress. The method comprises providing to the plant an ODP2 nucleotide sequence of the invention, and thereby increasing the stress tolerance of the plant.

BRIEF DESCRIPTION OF THE DRAWINGS

FIGS. 1A-1D show an alignment of the amino acid sequence of maize Ovule Development Protein 2 (Zm-ODP2) (SEQ ID NO:2) with OsAnt (Accession No. BAB89946; SEQ ID NO:26), OSBNM (Accession No. AAL47205; SEQ ID NO:28); OSODP (Accession No. CAE05555; SEQ ID NO:29); AtODP (NP_197245; SEQ ID NO:30); ATBBM (Accession No. AAM33803; SEQ ID NO:31); BnBBM1 (AAM33800; SEQ ID NO:32); BnBBM2 (Accession No. AAM33801; SEQ ID NO:33); ATODP (Accession No. NP_175530; SEQ ID NO:34); AtODP (Accession No. BAB02492; SEQ ID NO:35); AtODP (Accession No. AAD30633; SEQ ID NO:36). All 11 proteins present in the alignment have two AP2 (APETALA2; pfam00847.8) domains. Using the amino acid numbering of the Zm-ODP2 polypeptide, the first AP2 domain is from about amino acid 273 to about 343 and the second AP2 domain is from about amino acid 375 to about 437. A consensus sequence for all 11 aligned polypeptides is also provided (SEQ ID NO:37).

FIGS. 2A-2B provide an amino acid alignment of the Zm-ODP2 amino acid sequence (ZM-ODP2_unmodifiedPEP; SEQ ID NO:2) with four polypeptide variants of the Zm-ODP2 sequence. The variant amino acid sequences include ZM-ODP2_modifiedPEP_id_97.3 (SEQ ID NO:20) which shares 97.3% amino acid sequence identity with SEQ ID NO:2; ZM-ODP2_modifiedPEP_id_92.4 (SEQ ID NO:21) which shares 92.4% amino acid sequence identity with SEQ ID NO:2; ZM-ODP2_modifiedPEP_id_87.3 (SEQ ID NO:22) which shares 87.3% amino acid sequence identity with SEQ ID NO:2; and, ZM-ODP2_modifiedPEP_id_82.4 (SEQ ID NO:23) which shares 82.4% amino acid sequence identity with SEQ ID NO:2. The consensus sequence is set forth in SEQ ID NO:24.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The article "a" and "an" are used herein to refer to one or more than one (i.e., to at least one) of the grammatical object of the article. By way of example, "an element" means one or more element.

COMPOSITIONS

Compositions of the invention include polynucleotide sequence and amino acid sequence of Ovule Development Protein 2 (ODP2) proteins that are involved in regulating plant growth and development. In particular, the present invention provides for isolated nucleic acid molecules comprising nucleotide sequences encoding the amino acid sequences shown in SEQ ID NO:2, 26, or 28. Further provided are polypeptides having an amino acid sequence encoded by a nucleic acid molecule (SEQ ID NO: 1, 3, 25, or 27) described herein, and fragments and variants thereof.

The ODP2 polypeptides of the invention contain two predicted APETALA2 (AP2) domains and are members of the AP2 protein family (PFAM Accession PF00847). The AP2 domains of the maize ODP2 polypeptide are located from about amino acids S273 to N343 and from about S375 to R437 of SEQ ID NO:2). The AP2 family of putative transcription factors have been shown to regulate a wide range of developmental processes, and the family members are characterized by the presence of an AP2 DNA binding domain. This conserved core is predicted to form an amphipathic alpha helix that binds DNA. The AP2 domain was first identified in APETALA2, an *Arabidopsis* protein that regulates meristem identity, floral organ specification, seed coat development, and floral homeotic gene expression. The AP2 domain has now been found in a variety of proteins.

The ODP2 polypeptides of the invention share homology with several polypeptides within the AP2 family. FIGS. 1A-1D provide an alignment of the maize and rice ODP2 polypeptides of the present invention with 8 other proteins having two AP2 domains. A consensus sequence of all proteins appearing in the alignment is also provided in FIG. 1. The alignment of FIGS. 1A-1D was generated using Align X® which employs a modified Clustal W algorithm to generate multiple sequence alignments. FIGS. 1A-1D demonstrate that the maize ODP2 polypeptide of the present invention (SEQ ID NO:2) shares about 51.7% sequence identity and 62.3% sequence similarity across the full sequence with the rice sequences of OsBNM3 (ovule development aintegumenta-like protein) (Genbank Accession No. AAL47205; SEQ ID NO:28). In addition, the ODP2 polypeptide of SEQ ID NO:2 shares 65.4% sequence identity and 72.7% sequence similarity across the full sequence to a putative ovule development protein from rice (OS) (Genbank Accession No. BAB89946; SEQ ID NO:26).

The OsBNM3 polypeptide sequence (SEQ ID NO:28), the OS polypeptide (SEQ ID NO:26), as well as the ODP2 sequence (SEQ ID NO:2) share homology with *Arabidopsis* Baby Boom (AtBBM, AAM33803; SEQ ID NO:31). Blast alignments demonstrate that Zm-ODP2 shares about 38.1% sequence identity and about 46.3% sequence similarity across the full length of the *Arabidopsis* Baby Boom polypeptide (AtBBM). See FIGS. 1A-1D. The AtBBM polypeptide encodes an AP2 domain transcription factor and is optimally expressed in the developing embryo and seeds. AtBBM has been shown to trigger formation of somatic embryos and cotyledon-like structures on seedlings and thus activates signal transduction pathways leading to the induction of embryo development from differentiated somatic cells. See, for example, Boutiler et al. (2002) *Plant Cell* 14:1737-49), herein incorporated by reference. Accordingly, the ODP2 sequences of the present invention also find use in modifying the regenerative capabilities of plants and rendering the plant embryogenic.

In addition, other polypeptides that influence ovule and embryo development and stimulate cell growth, such as, Lec1, Kn1 family, WUSCHEL, Zwille, and Aintegumeta (ANT) allow for increased transformation efficiencies when expressed in plants. See, for example, U.S. Application No. 2003/0135889, herein incorporated by reference. In fact, a maize Lec1 homologue of the *Arabidopsis* embryogenesis controlling gene AtLEC1, has been shown to increase oil content and transformation efficiencies in plants. See, for example, WO 03001902 and U.S. Pat. No. 6,512,165. Accordingly, the Zm-ODP2 sequences of the invention find further use in increasing transformation efficiencies in plants.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Optimally, an "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence have ODP2 activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

By "ODP2 activity" or "Ovule Development Protein 2 activity" is intended the ODP2 polypeptide has at least one of the following exemplary activities: increases the regenerative capability of a plant cell, renders the plant cell embryogenic, increases the transformation efficiencies of a plant cell, alters the oil content of a plant cell, binds DNA, increases abiotic stress tolerance, increases or maintains yield under abiotic stress, increases asexual embryo formation, alters starch content, alters embryo size or activates transcription. Methods to assay for such activity are known in the art and are described more fully below.

A fragment of an ODP2 nucleotide sequence that encodes a biologically active portion of an ODP2 protein of the invention will encode at least 15, 25, 30, 50, 100, 150, 200, 250, 300, 350, 400, 450, 500, 550, 600, 650, 700, 709 contiguous amino acids, or up to the total number of amino acids present in a full-length ODP2 protein of the invention (for example, 710 amino acids for SEQ ID NO: 2, 692 amino acids for SEQ ID NO: 25 and 597 for SEQ ID NO:27). Fragments of an ODP2 nucleotide sequence that are useful as hybridization probes or PCR primers generally need not encode a biologically active portion of an ODP2 protein.

Thus, a fragment of an ODP2 nucleotide sequence may encode a biologically active portion of an ODP2 protein, or it may be a fragment that can be used as a hybridization probe or PCR primer using methods disclosed below. A biologically active portion of an ODP2 protein can be prepared by isolating a portion of one of the ODP2 nucleotide sequences of the invention, expressing the encoded portion of the ODP2 protein (e.g., by recombinant expression in vitro), and assessing the activity of the encoded portion of the ODP2 protein. Nucleic acid molecules that are fragments of an ODP2 nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1,500, 1,600, 1,700, 1,800, 1,900, 2,000, 2,100, 2,200 contiguous nucleotides, or up to the number of nucleotides present in a full-length ODP2 nucleotide sequence disclosed herein (for example, 2,260, 2133, 2079, and 1794 nucleotides for SEQ ID NOS:1, 3, 25 and 27, respectively).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the ODP2 polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an ODP2 protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:2, 26, or 28 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, the polypeptide has ODP2 activity (i.e., modulating the regenerative capability of a plant, rendering the plant embryogenic, increasing the transformation efficiency of a plant, altering oil content of a plant, increasing cell proliferation, increasing abiotic stress tolerance, increasing or maintaining yield under abiotic stress, modifying starch content, increasing asexual embryo formation, binding DNA or regulating transcription) as described herein. Such variants may result from, for example, genetic polymorphism or from human manipulation. Biologically active variants of a native ODP2 protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the ODP2 proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ODP2 activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. Various methods for screening for ODP2 activity are discussed in detail elsewhere herein.

Variant nucleotide sequences and proteins also encompass sequences and proteins derived from a mutagenic and recombinogenic procedure such as DNA shuffling. With such a procedure, one or more different ODP2 coding sequences can be manipulated to create a new ODP2 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the ODP2 gene of the invention and other known ODP2 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants including other monocots. In this manner, methods such as PCR, hybridization, and the like can be used to identify such sequences based on their sequence homology to the sequence set forth herein. Sequences isolated based on their sequence identity to the entire ODP2 sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode for an ODP2 protein and which hybridize under stringent conditions to the ODP2 sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, N.Y.); Innis and Gelfand, eds. (1995) *PCR Strategies* (Academic Press, New York); and Innis and Gelfand, eds. (1999) *PCR Methods Manual* (Academic Press, N.Y.). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the ODP2 sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire ODP2 sequence disclosed herein, or one or more portions thereof, may be used as a probe capable of specifically hybridizing to corresponding ODP2 sequences and messenger RNAs. To achieve specific hybridization under a variety of conditions, such probes include sequences that are unique among ODP2 sequences and are optimally at least about 10 nucleotides in length, and at least about 20 nucleotides in length. Such probes may be used to amplify corresponding ODP2 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTN program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, optimally at least 80%, more optimally at least 90%, and most optimally at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more optimally at least 70%, 80%, 90%, and most optimally at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, optimally 80%, more optimally 85%, most optimally at least 90% or 95% sequence identity to the reference sequence over a specified comparison window. Optimally, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention further provides plants, plant cells, and plant parts having altered levels and/or activities of the ODP2 polypeptides of the invention. In some embodiments, the plants of the invention have stably incorporated the ODP2 sequences of the invention. As discussed elsewhere herein, altering the level/activity of the ODP2 sequences of the invention can produce a variety to phenotypes. As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein "grain" is intended the mature seed produced by commercial growers for purposes other than growing or reproducing the species. Progeny, variants, and mutants of the regenerated plants are also included within the scope of the invention, provided that these parts comprise the introduced nucleic acid sequences.

A "subject plant or plant cell" is one in which an alteration, such as transformation or introduction of a polypeptide, has occurred, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

METHODS

I. Providing Sequences

The use of the term "nucleotide constructs" or "polynucleotide" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The nucleic acid sequences of the present invention can be introduced/expressed in a host cell such as bacteria, yeast, insect, mammalian, or optimally plant cells. It is expected that those of skill in the art are knowledgeable in the numerous systems available for the introduction of a polypeptide or a nucleotide sequence of the present invention. No attempt to describe in detail the various methods known for providing proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form and/or genomic location.

By "host cell" is meant a cell, which comprises a heterologous nucleic acid sequence of the invention. Host cells may be prokaryotic cells such as *E. coli*, or eukaryotic cells such as yeast, insect, amphibian, or mammalian cells. Optimally, host cells are monocotyledonous or dicotyledonous plant cells. A particularly optimal monocotyledonous host cell is a maize host cell.

The ODP2 sequences of the invention can be provided in expression cassettes for expression in the plant of interest. The cassette can include 5' and 3' regulatory sequences operably linked to an ODP2 sequence of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites for insertion of the ODP2 sequence to be under the transcriptional regulation of the regulatory regions. The expression cassette may additionally contain selectable marker genes.

The expression cassette can include in the 5'-3' direction of transcription, a transcriptional initiation region (i.e., a promoter) and translational initiation region, an ODP2 sequence of the invention, and a transcriptional and translational termination region (i.e., termination region) functional in plants. The promoter may be native/analogous or foreign to the plant host and/or to the ODP2 sequence of the invention. In one embodiment, the promoter employed in the methods of the invention is the native ODP2 promoter. See, for example, U.S. Provisional Application No. 60/541,171, entitled "*ODP2 Promoter and Methods of Use*", filed on Feb. 2, 2004. Additionally, the promoter may be a natural sequence or alternatively a synthetic sequence. Where the promoter is "foreign" to the plant host, it is intended that the promoter is not found in the native plant into which the promoter is introduced. Where the promoter is "foreign" to the ODP2 sequence of the invention, it is intended that the promoter is not the native or naturally occurring promoter for the operably linked ODP2 sequence of the invention. As used herein, a chimeric gene comprises a coding sequence operably linked to a transcription initiation region that is heterologous to the coding sequence.

While it may be optimal to express the sequences using foreign promoters, the native promoter sequences may be used. Such constructs would change expression levels of ODP2 in the plant or plant cell. Thus, the phenotype of the plant or plant cell can be altered.

The termination region may be native with the transcriptional initiation region, may be native with the operably linked ODP2 sequence of interest, may be native with the plant host, or may be derived from another source (i.e., foreign to the promoter, the ODP2 sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gown (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention. The promoters can be selected based on the desired outcome. That is, the nucleic acid can be combined with constitutive, tissue-preferred, developmentally regulated, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced ODP2 expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and, milps (myo-inositol-1-phosphate synthase); (see WO 00/11177 and U.S. Pat. No. 6,225,529; herein incorporated by reference). Gamma-zein is another endosperm-specific promoter (Boronat et al. (1986) *Plant Science* 47:95-102). Globulin-1 (Glob-1) is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa, 22 kDa zein, 27 kDa zein, gamma-zein, waxy, shrunken 1, shrunken 2, globulin 1, etc. See also WO 00/12733, where seed-preferred promoters from end1 and end2 genes are disclosed; herein incorporated by reference. Additional seed-preferred promoters include the oleosin promoter (WO 00/0028058), the lipid transfer protein (LTP) promoter (U.S. Pat. No. 5,525,716). Additional seed-preferred promoters include the Lec1 promoter, the Jip1 promoter, and the milps3 promoter (see, WO 02/42424).

The methods of the invention involve introducing a nucleotide construct or a polypeptide into a plant. By "introducing" is intended presenting to the plant the nucleotide construct (i.e., DNA or RNA) or a polypeptide in such a manner that the nucleic acid or the polypeptide gains access to the interior of a cell of the plant. The methods of the invention do not depend on a particular method for introducing the nucleotide construct or the polypeptide to a plant, only that the nucleotide construct gains access to the interior of at least one cell of the plant. Methods for introducing nucleotide constructs and/or polypeptide into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct or the polypeptide introduced into a plant does not integrate into the genome of the plant.

Thus the ODP2 sequences of the invention can be provided to a plant using a variety of transient transformation methods including, but not limited to, the introduction of ODP2 protein or variants thereof directly into the plant and the introduction of the an ODP2 transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the various viral vector systems can be used for transient expression or the ODP2 nucleotide construct can be precipitated in a manner that precludes subsequent release of the DNA (thus, transcription from the particle-bound DNA can occur, but the frequency with which its released to become integrated into the genome is greatly reduced). Such methods include the use of PEI, as outlined in more detail in Example 13.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the an ODP2 polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Optimally, plants of the present invention are crop plants (for example, corn, alfalfa, sunflower, *Brassica*, soybean, cotton, safflower, peanut, sorghum, wheat, millet, tobacco, etc.), more optimally corn and soybean plants, yet more optimally corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235); Mosbach et al. (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773-781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. In other embodiments, the polypeptide of the invention is introduced. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

A method for modulating the concentration and/or activity of the polypeptide of the present invention is provided. By "modulation" is intended any alteration in the level and/or activity (i.e., increase or decrease) that is statistically significant compared to a control plant or plant part. In general, concentration, composition or activity is increased or decreased by at least 5%, 10%, 20%, 30%, 40%, 50%, 60%, 70%, 80%, or 90% relative to a control plant, plant part, or cell. The modulation may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In specific embodiments, the polypeptides of the present invention are modulated in monocots, particularly maize.

The level of the ODP2 polypeptide may be measured directly, for example, by assaying for the level of the ODP2 polypeptide in the plant, or indirectly, for example, by measuring the ODP2 activity of the ODP2 polypeptide in the plant. Methods for determining the presence of ODP2 activity are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may incorporate into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprises at least one nucleotide.

In some embodiments, the activity and/or level of the ODP2 polypeptide of the invention is increased. An increase in the level or activity of the ODP2 polypeptide of the invention can be achieved by providing to the plant an ODP2 polypeptide. As discussed elsewhere herein, many methods are known the art for providing a polypeptide to a plant including, but not limited to, direct introduction of the polypeptide into the plant and/or introducing into the plant (transiently or stably) a nucleotide construct encoding a polypeptide having ODP2 activity. In other embodiments, the level or activity of an ODP2 polypeptide may be increased by altering the gene encoding the ODP2 polypeptide or its promoter. See, e.g. U.S. Pat. No. 5,565,350 and PCT/US93/03868. The invention therefore encompasses mutagenized plants that carry mutations in ODP2 genes, where the mutations increase expression of the ODP2 gene or increase the ODP2 activity of the encoded ODP2 polypeptide.

In some embodiments, the activity and/or level of the ODP2 polypeptide of the invention of is reduced or eliminated by introducing into a plant a polynucleotide that inhibits the level or activity of the ODP2 polypeptide of the invention. The polynucleotide may inhibit the expression of ODP2 directly, by preventing translation of the ODP2 messenger RNA, or indirectly, by encoding a polypeptide that inhibits the transcription or translation of an ODP2 gene encoding an ODP2 protein. Methods for inhibiting or eliminating the expression of a gene in a plant are well known in the art, and any such method may be used in the present invention to inhibit the expression of ODP2 in a plant. In other embodiments of the invention, the activity of ODP2 polypeptide is reduced or eliminated by transforming a plant cell with an expression cassette comprising a polynucleotide encoding a polypeptide that inhibits the activity of the ODP2 polypeptide. In other embodiments, the activity of an ODP2 polypeptide may be reduced or eliminated by disrupting the gene encoding the ODP2 polypeptide. The invention encompasses mutagenized plants that carry mutations in ODP2 genes, where the mutations reduce expression of the ODP2 gene or inhibit the ODP2 activity of the encoded ODP2 polypeptide.

Reduction of the activity of specific genes (also known as gene silencing or gene suppression) is desirable for several aspects of genetic engineering in plants. Methods for inhibiting gene expression are well known in the art and include, but are not limited to, homology-dependent gene silencing, antisense technology, RNA interference (RNAi), and the like. The general term homology-dependent gene silencing encompasses the phenomenon of cis-inactivation, trans-inactivation, and cosuppression. See Finnegan et al. (1994) *Biotech.* 12:883-888; and Matzke et al. (1995) *Plant Physiol.* 107:679-685; both incorporated herein in their entirety by reference. These mechanisms represent cases of gene silencing that involve transgene/transgene or transgene/endogenous gene interactions that lead to reduced expression of protein in plants. A "transgene" is a recombinant DNA construct that has been introduced into the genome by a transformation procedure. As one alternative, incorporation of antisense RNA into plants can be used to inhibit the expression of endogenous genes and produce a functional mutation within the genome. The effect is achieved by introducing into the cell(s) DNA that encodes RNA that is complementary to the sequence of mRNA of the target gene. See e.g. Bird et al. (1991) *Biotech and Gen. Eng. Rev.* 9:207-226; incorporated herein in its entirety by reference. See also the more detailed discussion herein below addressing these and other methodologies for achieving inhibition of expression or function of a gene.

Many techniques for gene silencing are well known to one of skill in the art, including, but not limited to, antisense technology (see, e.g., Sheehy et al. (1988) *Proc. Natl. Acad. Sci. USA* 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12:883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507), virus-induced gene silencing (Burton et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; WO 98/53083; Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, U.S. Patent Publication No. 20030175965; Panstruga et al. (2003) *Mol. Biol. Rep.* 30:135-140; Wesley et al. (2001) *Plant J.* 27:581-590; Wang and Waterhouse (2001) *Curr. Opin. Plant Biol.* 5:146-150; U.S. Patent Publication No. 20030180945; and, WO 02/00904, all of which are herein incorporated by reference); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference; and other methods or combinations of the above methods known to those of skill in the art.

It is recognized that with the polynucleotides of the invention, antisense constructions, complementary to at least a portion of the messenger RNA (mRNA) for the ODP2 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used.

The polynucleotides of the present invention may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference. Thus, many methods may be used to reduce or eliminate the activity of an ODP2 polypeptide. More than one method may be used to reduce the activity of a single ODP2 polypeptide. In addition, combinations of methods may be employed to reduce or eliminate the activity of the ODP2 polypeptides.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

The ODP2 polynucleotides of the present invention can also be combined with genes implicated in transcriptional regulation, homeotic gene regulation, stem cell maintenance and proliferation, cell division, and/or cell differentiation such as other ODP2 homologues; Wuschel (see, e.g, Mayer et al. (1998) *Cell* 95:805-815); clavata (e.g., CLV1, CVL2, CLV3) (see, e.g., WO 03/093450; Clark et al. (1997) *Cell* 89:575-585; Jeong et al. (1999) *Plant Cell* 11:1925-1934; Fletcher et al. (1999) *Science* 283:1911-1914); Clavata and Embryo Surround region genes (e.g., CLE) (see, e.g., Sharma et al. (2003) *Plant Mol. Biol.* 51:415-425; Hobe et al. (2003) *Dev Genes Evol* 2/3:371-381; Cock & McCormick (2001) *Plant Physiol* 126:939-942; and Casamitjana-Martinez et al. (2003) *Curr Riot* 13:1435-1441); baby boom (e.g., BNM3, BBM) (see, e.g., WO 00/75530; Boutiler et al. (2002) *Plant Cell* 14:1737-1749); Zwille (Lynn et al. (1999) *Dev* 126:469-481); leafy cotyledon (e.g., Lec1, Lec2) (see, e.g., Lotan et al. (1998) *Cell* 93:1195-1205; WO 00/28058; Stone et al. (2001) *PNAS* 98:11806-11811; and U.S. Pat. No. 6,492,577); Shoot Meristem-less (STM) (Long et al. (1996) *Nature* 379:66-69); ultrapetala (ULT) (see, e.g., Fletcher (2001) *Dev* 128:1323-1333); mitogen activated protein kinase (MAPK) (see, e.g., Jonak et al. (2002) *Curr Opin Plant Biol* 5:415); kinase associated protein phosphatase (KAPP) (see, e.g., Williams et al. (1997) *PNAS* 94:10467-10472; and Trotochaud et al. (1999) *Plant Cell* 11:393-406); ROP GTPase (see, e.g., Wu et al. (2001) *Plant Cell* 13:2841-2856; and Trotochaud et al. (1999) *Plant Cell* 11:393-406); fasciata (e.g., FAS1, FAS2) (see, e.g., Kaya et al. (2001) *Cell* 104:131-142); cell cycle genes (see, e.g., U.S. Pat. No. 6,518,487; WO 99/61619; and WO 02/074909), Shepherd (SHD) (see, e.g., Ishiguro et al. (2002) *EMBO J.* 21:898-908); Poltergeist (see, e.g., Yu et al. (2000) *Dev* 127:1661-1670; Yu et al. (2003) *Curr Biol* 13:179-188); Pickle (PKL) (see, e.g., Ogas et al. (1999) *PNAS* 96:13839-13844); knox genes (e.g., KN1, KNAT1) (see, e.g., Jackson et al. (1994) *Dev* 120:405-413; Lincoln et al. (1994) *Plant Cell* 6:1859-1876; Venglat et al. (2002) *PNAS* 99:4730-4735); fertilization independent endosperm (FIE) (e.g., Ohad et al. (1999)

*Plant Cell* 11:407-415), and the like, the disclosures of which are herein incorporated by reference. The combinations generated can also include multiple copies of any one of the polynucleotides of interest. The combinations may have any combination of up-regulating and down-regulating expression of the combined polynucleotides. The combinations may or may not be combined on one construct for transformation of the host cell, and therefore may be provided sequentially or simultaneously. The host cell may be a wild-type or mutant cell, in a normal or aneuploid state.

II. Altering the Oil Content in Plants

The present invention provides a method for altering the oil content of a plant. By "altering the oil phenotype" of a plant is intended any modulation (increase or decrease) in the overall level of oil in the plant or plant part (i.e., seed) when compared to a control plant. The altered oil phenotype can comprise any statistically significant increase or decrease in oil when compared to a control plant. For example, altering the oil phenotype can comprise either an increase or a decrease in overall oil content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, or greater when compared to a control plant or plant part that has not been transformed with the ODP2 sequence of the invention. Alternatively, the alteration in oil phenotype can include about a 0.5 fold, 1 fold, 2 fold, 4 fold, 8 fold, 16 fold, or 32 fold increase in overall oil phenotype in the plant or plant part when compared to a control plant that has not been transformed with the ODP2 sequence.

It is further recognized that the alteration in the oil phenotype need not be an overall increase/decrease in oil content, but also includes a change in the ratio of various components of the plant oil (i.e., a change in the ratio of any of the various fatty acids that compose the plant oil). For example, the ratio of various fatty acids such as linoleic acid, oleic acid, palmitic acid, stearic acid, myristic acid, linolenic acid, lauric acid, and the like, could be altered and thereby change the oil phenotype of the plant or plant part when compared to a control plant lacking the ODP2 sequence of the invention.

The method for altering the oil phenotype of a plant comprises providing an ODP2 sequence of the invention. An ODP2 polypeptide can be provided by introducing the polypeptide into the plant, and thereby modifying the oil content of the plant or plant part. Alternatively, an OPD2 nucleotide sequence can be provided by introducing into the plant a heterologous polynucleotide comprising an ODP2 nucleotide sequence of the invention, expressing the ODP2 sequence, and thereby modifying the oil content of the plant. In yet other embodiments, the ODP2 nucleotide construct introduced into the plant is stably incorporated into the genome of the plant.

Methods for determining if the oil phenotype of the plant has been altered are known in the art. For example, the oil phenotype can be determined using NMR. Briefly, data for plant or plant part oil percentage, total plant or plant part oil, and plant or plant part weight are collected and analyzed by NMR. If changes from the control (a plant not transformed with ODP2) are observed above base-line, a PCR co-segregation analysis can be performed to determine if the changes are correlated with the presence of the ODP2 sequence. In specific embodiments, the plant part is an embryo. Alternatively, fatty acid content and composition can be determined by gas chromatography (GC). See, for example, WO 03/001902, herein incorporated by reference.

As discussed above, one of skill will recognize the appropriate promoter to use to alter the oil content of the plant in the desired manner. Exemplary promoters for this embodiment include the ubiquitin promoter (Christensen et al. (1992) *Plant Molecular Biology* 18:675-680), a lipid transfer protein (LTP) promoter (U.S. Pat. No. 5,525,716), a gamma-zein promoter (GZP) (Boronat et al. (1986) *Plant Sciences* 47:95-102), and the oleosin promoter (WO 00/28058), the lec1 promoter (WO 02/42424), and the Zm-ODP2 promoter (U.S. Provisional Application No 60/541,171, entitled "ODP2 Promoter and Methods of Use" filed on Feb. 2, 2004, herein incorporated by reference in its entirety.

In specific embodiments, the oil content of the plant is decreased upon increasing level/activity of the ODP2 polypeptide in a plant. A decreased oil content finds use in the wet milling industry and in the ethanol dry grind industry. In the dry grind process, raw corn is ground, mixed with water, cooked, saccharified, fermented, and then distilled to make ethanol. The process also recovers distillers dried gains with solubles that can be used in feed products. Various methods of ethanol dry grind are known in the art. See, for example, U.S. Pat. Nos. 6,592,921, 6,433,146, Taylor et al. (2003) *Applied Biochemistry and Biotechnology* 104:141-148; Taylor et al. (2000) *Biotechnol Prog.* 16:541-7, and Taylor et al. (2001) *Appl Biocehm Biotechnol* 94:41-9.

In the wet milling process, the purpose is to fractionate the kernel and isolate chemical constituents of economic value into their component parts. The process allows for the fractionation of starch into a highly purified form, as well as, for the isolation in crude forms of other material including, for example, unrefined oil, or as a wide mix of materials which commonly receive little to no additional processing beyond drying. Hence, in the wet milling process grain is softened by steeping and cracked by grinding to release the germ from the kernels. The germ is separated from the heavier density mixture of starch, hulls and fiber by "floating" the germ segments free of the other substances in a centrifugation process. This allows a clean separation of the oil-bearing fraction of the grain from tissue fragments that contain the bulk of the starch. Since it is not economical to extract oil on a small scale, many wet milling plants ship their germ to large, centralized oil production facilities. Oil is expelled or extracted with solvents from dried germs and the remaining germ meal is commonly mixed into corn gluten feed (CGF), a coproduct of wet milling. Hence, starch contained within the germ is not recovered as such in the wet milling process and is channeled to CGF. See, for example, Anderson et al. (1982) *"The Corn Milling Industry"*; *CRC Handbook of Processing and Utilization in Agriculture*, A. Wolff, Boca Raton, Fla., CRC Press., Inc., Vol. 11, Part 1, *Plant Products:* 31-61 and Eckhoff (Jun. 24-26, 1992) *Proceedings of the 4th Corn Utilization Conference*, St. Louis, Mo., printed by the National Corn Growers Association, CIBA-GEIGY Seed Division, and the USDA, both of which are herein incorporated by reference.

In other embodiments, the oil content of the plant or plant part is increased. Plants containing an increase in oil content can be used in a variety of applications. For example, high oil plants have an improved food efficiency, which results in greater amounts of energy in the germ. In addition, high oil plants can have an increase in lysine levels, reduced dust during grinding, and improved feed product when compared with normal plants. High oil content in seeds also yields greater amounts of oil when grain is processed into oil and provides economic advantages to starch wet milling.

Accordingly, the present invention further provides plants having an altered oil phenotype when compared to the oil phenotype of a control plant. In specific embodiments, the altered oil phenotype is in a grain. In some embodiments, the plant of the invention has an increased level/activity of the ODP2 polypeptide of the invention and has a decreased oil content. In other embodiments, such plants have stably incorporated into their genome a heterologous nucleic acid molecule comprising an ODP2 nucleotide sequence of the invention operably linked to a promoter that drives expression in the plant cell.

III. Altering Starch Production in Plants

The present invention provides a method for modifying the starch production of a plant. By "starch" is intended a polymer of glucose and normally comprises amylose, amylopectin or a mixture of these two polymer types. Functionally analogous chemical compounds, also included within the definition of starch, include phytoglycogen (which occurs in select types of corn) and water soluble polysaccharides (glucose polymers lacking the crystalline structure of starch granules).

By "modify starch production" of a plant is intended any modulation (increase or decrease) in the overall level of starch in the plant or plant part (i.e., seed, grain, etc.) when compared to a control plant. The modification in starch production can comprise any statistically significant increase or decrease in starch levels when compared to a control plant. For example, modifying starch production can comprise either an increase or a decrease in overall starch content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, 110%, 125% or greater when compared to a control plant or plant part that has not been transformed with the ODP2 sequence of the invention. Alternatively, the modification of starch production can include about a 0.2 fold, 0.5 fold, 1 fold, 2 fold, 4 fold, 8 fold, 16 fold, or 32 fold increase in overall starch content in the plant or plant part when compared to a control plant that has not been transformed with the ODP2 sequence.

The method for modifying the starch production in a plant comprises providing an ODP2 sequence of the invention. An ODP2 polypeptide can be provided by introducing the polypeptide into the plant, and thereby modifying the starch production of the plant or plant part. Alternatively, an ODP2 nucleotide sequence can be provided by introducing into the plant a heterologous polynucleotide comprising an ODP2 nucleotide sequence of the invention, expressing the ODP2 sequence, and thereby modifying the starch production of the plant. In yet other embodiments, the ODP2 nucleotide construct introduced into the plant is stably incorporated into the genome of the plant.

Methods for determining if the starch production in the plant or plant part has been altered are known in the art. For example, total starch measurement can be performed as outlined in McCleary et al. (1994) *Journal of Cereal Science* 20:51-58, McCleary et al. (1997) *J. Assoc. Off. Anal. Chem* 80:571-579, and McCleary et al. (2002) *J. AOAC International* 85:1103-1111, each of which is herein incorporated by reference.

As discussed above, one of skill will recognize the appropriate promoter to use to modify starch production in a plant in the desired manner. Exemplary promoters for this embodiment include the ubiquitin promoter (Christensen et al. (1992) *Plant Molecular Biology* 18:675-680), a lipid transfer protein (LTP) promoter (U.S. Pat. No. 5,525,716), a gamma-zein promoter (GZP) (Boronat et al. (1986) *Plant Sciences* 47:95-102), and the oleosin promoter (WO 00/28058), the lec1 promoter (WO 02/42424), and the Zm-ODP2 promoter (U.S. Provisional Application No. 60/541,171, entitled "ODP2 Promoter and Methods of Use" filed on Feb. 2, 2004.

In specific embodiments, the modification of starch production results in an increase in starch content in the plant or plant part upon increasing level/activity of the ODP2 polypeptide in a plant. An increased starch content finds use in the in the wet milling industry and in the ethanol dry grind industry. In other embodiments, the starch production results in a decrease in starch content in the plant or plant part upon decreasing the level/activity of the ODP2 polypeptide in the plant.

Accordingly, the present invention further provides plants or plant parts having modified starch production when compared to the starch production of a control plant or plant part. In specific embodiments, the plant having the altered starch production is a grain. In some embodiments, the plant of the invention has an increased level/activity of the ODP2 polypeptide of the invention and has an increase in starch accumulation. In other embodiments, such plants have stably incorporated into their genome a heterologous nucleic acid molecule comprising an ODP2 nucleotide sequence of the invention operably linked to a promoter that drives expression in the plant cell.

IV. Modifying the Regenerative Capacity of Plants

The present invention further provides methods to modify the regenerative capacity of a plant. As used herein "regeneration" refers to a morphogenic response that results in the production of new tissues, organs, embryos, whole plants or parts of whole plants that are derived from a single cell or a group of cells. Regeneration may proceed indirectly via a callus phase or directly, without an intervening callus phase. "Regenerative capacity" refers to the ability of a plant cell to undergo regeneration.

In this embodiment, the method of modifying the regenerative capacity of a plant comprises providing an ODP2 sequence of the invention. In one embodiment, the regenerative capcity of the plant is modified by increasing the level and/or activity of an ODP2 polypeptide. The ODP2 sequence can be provided by introducing an ODP2 polypeptide into the plant, and thereby modifying the regenerative capacity of said plant. Alternatively, an ODP2 nucleotide sequence can be provided by introducing into the plant a heterologous polynucleotide comprising an ODP2 polynucleotide of the invention, expressing the ODP2 sequence, and thereby modifying the regenerative capacity of the plant. In yet other embodiments, the ODP2 nucleotide construct introduced into the plant is stably incorporated into the genome of the plant.

It is further recognized that providing the ODP2 sequences may be used to enhance the regenerative capacity of plant tissues both in vitro and in vivo and thereby stimulating cell proliferation and/or differentiation. In one embodiment, a method of initiating meristem formation is provided.

As discussed in further detail below, the promoter used to express the ODP2 sequence of the invention will depend, in part, on the target tissue used for regeneration. Various promoters of interest include constitutive promoters, tissue-preferred promoters, developmentally regulated promoters, and chemically-inducible systems. Various promoters that regulate ovule and embryo expression, nucellus expression, and inner integument expression are discussed in further detail below.

The ODP2 sequences of the invention also will be useful for inducing apomixis in plants. In specific embodiments, increasing the level and/or activity of the ODP2 polypeptide induces apomixis. Apomixis and methods of conferring apomixis into plants are discussed in U.S. Pat. Nos. 5,710,367; 5,811,636; 6,028,185; 6,229,064; and 6,239,327 as well as WO 00/24914, all of which are incorporated herein by reference. Reproduction in plants is ordinarily classified as sexual or asexual. The term apomixis is generally accepted as the replacement of sexual reproduction by various forms of asexual reproduction (Rieger et al. (1976) *Glossary of Genetics and Cytogenetics*, Springer-Verlag, New York, N.Y.). In general, the initiation of cell proliferation in the embryo and endosperm are uncoupled from fertilization. Apomixis is a genetically controlled method of reproduction in plants where the embryo is formed without the union of an egg and a sperm. There are three basic types of apomictic reproduction: 1) apospory-embryo develops from a chromosomally unreduced egg in an embryo sac derived from a somatic cell in the nucellus; 2) diplospory-embryo develops from an unreduced egg in an embryo sac derived from the megaspore mother cell; and, 3) adventitious embryony-embryo develops directly from a somatic cell. In most forms of apomixis, pseudogamy or fertilization of the polar nuclei to produce endosperm is necessary for seed viability.

These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species with good male sterility. It also provides a system for the production of hybrid seed in species, or between genotypes of the same species in which crossing between separate parent plants is impractical on a large scale.

In another embodiment, methods for producing embryogenic cells are provided. By "embryogenic cell" is intended a cell that has completed the transition from either a somatic or a gametophytic cell to a state where no further applied stimuli are necessary to produce an embryo. In this embodiment, the method comprises providing an ODP2 sequence of the invention. In one embodiment, the level and/or activity of the ODP2 polypeptide is increased and thereby allows for an increased production of embryogenic cells. In one embodiment, the ODP2 sequence is an ODP2 polypeptide which is provided by introducing the polypeptide into the plant, and thereby producing an embryogenic cell. Alternatively, an OPD2 nucleotide sequence can be provided by introducing into the plant a heterologous polynucleotide comprising an ODP2 nucleotide sequence of the invention, expressing the ODP2 sequence, and thereby producing an embryogenic cell. In yet other embodiments, the ODP2 nucleotide construct introduced into the plant is stably incorporated into the genome of the plant.

Further provided is a method for producing asexually derived embryos. As used herein, the term "asexually derived embryo" refers to an embryo that is generated in the absence of fertilization. The term is inclusive of apomitic and somatic embryos. The term "somatic embryogenesis" refers to non-zygotic embryogenesis. The method comprises introducing into a plant an ODP2 sequence of the invention and thereby producing asexually derived embryos. As discussed above, the embryo can be a somatic embryo, an adventitious embryos, or a gametophytic embryo.

Methods are also provided for an increase in the production of somatic embryos in a plant. In one embodiment, the level and/or activity of the ODP2 polypeptide is increased and thereby allowing for the production of somatic embryos. In one embodiment, an ODP2 sequence of the invention is provided. The polypeptide can be provided by introducing the polypeptide into the plant, and thereby increasing the production of somatic embryos. Alternatively, an OPD2 nucleotide sequence can be provided by introducing into the plant a heterologous polynucleotide comprising an ODP2 nucleotide sequence of the invention, expressing the ODP2 sequence, and thereby increasing the production of somatic embryos. In yet other embodiments, the ODP2 nucleotide construct introduced into the plant is stably incorporated into the genome of the plant.

The somatic embryo structures may form as individual embryos or as a cluster of structures. In specific embodiments, the plants (i.e., the root, leaf, seedling) expressing the ODP2 sequences are cultured in vitro. The embryos, non-embryogenic callus or both are transferred to appropriate media for the production of embryos or plantlets. While the somatic embryo can be formed independent of additional growth regulators, it is recognized that in some embodiments, growth regulators can be added to the media and include, but are not limited to, 2,4-D (Mordhorst et al. (1998) Genetics 149:549-563).

An increase in asexually derived embryos can be assayed by determining if embryogenesis or embryonic callus is initiated at a higher frequency from transgenic lines expressing ODP2 sequences of the invention compared to a control plant or plant part. See, for example, Boutiler et al. (2002) *The Plant Cell* 14:1737-1749, herein incorporated by reference.

It is recognized that the plant having the somatic embryo structures may form only a limited number of somatic embryo structures and then resume additional post germination growth. In other embodiments, expression of the ODP2 sequence leads to the reiteration of the embryo forming process, with the result that new embryos or cotyledons are formed continuously.

In particular embodiments, the level and/or activity of the ODP2 polypeptide will be reduced prior to the regeneration of a plant from these various embryogenic cell types. Methods for reducing the activity of the ODP2 polypeptide are discussed in detail elsewhere herein.

Embryogenesis can be induced in haploid cells, such as pollen cells, egg cells, or cells from haploid lines, to produce haploid plants. Methods of inducing embryogenesis in haploid cells comprise providing an ODP2 sequence of the invention to a plant. In one embodiment, the level and/or activity of the ODP2 polypeptide is increased and thereby allows for the induction of embryogenesis in haploid cells. An ODP2 polypeptide can be provided by introducing the polypeptide into the plant, and thereby inducing embryogenesis. Alternatively, an OPD2 nucleotide sequence can be provided by introducing into the plant a heterologous polynucleotide comprising an ODP2 nucleotide sequence of the invention, expressing the ODP2 sequence, and thereby inducing embryogenesis. In yet other embodiments, the ODP2 nucleotide construct introduced into the plant is stably incorporated into the genome of the plant.

In one embodiment, the ODP2 nucleotide sequence introduced into the plant is under the control of a tissue specific promoter that is active in a haploid cell or tissue or a promoter that is active during microspore development (such as, the maize PG47 promoter (Allen et al. (1993) *Plant J.* 3:261-71), the zm-G13 promoter (Hamilton et al. (1992) *Plant Mol Biol.* 18:211-218). In other embodiments, the ODP2 nucleotide sequence is under the control of an inducible promoter and the application of the inducer allows expression of the ODP2 sequence therein. Alternatively, the promoter used can be both inducible and tissue-preferred, giving greater control over the process. For example, the promoter can be both haploid-tissue specific and inducible. In one embodiment, the promoter is an inducible pollen-specific promoter used to induce somatic embryogenesis in pollen cells. In still other embodiments, site-specific recombination systems can be used in combination with promoters (i.e., constitutive promoters or inducible promoters) to regulate the appropriate time and level of ODP2 expression. Thus, the methods of the invention find use in promoting embryogenesis in microspore and anther cultures.

Providing the ODP2 sequence to a haploid tissue or cell results in the formation of haploid somatic embryos, which can be grown into haploid plants using standard techniques. When an inducible promoter is used (whether tissue specific or not), an optimal method comprises exposing excised transgenic tissue containing the haploid cells (e.g., pollen or ovules) to the inducer specific for the inducible promoter for a time sufficient to induce the formation of a somatic embryo, withdrawing the inducer, and growing the somatic embryo into a transgenic haploid plant in the absence of the inducer.

Diploidization of the haploid plants to form dihaploids, either spontaneously or by treatment with the appropriate chemical (e.g. colchicine) will significantly expedite the process of obtaining homozygous plants as compared to a method of conventional genetic segregation. This technology will not only be beneficial for breeding purposes but also for basic research such as studies of mutagenesis and other genetic studies, because dihaploids are truly homozygous down to the DNA level, containing two identical copies of each gene.

In yet another embodiment, adventitious embryony can be achieved by providing an ODP2 sequence of the invention to sporophytic ovule tissues such as the nucellus, the inner integuments, or other tissues lying adjacent to or in proximity to the developing embryo sac.

The ODP2 sequences of the invention may also be used as a selectable marker to recover transgenic plants. In one embodiment, the level and/or activity of the ODP2 sequence is increased. In this embodiment, a plant is transformed with the ODP2 sequences along with a nucleotide sequence of interest. Upon expression of the ODP2 sequences, the plants can be selected based on their ability to regenerate under conditions in which wild type explants are unable to. For example, the transgenic plants may be able to regenerate in the absence of growth regulators. If the ODP2 sequence and the polynucleotide of interest are carried on separate plasmids, the ODP2 sequence can be subsequently removed from transgenic plants by routine breeding methods.

One of skill in the art will recognize that a variety of promoters can be used in the various methods of the invention. Somatic or gametophytic embryos can be obtained expressing the ODP2 polypeptide under the control of constitutive promoters, tissue-preferred, developmentally regulated, or various inducible promoters including chemical induction systems (i.e., tetracycline-inducible systems, steroid inducible promoters, and ethanol-inducible promoters). Temporal and/or spatial restriction of ODP2 is optimal when recurrent embryogenesis is not a desirable trait. Promoters of interest when microspore-derived embryo production is desired include, but are not limited to, microspore/pollen expressed genes such as *NTM19* (EP 790,311), BCP1 (Xu et al. (1995) *Plant Mol. Biol.* 22:573-588, PG47 (Allen et al. (1993) *Plant J.* 3:261-71), ZmG13 (Hamilton et al. (1992) *Plant Mol. Biol.* 18:211-218), and BNM1 (Treacy et al. (1997) *Plant Mol. Biol.* 34:603-611), each reference is herein incorporated by reference. Promoters of interest when the production of somatic embryos are desired include, but are not limited to, cytokinin inducible IB6 and CK11 promoters (Brandstatter et al. (1998) *Plant Cell* 10:1009-1019). Exemplary promoters of interest when adventitious embryony, diplospory or haploid parthenogenesis of embryo sac components, include, the AtDMC1 gene (WO 98/28431), promoters that direct expression in the ovule, such as the AGL11 promoter (Rounsley et al. (1995) *Plant Cell* 10:1009-1019) and the SERK promoter (Schmidt et al. (1997) *Development* 124:2049-2062), promoters that direct expression in the nucellus such as the NUC1 promoter (WO 98/08961), promoters that regulate expression of inner integument genes such as the FBP7 promoter (Angenent et al. (1995) *Plant Cell* 7:1569-1582), microspore/pollen-preferred promoters (discussed above) and chemical induction systems. Each of these references is herein incorporated by reference.

Accordingly, the present invention further provides plants having a modified regenerative capacity, including plants that are capable of producing asexually derived embryos. In some embodiments, the plants having a modified regenerative capacity have an increased level/activity of the ODP2 polypeptide of the invention. In other embodiments, the plant comprises a heterologous ODP2 nucleotide sequence of the invention operably linked to a promoter that drives expression in the plant cell. In other embodiments, such plants have stably incorporated into their genome a heterologous nucleic acid molecule comprising an ODP2 nucleotide sequence of the invention operably linked to a promoter that drives expression in the plant cell.

In other embodiments, the OPD2 sequences of the invention can be used to modify the tolerance of a plant to abiotic stress. In one embodiment, a method is provided to increase or maintain seed set during abiotic stress episodes. During periods of stress (i.e., drought, salt, heavy metals, temperature, etc.) embryo development is often aborted. In maize, halted embryo development results in aborted kernels on the ear. Preventing this kernel loss will maintain yield. Accordingly, methods are provided to increase the stress resistance in a plant (i.e., an early developing embryo).

The method comprises providing an ODP2 sequence of the invention. The polypeptide can be provided by introducing the polypeptide into the plant, and thereby modifying the plants tolerance to abiotic stress. Alternatively, an OPD2 nucleotide sequence can be provided by introducing into the plant a heterologous polynucleotide comprising an ODP2 nucleotide sequence of the invention, expressing the ODP2 sequence, and thereby modifying the plants tolerance to abiotic stress. In yet other embodiments, the ODP2 nucleotide construct introduced into the plant is stably incorporated into the genome of the plant.

A variety of promoters can be employed in this method. In one embodiment, the ODP2 sequence is under the control of an early promoter. An early embryo is defined as the stages of embryo development including the zygote and the developing embryo up to the point where embryo maturation begins. An "early embryo promoter" is a promoter that drives expression predominately during the early stages of embryo development (i.e., before 15-18 DAP). Alternatively, the early embryo promoter can drive expression during both early and late stages. Early embryo promoters include, but are not limited to, to Lec 1 (WO 02/42424); ciml, a pollen and whole kernel specific promoter (WO 00/11177); the seed-preferred promoter end1 (WO 00/12733); and, the seed-preferred promoter end2 (WO 00/12733) and 1pt2 (U.S. Pat. No. 5,525,716). Additional promoter include, smilps, an embryo specific promoter and czl9B1 a whole kernel specific promoter. See, for example, WO 00/11177, which is herein incorporated by reference. All of these references is herein incorporated by reference.

Methods to assay for an increase in seed set during abiotic stress are known in the art. For example, plants having the ODP2 sequences of the invention can be monitored under various stress conditions and compared to controls plants (not having had the ODP2 introduced). For instance, the plant having the OPD2 sequence can be subjected to various degrees of stress during flowering and seed set. Under identical conditions, the genetically modified plant having the ODP2 sequences will have a higher number of developing kernels than a wild type (non-transformed) plant.

Accordingly, the present invention further provides plants having increased yield or maintaining their yield during periods of abiotic stress (i.e. drought, salt, heavy metals, temperature, etc). In some embodiments, the plants having an increased or maintained yield during abiotic stress have an increased level/activity of the ODP2 polypeptide of the invention. In other embodiments, the plant comprises a heterologous ODP2 nucleotide sequence of the invention operably linked to a promoter that drives expression in the plant cell. In other embodiments, such plants have stably incorporated into their genome a heterologous nucleic acid molecule comprising an ODP2 nucleotide sequence of the invention operably linked to a promoter that drives expression in the plant cell.

V. Modifying the Transformation Efficiency in Plants

The present invention provides novel methods for transformation and for increasing transformation frequencies. As used herein "responsive target plant cell" is a plant cell that exhibits increased transformation efficiency after the introduction of the ODP2 sequences of the invention when compared to a control plant or plant part. The increase in transformation efficiency can comprise any statistically significant increase when compared to a control plant. For example, an increase in transformation efficiency can comprises about 0.2%, 0.5%, 5%, 10%, 15%, 20%, 25%, 30%, 35%, 40%, 45%, 50%, 55%, 60%, 65%, 70%, 75%, 80%, 85%, 90%, 95%, 120%, 125% or greater increase when compared to a control plant or plant part. Alternatively, the increase in transformation efficiency can include about a 0.2 fold, 0.5 fold, 1 fold, 2 fold, 4 fold, 8 fold, 16 fold, or 32 fold or greater increase in transformation efficiency in the plant when compared to a control plant or plant part.

Many maize genotypes, and in particular elite germplasm developed in commercial breeding programs, are recalcitrant to in vitro culture and transformation. Such genotypes do not produce an appropriate embryogenic or organogenic culture response on culture media developed to elicit such responses from typically suitable explants such as immature embryos. Furthermore, when exogenous DNA is introduced into these immature embryos (for example, using particle bombardment or *Agrobacterium*), no transgenic events are recovered after selection (or so few events are recovered as to make transformation of such a genotype impractical). When the ODP2 gene is expressed (either transiently or stably) in immature embryos of such genotypes, vigorously growing transgenic events can be readily recovered.

Thus, the present invention finds use in increasing the transformation of a recalcitrant plant or explants. As used herein "recalcitrant plant or explant" means a plant or explant that is more difficult to transform than model systems. In maize such a model system is High type-II maize. Elite maize inbreds are typically recalcitrant. In soybeans such model systems are Peking or Jack.

In one embodiment of the invention, a method for increasing the transformation efficiency in a plant is provided. The method comprises providing an ODP2 sequence of the invention. An ODP2 polypeptide can be provided by introducing the polypeptide into the plant, and thereby increasing the transformation efficiency of the plant. Alternatively, an OPD2 nucleotide sequence can be provided by introducing into the plant a heterologous polynucleotide comprising an ODP2 nucleotide sequence of the invention, expressing the ODP2 sequence, and thereby increasing the transformation efficiency of the plant. In yet other embodiments, the ODP2 nucleotide construct introduced into the plant is stably incorporated into the genome of the plant. Through the introduction of an ODP2 into a recalcitrant plant and producing a positive influence on transformation, the methods of the invention provide the potential to increase the overall genetic transformation throughput of various recalcitrant germplasm.

Accordingly, the present invention further provides plants having increased transformation efficiencies when compared to the transformation efficiency of a control plant. In some embodiments, the plants having increased transformation efficiencies have an increased level/activity of the ODP2 polypeptide of the invention. In other embodiments, the plant comprises a heterologous ODP2 nucleotide sequence of the invention operably linked to a promoter that drives expression in the plant cell. In other embodiments, such plants have stably incorporated into their genome a heterologous nucleic acid molecule comprising an ODP2 nucleotide sequence of the invention operably linked to a promoter that drives expression in the plant cell.

In another embodiment, a method of transforming in a plant is provided. The method comprises providing a target plant, where the target plant had been provided an ODP2 sequence of the invention. In some embodiments, the OPD2 nucleotide sequence is provided by introducing into the plant a heterologous polynucleotide comprising an ODP2 nucleotide sequence of the invention, expressing the ODP2 sequence. In yet other embodiments, the ODP2 nucleotide construct introduced into the target plant is stably incorporated into the genome of the plant. The target plant is transformed with a polynucleotide of interest. It is recognized that the target plant having had the ODP2 sequence introduced (referred to herein as a "modified target plant"), can be grown under conditions to produce at least one cell division to produce a progeny cell expressing the ODP2 sequence prior to transformation with one or more polynucleotides of interest. As used herein "re-transformation" refers to the transformation of a modified cell.

The modified target cells having been provided the ODP2 sequence can be obtained from T0 transgenic cultures, regenerated plants or progeny whether grown in vivo or in vitro so long as they exhibit stimulated growth compared to a corresponding cell that does not contain the modification. This includes but is not limited to transformed callus, tissue culture, regenerated T0 plants or plant parts such as immature embryos or any subsequent progeny of T0 regenerated plants or plant parts.

Once the target cell is provided with the ODP2 nucleotide sequence it is re-transformed with at least one gene of interest. The transformed cell can be from transformed callus, transformed embryo, T0 regenerated plants or its parts, progeny of T0 plants or parts thereof as long as the ODP2 sequence of the invention is stably incorporated into the genome.

Methods to determine transformation efficiencies or the successful transformation of the polynucleotide of interest are known in the art. For example, transgenic plants expressing a selectable marker can be screened for transmission of the gene(s) of interest using, for example, chemical selection, phenotype screening standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes.

The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Seeds derived from plants regenerated from re-transformed plant cells, plant parts or plant tissues, or progeny derived from the regenerated plants, may be used directly as feed or food, or further processing may occur.

Any polynucleotide of interest can be used in the methods of the invention. Various changes in phenotype are of interest including modifying the fatty acid composition in a plant, altering the amino acid content, starch content, or carbohydrate content of a plant, altering a plant's pathogen defense mechanism, affecting kernel size, sucrose loading, and the like. The gene of interest may also be involved in regulating the influx of nutrients, and in regulating expression of phytate genes particularly to lower phytate levels in the seed. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261: 6279; Kirihara et al. (1988) *Gene* 71:359; both of which are herein incorporated by reference); and rice (Musumura et al. (1989) *Plant Mol. Biol.* 12:123, herein incorporated by reference) could be used. Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and, the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The following examples are offered by way of illustration and not by way of limitation.

EXPERIMENTAL

Example 1. Cloning of ZM-ODP2

The protein encoded by maize EST clone cpf1c.pk009.f4 was initially identified as the homologue of a rice putative ovule development protein (BAB89946). The EST clone was subjected to full-insert sequencing. Comparison of rice BAB89946 and the protein sequence encoded by the longest open reading frame (ORF) from cpflc.pk009.f4 suggests that this clone may have an internal deletion which causes premature termination of the protein by at least 120 amino acids. A genomic fragment encompassing the potential deletion was amplified by PCR using DNA isolated from Hi II callus. Sequencing results confirm the presence of an extra 146 base pairs in the genomic fragment. When added to cDNA clone cpflc.pk009.f4, this 146-bp can be read through in the same reading frame and the ORF is extended to encode a protein very similar to BAB89946 in length.

The full-length Zm-ODP2 (SEQ ID NO:1) used in the transformation was created by combining the 5' end of cDNA clone cpflc.pk009.f4 and part of the genomic clone from Hi II callus that contains the missing 146-bp. More specifically, a 1790-bp EcoRI-SbfI fragment from cpflc.pk009.f4 and a 582-bp SbfI-SalI genomic fragment were ligated into pBluescript II KS+digested with EcoRI and SalI to form PHP20430.

The full-length Zm-ODP2 sequence is 2260 nucleotides in length. The open reading frame is 2133 nucleotides in length and starts at nucleotide 128 and ends at nucleotide 2260 of SEQ ID NO:1. The nucleotide sequence of the Zm-ODP2 open reading frame is set forth in SEQ ID NO:3. The 710 amino acid sequence encoded by the Zm-ODP2 sequence is set forth in SEQ ID NO:2.

Example 2. Sequence Analysis of Zm-ODP2

The ZM-ODP2 sequence of the invention was analyzed for conserved domains. FIGS. 1A-1D show an alignment of the amino acid sequence of Zm-ODP2 (SEQ ID NO:2) with various polypeptides sharing sequence similarity to the Zm-ODP2 sequence. Specifically, Zm-ODP2 ODP2 shares over its full-length about 65.4% sequence identity and 72.7% sequence similarity with OsAnt (Accession No. BAB89946; SEQ ID NO:26). Zm-ODP2 shares over its full-length about 57.1% sequence identity and about 62.3% sequence similarity to OSBNM (Accession No. AAL47205; SEQ ID NO:27). Zm-ODP2 shares over its full-length about 42% sequence identity and about 53.2% sequence similarity to OSODP (Accession No. CAE05555; SEQ ID NO:29). Zm-ODP2 shares over its full-length about 37% sequence identity and about 45% sequence similarity to BnBBM2 (Accession No. AAM33801; SEQ ID NO:33). Zm-ODP2 shares over its full-length about 38% sequence identity and about 47% sequence similarity to BnBBM1 (AAM33800; SEQ ID NO:32). Zm-ODP2 shares over its full-length about 38.1% sequence identity and about 46.3% sequence similarity to ATBBM (Accession No. AAM33803; SEQ ID NO:31). Zm-ODP2 shares over its full-length about 40% sequence identity and about 43% sequence similarity to AtODP (Accession No. AAD30633; SEQ ID NO:36). Zm-ODP2 shares over its full-length about 35.6% sequence identity and about 50% sequence similarity to ATODP (Accession No. NP_175530; SEQ ID NO:34). Zm-ODP2 shares over its full-length about 34.9% sequence identity and about 44.6% sequence similarity to AtODP (Accession No. BAB02492; SEQ ID NO:35). Zm-ODP2 shares over its full-length about 38.4% sequence identity and about 46% sequence similarity to AtODP (NP_197245; SEQ ID NO:30). A consensus sequence for all 11 aligned polypeptides is also provided (SEQ ID NO:37).

All 11 proteins present in the alignment have two AP2 (APETALA2; pfam00847.8) domains. Using the amino acid numbering of the Zm-ODP2, the first AP2 domain is from about amino acid 273 to about 343 and the second AP2 domain is from about amino acid 375 to about 437. The consensus sequence for the APETALA2 PFAM family is SKYRGVRQRPWGKWVAEIRDPRKGTRVWLGTFD-TAEEAARAYDVAALKLRGPSAVLN FPNEL (SEQ ID NO: 38).

Example 3. Variants of Zm-ODP2

A. Variant Nucleotide Sequences of Zm-ODP2 (SEQ ID NO:1) That Do Not Alter the Encoded Amino Acid Sequence The Zm-ODP2 nucleotide sequence set forth in SEQ ID NO:1 was used to generate 6 variant nucleotide sequences having the nucleotide sequence of the open reading frame with about 70.6%, 76.1%, 81.2%, 86.3%, 92.1%, and 97.1% nucleotide sequence identity when compared to the starting unaltered ORF nucleotide sequence of SEQ ID NO:1. These functional variants were generated using a standard codon table. While the nucleotide sequence of the variant was altered, the amino acid sequence encoded by the open reading frame did not change.

The variants of Zm-ODP2 using this method are set forth in SEQ ID NOS:6-11. Specifically, SEQ ID NO: 6 shares about 97.1% nucleic acid sequence identity to the Zm-ODP2 sequence of SEQ ID NO:1; SEQ ID NO: 7 shares about 92.1% nucleic acid sequence identity to SEQ ID NO:1, SEQ ID NO:8 shares about 86.3% nucleic acid sequence identity to SEQ ID NO:1; SEQ ID NO:9 shares about 81.2% nucleic acid sequence identity to SEQ ID NO:1; SEQ ID NO:10 shares about 76.1% nucleic acid sequence identity to SEQ ID NO:1; and SEQ ID NO:11 shares about 70.6% nucleic acid sequence identity to SEQ ID NO:1.

B. Variant Amino Acid Sequences of Zm-ODP2

Variant amino acid sequences of Zm-ODP2 were generated. In this example, one amino acid was altered. Specifically, the open reading frame set forth in SEQ ID NO:3 was reviewed to determined the appropriate amino acid alteration. The selection of the amino acid to change was made by consulting the protein alignment (with the other orthologs and other gene family members from various species). See FIGS. 1A-1D. An amino acid was selected that was deemed not to be under high selection pressure (not highly conserved) and which could be rather easily substituted by an amino acid with similar chemical characteristics (i.e., similar functional side-chain). Using the protein alignment set forth in FIGS. 1A-1D and focusing at the N-terminus (amino acids 1-50), the serine at amino acid position 37 (shaded) was changed to a threonine, which is chemically similar. Thus, the "TCC" serine codon in the nucleic acid sequence is changed to an "ACC" codon for threonine. The Zm-ODP2 sequence having the single change from "TCC" to "ACC" is set forth in SEQ ID NO:12.

Once the targeted amino acid was identified, the procedure outlined in Example 3A was followed. Variants having about 70.4% (SEQ ID NO:18), 75.9% (SEQ ID NO:17), 81.5% (SEQ ID NO:16), 86.6% (SEQ ID NO:15), 91.9% (SEQ ID NO:14), and 97.3% (SEQ ID NO:13) nucleic acid sequence identity to SEQ ID NO:3 were generated using this method. SEQ ID NOS: 13-18 all encode the same polypeptide, which is set forth in SEQ ID NO: 19.

C. Additional Variant Amino Acid Sequences of Zm-ODP2

In this example, artificial protein sequences were created at a narrower interval range (82.5%, 87.5%, 92.5%, and 97.5% identity relative to the reference protein sequence). This latter effort requires identifying conserved and variable regions from the alignment set forth in FIGS. 1A-1D and then the judicious application of an amino acid substitutions table. These parts will be discussed in more detail below.

Largely, the determination of which amino acid sequences were altered was made based on the conserved regions among AP2 protein or among the other ODP-like genes. See FIGS. 1A-1D. Based on the sequence alignment, the various regions of the Zm-ODP2 that can likely be altered are represented in lower case letters, while the conserved regions are represented by capital letters. It is recognized that conservative substitutions can be made in the conserved regions below without altering function. In addition, one of skill will understand that functional variants of the ODP2 sequence of the invention can have minor non-conserved amino acid alterations in the conserved domain. This sequence is set forth in SEQ ID NO:2.

MAtvNNWLAFSLSPqelppsqttdstlisaatADhvsGDVCFNipqdwsmrgselsalvaepkle dflggisfseqhhkancnmipstsstvcyassgastgyhhqlyhqptssalhfsdsvmvassagv hdggamlsaaaangvagaasanGGGIGLSMIKNWLRSQPapmqprvaaaegaqglslsmnmagtt qgaagmpllagerarapesvstsaqggavvvtapkedsggsgvagalvavstdtggsggasadnt aRKTVDTFGQRTSIYRGVTRHRWTGRYEAHLWDNSCRREGQTRKGRQVYLGGYDKEEKAARAYDL

AALKYWGATTTTNFPVSNYEKELEDMKHMTRQEFVASLRRKSSGFSRGASIYRGVTRHHQHGRWQ

ARIGRVAGNKDLYLGTFSTQEEAAEAYDIAAIKFRGLNAVTNFDMSRYDVKSILDSSALPIGSAA

KRLKEAEAaasaqhhhagvvsydvgriasqlgdggalaaaygahyhgaawptiafqpgaastgly hpyaqqpmrgggwckqeqdhaviaaahslqdlhhlnlgaagahdffsagqqaaaaamhglgsids aslehSTGSNSVVYNGGvgdsngasavgGSGGGYmmpmsaagatttsamvsheqvharaydeakq aaqmGYESYLVnaennqggrmsawgtvvsaaaaaaassndnmaaDVGHGGAQLFSVWNDT The conserved regions are found between about amino acid 1-2; 5-14; 33-34; 38-43; 153-169; 262-463; 591-602; 614-619; 655-661; and 695-710 of SEQ ID NO: 2. The non-conserved regions are from about amino acids 3-4; 15-32; 35-37; 44-152; 170-261; 464-590; 603-613; 620-654; and 662-694 of SEQ ID NO: 2.

The goal was to create four artificial protein sequences that are different from the original in the intervals of 80-85%, 85-90%, 90-95%, and 95-100% identity. Midpoints of these intervals were targeted, with liberal latitude of plus or minus 1%, for example. The amino acids substitutions will be effected by a custom Perl script. The substitution table is provided below in Table 1.

TABLE 1

| Substitution Table | | | |
|---|---|---|---|
| Amino Acid | Strongly Similar and Optimal Substitution | Rank of Order to Change | Comment |
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |

TABLE 1-continued Substitution Table

| Amino Acid | Strongly Similar and Optimal Substitution | Rank of Order to Change | Comment |
|---|---|---|---|
| S | T | 10 | |
| T | S | 11 | |

TABLE 2-continued

Summary of the ODP2 sequences and exemplary variants thereof (SEQ ID NOS 1-25)

| SEQ ID NO | Nucleotide or Amino Acid | Description of Sequence |
|---|---|---|
| 22 | Amino acid | Variant of Zm-ODP2 having 87.3% amino acid sequence identity to SEQ ID NO: 2 (Zm-ODP2). |
| 23 | Amino acid | Variant of Zm-ODP2 having 82.4% amino acid sequence identity to SEQ ID NO: 2 (Zm-ODP2). |
| 24 | Amino acid | Consensus sequence of FIGS. 2A-2B. |

Example 4. *Agrobacterium*-Mediated Transformation

For *Agrobacterium*-mediated transformation of maize with a plasmid containing the Zm-ODP2 operably linked to an oleosin promoter and the selectable marker gene PAT, optimally the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the ODP2 sequence to at least one cell of at least one of the immature embryos (step 1: the infection step). In this step the immature embryos are optimally immersed in an *Agrobacterium* suspension for the initiation of inoculation. The embryos are co-cultured for a time with the *Agrobacterium* (step 2: the co-cultivation step). Optimally the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Optimally the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Optimally, the immature embryos are cultured on solid medium with a selective agent resulting in the selective growth of transformed cells. The callus is then regenerated into plants (step 5: the regeneration step), and optimally calli grown on selective medium are cultured on solid medium to regenerate the plants.

Example 5. Altering Oil Content and Starch Content of Maize

The full length ODP2 sequence described in Example 1, was used for construction of the oleosin driven expression cassette: OLE PRO::ZM-ODP2::NOS TERM. This cassette was inserted into a final transformation plasmid using standard protocols. The final transformation vector contains OLE PRO::ZM-ODP2::NOS TERM and MO-PAT selection marker is transformed into High type-II maize/PHR03 via *Agrobacterium* transformation. Methods of *Agrobacterium* transformation are outlined in Example 4.

Transgenic events are recovered and advanced to the greenhouse. The plants are self-pollinated. At maturity, ears are collected and a portion of seeds (typically 20 kernels from each ear) dissected to separate the embryo from the endosperm. Dissected seeds are dried down in a lyophilizer overnight. The amount of oil in each embryo is determined using NMR. Data for embryo oil %, total embryo oil and embryo weight are collected and analyzed. If changes from High type-II maize/PHR03 baseline are observed, a PCR co-segregation analysis is performed to determine if the changes are correlated with the presence of transgene (ZM-ODP2).

In addition, germs are also isolated from mature kernels for determination of starch and oil concentrations of the seed part. Individual dry seed are soaked overnight at 4° C. in 1 mL of solution containing 20 mM acetate (pH 6.5) and 10 mM mercuric chloride. (Adkins et al. (1966) *Starch* 7: 213-218). Intact germ is dissected from the seed, dried by lyophilization and recorded for dry weight. Individual germ is ground for 10 sec in a Silamet amalgam mixer and transferred with hexane washing into a microcentrifuge tube. The tissue is extracted by stirring with 1 mL of hexane 3×60 min and centrifuged after each extraction period. The supernatant of extractions is collected and placed into a preweighed aluminum pan. After evaporation of hexane from the weigh pans in a fumehood, final traces of solvent are removed in a forced draft oven at 105° C. for 15 minutes. Cooled weigh pans are reweighed to determine the total weight of oil extracted from the germ. The meal remaining after oil extraction is twice washed with water and centrifugation (10 min; 1,000×g) and analyzed for starch by a modified procedure for total starch measurement (McCleary et al. (1994) *Journal of Cereal Science* 20: 51-58). Free sugars are removed by extraction with 80% ethanol and the starch dissolved in 90% dimethylsulfoxide. Heat stable α-amylase and high purity amyloglucosidase (very low in β-glucanse activities) are used to degrade the starch to monomeric carbohydrate. The resulting glucose will be quantitated according to (Jones et al. (1977) *Plant Physiol.* 60: 379-383) with modification to a microplate format.

Example 6. Placing ODP2 Sequence Under the Control of a Tissue-Preferred Promoter The ODP2 gene can be placed under control of an inducible expression system, as described in Zuo et al. (2000) *Plant J* 24:265-273 and in U.S. Patent Application Publication No. US 2003/0082813 A1, the entire contents of which are herein incorporated by reference. The G10-90 promoter in the XVE vector can be replaced with a tissue-preferred promoter (e.g. a pollen-, root-stem- or leaf-specific promoter). A variety of tissue-preferred promoters are well known to those of skill in the art. Because expression of a transgene is activated by the chimeric XVE gene which is controlled by a tissue-preferred promoter in this Example, the $O^{lexA}$-46 promoter controlling the ODP2 transgene is therefore tissue-preferred in an inducer-dependent manner. This means that ODP2 will be induced only in the presence of an inducer and only in the specific tissue corresponding to the tissue specific promoter. Appropriate tissues or cell types, can then be collected from the transgenic plants and used for induction of somatic embryos and regeneration of plants.

Particularly when pollen derived from transgenic plants carrying a pollen-specific promoter-XVE/O$^{lexA}$-46-ODP2 vector is used, progeny plants generated from pollen-derived somatic embryos should be haploid instead of diploid (see, e.g., Twell et al. (1989) *Mol. Gen. Genetics* 217:240-245 and Twell et al. (1990) *Development* 109:705-714 for pollen-specific promoters). In this embodiment of the invention, a transgenic plant having in its genome a ODP2 gene under the control of an inducible, pollen-specific promoter would not normally express the gene. Pollen from such a plant can be cultured in the presence of the inducer until somatic embryogenesis occurs, after which the inducer is removed and the haploid embryos are permitted to develop into haploid clones according to standard techniques.

Example 7. Generating an Apomictic Plant

Apomixis can be induced by introducing ODP2 into a plant cell in such a manner that the ODP2 gene is expressed in the appropriate tissues (e.g., nucellus tissue). This can be by means of, but is not limited to, placing the ODP2 gene under the control of a tissue-preferred promoter (e.g., a nucellus-specific promoter), an inducible promoter, or a promoter that is both inducible and tissue-preferred. Inducing expression of the ODP2 gene, e.g. in the nucellus, produces fertilization-independent embryo formation leading to an apomictic plant. This plant may then be used to establish a true-breeding plant line. Additionally, the vector utilized to transfer ODP2 into the plant cell can include any other desired heterologous gene in addition to ODP2, including but not limited to, a marker gene or a gene to confer a desirable trait upon the plant, e.g., a gene resulting in larger plants, faster growth, resistance to stress, etc. This would lead to the development of an apomictic line with the desired trait.

In a variation of the scheme, plant expression cassettes, including but not limited to monocot or dicot expression cassettes, directing ODP2 expression to the inner integument or nucellus can easily be constructed. An expression cassette directing expression of the ODP2 DNA sequences to the nucellus can be made using the barley Nuc1 promoter (Doan et al. (1996) *Plant Mol Biol.* 2:276-284). Such an expression can be used for plant transformation. Other genes which confer desirable traits can also be included in the cassette.

It is anticipated that transgenic plants carrying the expression cassette will then be capable of producing de novo embryos from ODP2 expressing nucellar cells. In the case of maize, this is complemented by pollinating the ears to promote normal central cell fertilization and endosperm development. In another variation of this scheme, Nuc1: ODP2 transformations could be done using a fie (fertility-independent endosperm)-null genetic background which would promote both de novo embryo development and endosperm development without fertilization (Ohad et al. (1999) *The Plant Cell* 11:407-416). Upon microscopic examination of the developing embryos it will be apparent that apomixis has occurred by the presence of embryos budding off the nucellus. In yet another variation of this scheme the ODP2 DNA sequences could be delivered as described above into a homozygous zygotic-embryo-lethal genotype. Only the adventive embryos produced from somatic nucellus tissue would develop in the seed.

Example 8. Transformation and Regeneration of Maize Embryos

Immature maize embryos from greenhouse donor plants are bombarded with a plasmid containing the ODP2 sequence of the invention operably linked to a promoter. This could be a weak promoter such as nos, a tissue-specific promoter, such as globulin-1, an inducible promoter such as In2, or a strong promoter such as ubiquitin plus a plasmid containing the selectable marker gene PAT (Wohlleben et al. (1988) *Gene* 70:25-37) that confers resistance to the herbicide Bialaphos. Transformation is performed as follows.

Maize ears are harvested 8-14 days after pollination and surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560 L medium 4 days prior to bombardment in the dark. Medium 560 L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560 L with high sucrose concentration).

A plasmid vector comprising the ODP2 sequence operably linked to the selected promoter is constructed. This plasmid DNA plus plasmid DNA containing a PAT selectable marker is precipitated onto 1.1 μm (average diameter) tungsten pellets using a CaCl$_2$ precipitation procedure as follows: 100 μl prepared tungsten particles in water, 10 μl (1 μg) DNA in TrisEDTA buffer (1 μg total), 100 μl 2.5M CaCl$_2$, 10 μl 0.1M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 μl 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are positioned 2 levels below the stooping plate for bombardment in a DuPont Helium Particle Gun. All samples receive a single shot at 650 PSI, with a total often aliquots taken from each tube of prepared particles/DNA. As a control, embryos are bombarded with DNA containing the PAT selectable marker as described above without the gene of invention.

Following bombardment, the embryos are kept on 560Y medium, an N6 based medium, for 2 days, then transferred to 560R selection medium, an N6 based medium containing 3 mg/liter Bialaphos, and subcultured every 2 weeks. After approximately 10 weeks of selection, bialaphos-resistant callus clones are sampled for PCR and activity of the gene of interest. In treatments containing the ODP2 gene, it is expected that growth will be stimulated and transformation frequencies increased, relative to the control. Positive lines are transferred to 288J medium, an MS based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the gene of interest.

Example 9. Ectopic Expression of Maize ODP2 to Induce Embryogenesis

Using the genotype High type II as an example, immature embryos are isolated 15 days after pollination and cultured on 560P medium for 3-5 days. At this developmental stage the embryos are too large for callus initiation under standard culture conditions (see above). Twelve hours before bombardment these embryos are transferred to high osmotic 560Y medium. Expression cassettes containing the ODP2 cDNA are then co-introduced into the scutella of these embryos along with an expression cassette containing genes encoding a screenable markers, such as green fluorescent protein (GFP) or cyan fluorescent protein (CFP) using methods well described in the art for particle gun transformations. Twelve to 24 hours following bombardment, embryos are then transferred back to 560P culture medium and incubated in the dark at 26° C. Cultures are then transferred every two weeks until transformed colonies appear. It is expected that expression of ODP2 will stimulate adventive embryo formation. This will be apparent when the cultures are compared to controls (transformed without the ODP2 cDNA). Using either inducible expression cassettes, tissue specific promoters, or promoters of varying strengths it will be possible to control the levels of expression to maximize the formation of adventive embryos. Using either non-responsive genotypes or sub-optimal culture conditions with responsive genotypes, only the transformed cells expressing the ODP2 cDNA will form embryos and regenerate plants. In this manner, ODP2-induced embryo proliferation can be used as a positive selective marker (only the cells expressing the gene will form embryos) and transformants can be recovered without a negative selective agent (i.e. bialaphos, basta, kanamycin, etc.).

Example 10. Ectopic Expression of Maize ODP2 is Sufficient to Stimulate Organogenesis/Embryogenesis and Increases Transformation Frequencies in Recalicitrant Tissues There exists only a small developmental window in which maize embryos are amenable to tissue culture growth, a prerequisite for transformation. Normally this occurs between 9-12 days after pollination when the immature embryos are between 1.0-1.5 mm in length. Older, larger embryos fail to produce embryogenic callus and thus cannot be transformed. To demonstrate that ODP2 can be used to induce embryogenesis, embryos from the maize inbred PH581, ATCC deposit PTA-4432, were isolated 17 days after pollination and used for transformation experiments. Isolated embryos were cultured on 605J medium (a medium containing both full strength MS salts (macro and micronutient) and 0.6×N6 macronutrient salts plus additional B5 micronutrients, with a mixture of SH and Eriksson's vitamin, L-proline and casamino acids, silver nitrate, 0.3 mg/l 2.4-D and 1.2 mg/l Dicamba, 2% sucrose and 0.06% glucose, solidified with agar). The embryos were incubated in the dark at 28° C. overnight. Embryos were shot in a method similar to that in Example 8 substituting 0.6 μm gold particles for tungsten. DNA was delivered using co-transformation, as noted above. As a control, embryos were shot with a 1:1 mixture of plasmid DNA's containing a Ubiquitin driven yellow fluorescence protein (YFP) and a plasmid containing a Ubiquitin driven uidA gene (GUS). In the ODP2 treatment the embryos were bombarded with a 1:1 mixture of plasmid DNA's containing the Ubiquitin promoter driving expression of YFP (Ubi:YFP) and a plasmid containing ODP2 (SEQ ID NO: 3) driven by the maize Ubiquitin promoter (Ubi:ODP2). Each treatment contained 20 embryos. After one month of culture the embryos were observed under the dissecting microscope using epifluorescence.

As mentioned above, it is well known in the art that there is a narrow window in embryo ontogeny where embryos are culture/transformation responsive and this window occurs when embryos are in 1-2 mm in length which is typically 9-12 days after pollination. Since these embryos were taken at 17 days after pollination no multicellular colonies were expected in the control treatment. As expected, hundreds of cells transiently expressing the YFP protein were visible under a fluorescent microscope in the control treatment, and in this population of fluorescing cells, cell division was very rare. Cells transiently expressing YFP were also apparent in the ODP2 treatment. However, in the ODP2 treatment, cell division was apparent in all of the bombarded embryos with up to 50 multicellular colonies observed per embryo (data not shown). No events were observed in the control treatment while 100% of the ODP2 embryos were transformed with 5-50 events/embryo. Embryo morphology was clearly visible in many of these growing transgenic colonies.

As mentioned above ODP2 expression was sufficient to induce embryogenesis in larger and normally non-responsive embryos. In a similar manner, controlled ODP2 expression should allow transformation of other vegetative tissues such as leaves, stems, and even seed. ODP2 driven by the ubiquitin promoter was used to transform stem tissues. Transformed embryos were recovered from stem tissues (data not shown).

Example 11. Transient Expression of the ODP2 Gene Product to Induce Embryogenesis It may be desirable to "kick start" meristem formation by transiently expressing the ODP2 gene product. This can be done by delivering ODP2 5' capped polyadenylated RNA, expression cassettes containing ODP2 DNA, or ODP2 protein. All of these molecules can be delivered using a biolistics particle gun. For example, 5' capped polyadenylated ODP2 RNA can easily be made in vitro using Ambion's mMessage mMachine kit. Following a delivery procedure outlined above, RNA is co-delivered along with DNA containing an agronomically useful expression cassette. It is expected that cells receiving ODP2 will form embryos and a large portion of these will have integrated the agronomic gene. Plants regenerated from these embryos can then be screened for the presence of the agronomic gene.

Example 12. Modifying the Regenerative Capacity of a Plant

To demonstrate that ODP2 improves the regenerative capacity of maize tissues transformants were produced in the genotype High Type II with constructs containing the ODP2 gene driven by the maize Oleosin promoter. The Oleosin promoter is highly specific and is expressed only in scutella of developing embryos. Transformants were produced using both particle gun (as described in example 4 above) and *Agrobacterium* (U.S. Pat. No. 5,981,840). Putative transformants were grown in the greenhouse and were completely normal in phenotype. Ears were pollinated and segregating embryos were isolated from a particle gun event at 17 DAP (days after pollination) and from *Agrobacterium* derived events at 24 DAP. Embryos cultured at such late stages would be expected to germinate on regeneration medium. This was observed in the wild-type segregates but germination was delayed in the transformed embryos. In addition to delayed germination, somatic embryos proliferated from the scutella of the transformed embryos (data not shown) when cultured on regeneration medium. The maize Oleosin promoter is highly expressed at these late stages of development and this result demonstrates that the maize ODP2 gene is sufficient to induce embryogenesis in a normally non-responsive tissue.

Example 13. Transient Expression of ODP2 Enhances Transformation

Parameters of the transformation protocol can be modified to insure that the increased ODP2 activity is transient. One such method involves precipitating the ODP2-containing plasmid in a manner that precludes subsequent release of the DNA (thus, transcription from the particle-bound DNA can occur, but the frequency with which its released to become integrated into the genome is greatly reduced. Such a precipitation relies on the chemical PEI, and it could be used as discussed below.

The ODP2 plasmid is precipitated onto gold particles with PEI, while the transgenic expression cassette (UBI::moPAT~GFPm::pinII) to be integrated is precipitated onto gold particles using the standard $Ca^{++}$ method. Briefly, coating gold particles with PEI is done as follows. First, the gold particles are washed. Thirty-five mg of gold particles, for example 1.0 µM in average diameter (A.S.I. #162-0010), are weighed out in a microcentrifuge tube, and 1.2 ml absolute EtOH is added and vortexed for one minute. The tube is set aside for 15 minutes at room temperature and then centrifuged at high speed using a microfuge for 15 minutes at 4° C. The supernatant is discarded and a fresh 1.2 ml aliquot of EtOH is added, vortexed for one minute, centrifuged for one minute and the supernatant again discarded (this is repeated twice). A fresh 1.2 ml aliquot of EtOH is added, and this suspension (gold particles in EtOH) can be stored at −20° C. for weeks. To coat particles with polyethylimine (PEI; Sigma #P3143), start with 250 µl of washed gold particle/EtOH, centrifuge and discard EtOH. Wash once in 100 µl ddH2O to remove residual ethanol. Add 250 µl of 0.25 mM PEI, pulse-sonicate to suspend particles and then plunge tube into dry ice/EtOH bath to flash-freeze suspension into place. Lyophilize overnight. At this point, dry, coated particles can be stored at −80° C. for at least 3 weeks. Before use, rinse particles 3 times with 250 µl aliquots of 2.5 mM HEPES buffer, ph 7.1, with 1× pulse-sonication and then quick vortex before each centrifugation. Suspend in final volume of 250 µl HEPES buffer. Aliquot 25 µl to fresh tubes before attaching DNA. To attach uncoated DNA, pulse-sonicate the particles, then add DNA's and mix by pipetting up and down a few times with a Pipetteman™. Let sit for at least 2 minutes, spin briefly (i.e. 10 seconds), remove supernatant and add 60 µl EtOH. Spot onto macro-carriers and bombard following standard protocol. The $Ca^{++}$ precipitation and bombardment follows standard protocol for the PDS-1000.

The two particle preparations are mixed together; and the mixture is bombarded into scutellar cells on the surface of immature embryos (some cells receiving only an ODP2 particle, some cells receiving only a PAT~GFP particle and some cells receiving both). PEI-mediated precipitation results in a high frequency of transiently expressing cells on the surface of the immature embryo and extremely low frequencies of recovery of stable transformants (relative to the $Ca^{++}$ method). Thus, the PEI-precipitated ODP2 cassette expresses transiently and stimulates a burst of embryogenic growth on the bombarded surface of the tissue (i.e. the scutellar surface), but this plasmid does not integrate. The PAT~GFP plasmid released from the $Ca^{++}$/gold particles integrates and expresses the selectable marker at a frequency that result in substantially improved recovery of transgenic events.

As a control treatment, PEI-precipitated particles containing a UBI::GUS::pinII (instead of ODP2) are mixed with the PAT~GFP/$Ca^{++}$ particles. Immature embryos from both treatments are moved onto culture medium containing 3 mg/l bialaphos. After 6-8 weeks, GFP+, bialaphos-resistant calli are observed in the PEI/ODP2 treatment at a much higher frequency relative to the control treatment (PEI/GUS).

The ODP2 plasmid is precipitated onto gold particles with PEI, and then introduced into scutellar cells on the surface of immature embryos, and subsequent transient expression of the ODP2 gene elicits a rapid proliferation of embryogenic growth. During this period of induced growth, the explants are treated with Agrobacterium using standard methods for maize (Zhao et al., U.S. Pat. No. 5,981,840), with T-DNA delivery into the cell introducing a transgenic expression cassette such as UBI::moPAT~GFPm::pinII. After co-cultivation, explants are allowed to recover on normal culture medium, and then are moved onto culture medium containing 3 mg/l bialaphos. After 6-8 weeks, $GFP^+$, bialaphos-resistant calli are observed in the PEI/ODP2 treatment at a much higher frequency relative to the control treatment (PEI/GUS).

Example 14. Transient Expression of the ODP2 Polynucleotide Product to Induce Somatic Embryogenesis It may be desirable to "kick start" somatic embryogenesis by transiently expressing the ODP2 polynucleotide product. This can be done by delivering ODP2 5' capped polyadenylated RNA, expression cassettes containing ODP2 DNA, or ODP2 protein. All of these molecules can be delivered using a biolistics particle gun. For example 5' capped polyadenylated ODP2 RNA can easily be made in vitro using Ambion's mMessage mMachine kit. Following the procedure outline above RNA is co-delivered along with DNA containing an agronomically useful expression cassette, and a marker used for selection/screening such as Ubi::moPAT~GFPm::pinII. The cells receiving the RNA will immediately form somatic embryos and a large portion of these will have integrated the agronomic gene, and these can further be validated as being transgenic clonal colonies because they will also express the PAT~GFP fusion protein (and thus will display green fluorescence under appropriate illumination). Plants regenerated from these embryos can then be screened for the presence of the agronomic gene.

Example 15. Ectopic Expression of ODP2 in Early Zygotic Embryos Increases Seed Set During Abiotic Stress Episodes During periods of abiotic stress such as during a drought episode, embryo development often is halted resulting in aborted kernels on the ear. Preventing this kernel loss will increase or maintain yield. To increase seed set during periods of abiotic stress, the ODP2 gene is cloned into an expression cassette behind an early-embryo promoter such as LEC1, and this expression cassette is cloned along with a selectable/screenable marker into an *Agrobacterium* T-DNA region. For example, the following T-DNA is constructed: RB-LEC1::ODP2::pinII/Ubi::moPAT~GFPm::pinII-LB. This T-DNA is introduced into a maize inbred using standard *Agrobacterium* transformation methods. Transgenic plants are screened for single-copy integrations, and then planted in individual pots in the greenhouse. Transgenic plants are selfed and out-crossed to wild-type plants. Plants transgenic for the ODP2 expression cassette are easily tracked (using the cosegregating marker) through either BASTA resistance or green fluorescence conferred by the PAT~GFP fusion protein. Transgenic plants are planted in the field, and subjected to various degrees of drought stress during flowering and seed-set. Under identical stress regimes, the transgenic plants have much higher numbers of developed kernels relative to wild-type (non-transgenic) plants.

Example 16. Expression of ODP2 in Double-Haploid Production

There are two necessary steps in the production of double-haploid germplasm from maize inbreds. The first is induction of embryogenesis from a haploid cell, and the second is chromosome doubling to convert the haploid to a doubled-haploid.

The ODP2 gene can be used to generate haploid plants at high frequencies (i.e. improving the efficiency of step one of the process). Various strategies for accomplishing this are described below.

A. The following expression cassettes are placed in between a single set of T-DNA borders. T-DNA cassette #1 comprises RB-loxP/gal::FLP::pinII/PG47::C1-GAL-EcR::pinII/Ubi::PAT::pinII/Ubi:frt:YFP::pinII:frt:ODP2::pinII/LEC1::Cre::pinII/loxP-LB. To use this construct, it is first transformed into a maize genotype using *Agrobacterium* methods for 2-T-DNA transformation into immature embryos (Miller et al. (2002) *Transgene Research* 11:381-96).

In addition to the T-DNA diagramed above, this method also introduces T-DNA cassette #2 containing RB-Ole::WUS2::pinII/Ubi::CFP::pinII-LB, but which integrates at an unlinked location in the genome. T-DNA cassette #2 provides a means of recovering transformed events without chemical selection and then later segregating the T-DNA cassette #2 away from #1. Standard tissue culture and regeneration methods are used.

Transgenic plants are grown until the microspores in the developing tassel are at the uninucleate stage. At this point, the tassel is excised and pretreated by wrapping in moist paper towel and incubated for 14-17 days at 8-10° C. Following pre-treatment, tassels are surface sterilized by soaking for 10 minutes in sodium hypochlorite solution (i.e. 50% Chlorox), and then rinsed twice in sterile water. The anthers are then excised from the tassel and placed on solid anther culture medium using standard media formulations developed for maize anther culture (see Petolino and Genovesi (1994) in *The Maize Handbook*, (Walbot and Freeling, eds), pages 701-704). Once the anthers are on solid medium, the inducing agent methoxifenozide is pipetted directly onto the solid medium (for example, a 10 mM stock of methoxyfenozide is diluted to 10 uM by pipetting 30 ul of the stock onto the surface of 30 ml of solid medium and allowed to equilibrate before adding plant tissue). This will induce expression of FLP recombinase in the uninucleate microspores in the anther. FLP activity would excise the YFP gene, functionally linking the strong Ubiquitin promoter with the ODP2 gene. This burst of ODP2 expression will induce embryogenesis at high frequencies in the haploid uninucleate microspores. After the embryos begin developing, the embryogenic-specific promoter LEC1 will turn on Cre expression and this recombinase will excise the entire transgene cassette. Excision of the expression cassette and the concomitant loss of ODP2 expression will permit embryo maturation and subsequent plant regeneration to occur. During embryo development stimulated by the process described above, colchicine can be added (i.e. a 0.01 to 1.0% solution) to induce chromosome doubling. Doubled haploid plants are recovered that no longer contain T-DNA cassette #2 (because it was segregated away) and only contain the RB-loxP-LB sequence left behind after excision of almost all of cassette #1.

An alternative way to accomplish the above scenario would be to place the ODP2 gene behind a promoter that is active during microspore development. For example the maize promoters PG47, Zm-POL67 and Zm-POL95 are all promoters active during microspore development. In transgenic plants containing the PG47::ODP2 expression cassette, embryo formation is initiated in the microspores of the developing tassel. An embryo-specific promoter such as LEC1 or Glb1 is then used to drive expression of the Cre gene, which excises the loxP-flanked ODP2 and Cre expression cassettes. These embryos are then capable of maturing and germinating into haploid plants, or if exposed to a doubling agent such as colchicines, double-haploid plats are generated.

Example 17. ODP2 Expression for Positive Selection

It is expected that transformants can be recovered using ODP2 expression to provide a positive selection means under reduced auxin levels or in the absence of auxins in the medium, and in the absence of herbicide or antibiotic selection.

To determine if ODP2 can be used in a positive selection scheme, transformation experiments, using any standard method including particle gun or *Agrobacterium*, can be performed. Transformants are selected on medium with normal auxin levels, or on medium with reduced or no auxin, or visually (using GFP) on medium without bialaphos. Transformation frequencies are based on numbers of embryos with one or more multicellular GFP positive cell clusters. For example, one can test this concept using two treatment variables. The first is that immature embryos are bombarded with a control plasmid (UBI:PAT~GFP) or with UBI:PAT~GFP+In2:ODP2. The second variable is that the bombarded embryos are divided onto either normal bialaphos-containing selection medium (with normal auxin levels of 2 mg/L 2,4-D), or medium with no bialaphos and reduced 2,4-D levels (0.5 mg/L). It is expected from previous studies of positive selection that on bialaphos selection the ODP2 treatment will result in higher transformation frequency than the control. It is also anticipated that the low auxin medium (0.5 mg/L 2,4-D) will result in reduced growth rates. Consistent with this, it is expected that for the control plasmid treatment (UBI:PAT~GFP), recovery of GFP-expressing (fluorescent) colonies will be reduced relative to highly effective bialaphos selection treatment. In contrast, it is expected that ODP2 expression, through its stimulation of embryogenesis, may compensate for the low auxin environment, providing a growth advantage to the transgenic colonies, and maintaining the efficiency of transformant recovery at approximately the same range as the ODP2/bialaphos-selected treatment.

On medium completely devoid of auxin, it is expected that colonies will only be observed in the ODP2 treatment. In this experiment, immature embryos are transformed with either the control plasmid (UBI:PAT~GFP) or with UBI:PAT~GFP+In2:0DP2, and then plated either onto 3.0 mg/L bialaphos, 2.0 mg/L 2,4-D medium or onto no-bialaphos, no 2,4-D medium (in this latter treatment, wild-type maize callus will not exhibit embryonic growth). Again, it is expected that expression of the ODP2 polynucleotide will increase transformation significantly over the control plasmid value on normal auxin-containing, bialaphos selection medium. Also, it is expected that no transformants will be recovered with the control plasmid on medium devoid of exogenous auxin.

Even on auxin-containing medium, the ODP2 polynucleotide in combination with GFP+ expression can be used to recover transformants without chemical selection. For example, under these conditions it is expected that the recovery of transformants will be relatively efficient, but may require more diligence than the low- or no-auxin treatments above to separate the GFP-expressing colonies from the growing callus population.

Example 18. Soybean Embryo Transformation

Soybean embryos are bombarded with a plasmid containing the ODP2 sequence operably linked to a promoter. This could be a weak promoter such as nos, a tissue-specific promoter, such as globulin-1, an inducible promoter such as In2, or a strong promoter such as ubiquitin plus a plasmid containing the selectable marker gene PAT (Wohlleben et al. (1988) *Gene* 70:25-37) that confers resistance to the herbicide Bialaphos. Transformation is performed as follows.

To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the ODP2 operably linked to the promoter can be isolated as a restriction fragment. This fragment can then be inserted into a unique restriction site of the vector carrying the marker gene.

To 50 ul of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µ70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 19. Sunflower Meristem Tissue Transformation Prophetic Example

Sunflower meristem tissues are transformed with an expression cassette containing the ODP2 sequence operably linked to a promoter. This could be a weak promoter such as nos, a tissue-specific promoter, such as globulin-1, an inducible promoter such as In2, or a strong promoter such as ubiquitin plus a plasmid containing the selectable marker gene PAT (Wohlleben et al. (1988) *Gene* 70:25-37) that confers resistance to the herbicide Bialaphos. Transformation is performed as follows. See also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) Plant Cell Rep. 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) Physiol. Plant., 15: 473-497), Shepard's vitamin additions (Shepard (1980) in Emergent Techniques for the Genetic Improvement of Crops (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to Agrobacterium treatment (Bidney et al. (1992) Plant Mol. Biol. 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed Agrobacterium tumefaciens strain EHA105 is used in all transformation experiments. A binary plasmid vector comprising the expression cassette that contains the ODP2 gene operably linked to the promoter is introduced into Agrobacterium strain EHA105 via freeze-thawing as described by Holsters et al. (1978) Mol. Gen. Genet. 163: 181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final OD600 of 0.5 in an inoculation medium comprised of 12.5 mM MES pH 5.7, 1 gm/l $NH_4Cl$, and 0.3 gm/l $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for ODP2 activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by ODP2 activity analysis of leaf extracts while transgenic seeds harvested from NPTII-positive $T_0$ plants are identified by ODP2 activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into Agrobacterium tumefaciens strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for ODP2 activity using assays known in the art. After positive (i.e., for ODP2 expression) explants are identified, those shoots that fail to exhibit ODP2 activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for ODP2 expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING

```
<160> NUMBER OF SEQ ID NOS: 38

<210> SEQ ID NO 1
<211> LENGTH: 2260
<212> TYPE: DNA
<213> ORGANISM: Zea mays
<220> FEATURE:
<221> NAME/KEY: misc_feature
<222> LOCATION: (0)..(0)
<223> OTHER INFORMATION: Full length nucleotide sequence of Zm-ODP2,
      including the 5' untranslated region
<220> FEATURE:
<221> NAME/KEY: misc_feature
<222> LOCATION: (128)..(2260)
<223> OTHER INFORMATION: CDS

<400> SEQUENCE: 1
cttccctaac ctttgcactg tccaaaatgg cttcctgatc ccctcacttc ctcgaatcaa      60
tctaagaaga aactcaagcc gcaaccatta ggggcagatt aattgctgca ctttcagata     120
atcaaccatg gccactgtga caactggct cgctttctcc ctctccccgc aggagctgcc     180
gccctcccag acgacggact ccacactcat ctcggccgcc accgccgacc atgtctccgg     240
cgatgtctgc ttcaacatcc cccaagattg gagcatgagg ggatcagagc tttcggcgct     300
cgtcgcggag ccgaagctgg aggacttcct cggcggcatc tccttctccg agcagcatca     360
caaggccaac tgcaacatga tacccagcac tagcagcaca gtttgctacg cgagctcagg     420
tgctagcacc ggctaccatc accagctgta ccaccagccc accagctcag cgctccactt     480
cgcggactcc gtaatggtgg cctcctcggc cggtgtccac gacggcggtg ccatgctcag     540
cgcggccgcc gctaacggtg tcgctggcgc tgccagtgcc aacggcggcg gcatcgggct     600
gtccatgatt aagaactggc tgcggagcca accggcgccc atgcagccga gggtggcggc     660
ggctgagggc gcgcagggc tctctttgtc catgaacatg gcggggacga cccaaggcgc     720
tgctggcatg ccacttctcg ctggagagcg cgcacgggcg cccgagagtg tatcgacgtc     780
agcacagggt ggagccgtcg tcgtcacggc gccgaaggag gatagcggtg gcagcggtgt     840
tgccggcgct ctagtagccg tgagcacgga cacgggtggc agcggcggcg cgtcggctga     900
caacacggca aggaagacgg tggacacgtt cgggcagcgc acgtcgattt accgtggcgt     960
gacaaggcat agatggactg ggagatatga ggcacatctt tgggataaca gttgcagaag    1020
ggaagggcaa actcgtaagg gtcgtcaagt ctatttaggt ggctatgata aagaggagaa    1080
```

```
agctgctagg gcttatgatc ttgctgctct gaagtactgg ggtgccacaa caacaacaaa    1140
ttttccagtg agtaactacg aaaaggagct cgaggacatg aagcacatga caaggcagga    1200
gtttgtagcg tctctgagaa ggaagagcag tggtttctcc agaggtgcat ccatttacag    1260
gggagtgact aggcatcacc aacatggaag atggcaagca cggattggac gagttgcagg    1320
gaacaaggat ctttacttgg gcaccttcag cacccaggag gaggcagcgg aggcgtacga    1380
catcgcggcg atcaagttcc gcggcctcaa cgccgtcacc aacttcgaca tgagccgcta    1440
cgacgtgaag agcatcctgg acagcagcgc cctccccatc ggcagcgccg ccaagcgcct    1500
caaggaggcc gaggccgcag cgtccgcgca gcaccaccac gccggcgtgg tgagctacga    1560
cgtcggccgc atcgcctcgc agctcggcga cggcggagcc ctggcggcgg cgtacggcgc    1620
gcactaccac ggcgccgcct ggccgaccat cgcgttccag ccgggcgccg ccagcacagg    1680
cctgtaccac ccgtacgcgc agcagccaat gcgcggcggc gggtggtgca agcaggagca    1740
ggaccacgcg gtgatcgcgg ccgcgcacag cctgcaggac ctccaccacc tgaacctggg    1800
cgcggccggc gcgcacgact ttttctcggc agggcagcag gccgccgccg ctgcgatgca    1860
cggcctgggt agcatcgaca gtgcgtcgct cgagcacagc accggctcca actccgtcgt    1920
ctacaacggc ggggtcggcg acagcaacgg cgccagcgcc gtcggcggca gtggcggtgg    1980
ctacatgatg ccgatgagcg ctgccggagc aaccactaca tcggcaatgg tgagccacga    2040
gcaggtgcat gcacgggcct acgacgaagc caagcaggct gctcagatgg ggtacgagag    2100
ctacctggtg aacgcggaga caatggtgg cggaaggatg tctgcatggg ggactgtcgt    2160
gtctgcagcc gcggcggcag cagcaagcag caacgacaac atggccgccg acgtcggcca    2220
tggcggcgcg cagctcttca gtgtctggaa cgacacttaa                         2260
```

<210> SEQ ID NO 2
<211> LENGTH: 710
<212> TYPE: PRT
<213> ORGANISM: Zea mays

<400> SEQUENCE: 2

```
Met Ala Thr Val Asn Asn Trp Leu Ala Phe Ser Leu Ser Pro Gln Glu
 1               5                  10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Asn Gly
    130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
```

```
              165                 170                 175
Ala Ala Ala Glu Gly Ala Gln Gly Leu Ser Leu Ser Met Asn Met Ala
            180                 185                 190

Gly Thr Thr Gln Gly Ala Gly Met Pro Leu Leu Ala Gly Glu Arg
            195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Ser Gly Val Ala Gly
225                 230                 235                 240

Ala Leu Val Ala Val Ser Thr Asp Thr Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Gly Ala Leu Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
                565                 570                 575

Met His Gly Leu Gly Ser Ile Asp Ser Ala Ser Leu Glu His Ser Thr
            580                 585                 590
```

```
Gly Ser Asn Ser Val Val Tyr Asn Gly Gly Val Gly Asp Ser Asn Gly
        595                 600                 605

Ala Ser Ala Val Gly Gly Ser Gly Gly Gly Tyr Met Met Pro Met Ser
610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Arg Met Ser
            660                 665                 670

Ala Trp Gly Thr Val Val Ser Ala Ala Ala Ala Ala Ala Ser Ser
        675                 680                 685

Asn Asp Asn Met Ala Ala Asp Val Gly His Gly Gly Ala Gln Leu Phe
        690                 695                 700

Ser Val Trp Asn Asp Thr
705                 710

<210> SEQ ID NO 3
<211> LENGTH: 2133
<212> TYPE: DNA
<213> ORGANISM: Zea mays
<220> FEATURE:
<221> NAME/KEY: misc_feature
<222> LOCATION: (0)..(0)
<223> OTHER INFORMATION: Open reading frame of Zm-ODP2
<220> FEATURE:
<221> NAME/KEY: misc_feature
<222> LOCATION: (1)..(2133)
<223> OTHER INFORMATION: CDS

<400> SEQUENCE: 3
atggccactg tgaacaactg gctcgctttc tccctctccc cgcaggagct gccgccctcc      60
cagacgacgg actccacact catctcggcc gccaccgccg accatgtctc cggcgatgtc     120
tgcttcaaca tcccccaaga ttggagcatg aggggatcag agctttcggc gctcgtcgcg     180
gagccgaagc tggaggactt cctcggcggc atctccttct ccgagcagca tcacaaggcc     240
aactgcaaca tgatacccag cactagcagc acagtttgct acgcgagctc aggtgctagc     300
accggctacc atcaccagct gtaccaccag cccaccagct cagcgctcca cttcgcggac     360
tccgtaatgg tggcctcctc ggccggtgtc cacgacggcg tgccatgct cagcgcggcc     420 gccgctaacg tgtcgctgg cgctgccagt gccaacggcg cggcatcgg gctgtccatg     480 attaagaact ggctgcggag ccaaccggcg cccatgcagc cgagggtggc ggcggctgag     540
ggcgcgcagg ggctctcttt gtccatgaac atggcgggga cgacccaagg cgctgctggc     600
atgccacttc tcgctggaga gcgcacggg gcgcccgaga gtgtatcgac gtcagcacag     660
ggtggagccg tcgtcgtcac ggcgccgaag aggatagcg gtggcagcgg tgttgccggc     720
gctctagtag ccgtgagcac ggacacgggt ggcagcggcg cgcgtcggc tgacaacacg     780 gcaaggaaga cggtggacac gttcgggcag cgcacgtcga tttaccgtgg cgtgacaagg     840
catagatgga ctgggagata tgaggcacat ctttgggata cagttgcag aagggaaggg     900 caaactcgta agggtcgtca agtctatttta ggtggctatg ataaagagga gaaagctgct     960
agggcttatg atcttgctgc tctgaagtac tggggtgcca acaacaacaac aaattttcca    1020 gtgagtaact acgaaaagga gctcgaggac atgaagcaca tgacaaggca ggagtttgta    1080
gcgtctctga aaggaagag cagtggtttc tccagaggtg catccattta cagggggagtg    1140
```

```
actaggcatc accaacatgg aagatggcaa gcacggattg gacgagttgc agggaacaag    1200
gatctttact tgggcacctt cagcacccag gaggaggcag cggaggcgta cgacatcgcg    1260
gcgatcaagt tccgcggcct caacgccgtc accaacttcg acatgagccg ctacgacgtg    1320
aagagcatcc tggacagcag cgccctcccc atcggcagcg ccgccaagcg cctcaaggag    1380
gccgaggccg cagcgtccgc gcagcaccac cacgccggcg tggtgagcta cgacgtcggc    1440
cgcatcgcct cgcagctcgg cgacggcgga gccctggcgg cggcgtacgg cgcgcactac    1500
cacggcgccg cctggccgac catcgcgttc cagccgggcg ccgccagcac aggcctgtac    1560
cacccgtacg cgcagcagcc aatgcgcggc ggcgggtggt gcaagcagga gcaggaccac    1620
gcggtgatcg cggccgcgca cagcctgcag gacctccacc acctgaacct gggcgcggcc    1680
ggcgcgcacg acttttctc ggcagggcag caggccgccg ccgctgcgat gcacggcctg    1740
ggtagcatcg acagtgcgtc gctcgagcac agcaccggct ccaactccgt cgtctacaac    1800
ggcggggtcg cgacagcaa cggcgccagc ccgtcggcg cagtggcgg tggctacatg    1860 atgccgatga gcgctgccgg agcaaccact acatcggcaa tggtgagcca cgagcaggtg    1920
catgcacggg cctacgacga agccaagcag gctgctcaga tggggtacga gagctacctg    1980
gtgaacgcgg agaacaatgg tggcggaagg atgtctgcat gggggactgt cgtgtctgca    2040
gccgcggcgg cagcagcaag cagcaacgac aacatggccg ccgacgtcgg ccatggcggc    2100
gcgcagctct tcagtgtctg gaacgacact taa                                 2133
```

<210> SEQ ID NO 4
<211> LENGTH: 2392
<212> TYPE: DNA
<213> ORGANISM: Zea mays
<220> FEATURE:
<221> NAME/KEY: misc_feature
<222> LOCATION: (0)..(0)
<223> OTHER INFORMATION: ZM-ODP2 cDNA insert from EST clone
      cpflc.pk009.f4

<400> SEQUENCE: 4

```
cttccctaac ctttgcactg tccaaaatgg cttcctgatc ccctcacttc ctcgaatcaa      60
tctaagaaga aactcaagcc gcaaccatta ggggcagatt aattgctgca cttttcagata    120 atcaaccatg gccactgtga caactggct cgctttctcc ctctccccgc aggagctgcc     180
gccctcccag acgacggact ccacactcat ctcggccgcc accgccgacc atgtctccgg    240
cgatgtctgc ttcaacatcc cccaagattg gagcatgagg ggatcagagc tttcggcgct    300
cgtcgcggag ccgaagctgg aggacttcct cggcggcatc tccttctccg agcagcatca    360
caaggccaac tgcaacatga tacccagcac tagcagcaca gtttgctacg cgagctcagg    420
tgctagcacc ggctaccatc accagctgta ccaccagccc accagctcag cgctccactt    480
cgcggactcc gtaatggtgg cctcctcggc cggtgtccac gacggcggtg ccatgctcag    540
cgcggccgcc gctaacggtg tcgctggcgc tgccagtgcc aacggcggcg catcgggct    600 gtccatgatt aagaactggc tgcggagcca accggcgccc atgcagccga gggtggcggc    660
ggctgagggc gcgcagggc tctctttgtc catgaacatg gcggggacga cccaaggcgc    720
tgctggcatg ccacttctcg ctggagagcg cgcacgggcg cccgagagtg tatcgacgtc    780
agcacagggt ggagccgtcg tcgtcacggc gccgaaggag gatagcggtg gcagcggtgt    840
tgccggcgct ctagtagccg tgagcacgga cacgggtggc agcggcggcg cgtcggctga    900
caacacggca aggaagacgg tggacacgtt cgggcagcgc acgtcgattt accgtggcgt    960
```

```
gacaaggcat agatggactg ggagatatga ggcacatctt tgggataaca gttgcagaag    1020
ggaagggcaa actcgtaagg gtcgtcaagt ctatttaggt ggctatgata aagaggagaa    1080
agctgctagg gcttatgatc ttgctgctct gaagtactgg ggtgccacaa caacaacaaa    1140
ttttccagtg agtaactacg aaaaggagct cgaggacatg aagcacatga caaggcagga    1200
gtttgtagcg tctctgagaa ggaagagcag tggtttctcc agaggtgcat ccatttacag    1260
gggagtgact aggcatcacc aacatggaag atggcaagca cggattggac gagttgcagg    1320
gaacaaggat ctttacttgg gcaccttcag cacccaggag gaggcagcgg aggcgtacga    1380
catcgcggcg atcaagttcc gcggcctcaa cgccgtcacc aacttcgaca tgagccgcta    1440
cgacgtgaag agcatcctgg acagcagcgc cctccccatc ggcagcgccg ccaagcgcct    1500
caaggaggcc gaggccgcag cgtccgcgca gcaccaccac gccggcgtgg tgagctacga    1560
cgtcggccgc atcgcctcgc agctcggcga cggcggagcc ctggcggcgg cgtacggcgc    1620
gcactaccac ggcgccgcct ggccgaccat cgcgttccag ccgggcgccg ccagcacagg    1680
cctgtaccac ccgtacgcgc agcagccaat gcgcggcggc gggtggtgca agcaggagca    1740
ggaccacgcg gtgatcgcgg ccgcgcacag cctgcaggac ctccaccacc tgaacctggg    1800
cacggccggc gcgcacgact ttttctcggc ggtggctaca tgatgccgat gagcgctgcc    1860
ggagcgacca ctacatcggc aatggtgagc cacgagcaga tgcatgcacg ggcctacgac    1920
gaagccaagc aggctgctca gatggggtac gagagctacc tggtgaacgc ggagaacaat    1980
ggtggcggaa ggatgtctgc atgggggact gtcgtgtctg cagccgcggc ggcagcagca    2040
agcagcaacg acaacatggc cgccgacgtc ggccatggcg gcgcgcagct cttcagtgtc    2100
tggaacgaca cttaagctac gcgtacgtgc cggcctggct ctccgaattc gaaccgatcg    2160
atgcgtcgta aaaccgtaca ctgacataag taacaacact tagggttctt catggagagg    2220
tggccagtaa gttgttactt gtcatatgtt ttaagttctc aatttgtagc tggaaggaaa    2280
gctagggttt cttctgaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aa           2392

<210> SEQ ID NO 5
<211> LENGTH: 224
<212> TYPE: DNA
<213> ORGANISM: Zea mays
<220> FEATURE:
<221> NAME/KEY: misc_feature
<222> LOCATION: (0)..(0)
<223> OTHER INFORMATION: EST clone cpclc.pk005.c19

<400> SEQUENCE: 5
ccgccagcac aggcctgtac caccgtacg cgcagcagcc aatgcgcggc ggcgggtggt       60
gcaagcagga gcaggaccac gcggtgatcg cggccgcgca cagcctgcag gacctccacc     120
acctgaacct gggcacggcc ggcgcgcacg acttttctc ggcagggcag caggccgccg      180
ccgccgccgc gatgcacggc ctgggtagca ttgacagtgc gtcg                      224

<210> SEQ ID NO 6
<211> LENGTH: 2133
<212> TYPE: DNA
<213> ORGANISM: Artificial sequence
<220> FEATURE:
<223> OTHER INFORMATION: Variant of Zm-ODP2 having 97.1% seq id to SEQ
      ID NO:1 (Zm-ODP2). The ORF encodes the aa seq set forth in SEQ ID
      NO:2.
<220> FEATURE:
<221> NAME/KEY: misc_feature
```

<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 6

| | | | | | |
|---|---|---|---|---|---|
| atggccactg | tgaacaactg | gctcgctttc | tccctctccc | cgcaggagct | gccgccctcc | 60 |
| cagacgacgg | actccacact | catctcggcc | gcgacggccg | accatgtcag | cggcgatgtc | 120 |
| tgcttcaaca | tcccccaaga | ttggagcatg | aggggatcag | agctttcggc | gctggtcgcg | 180 |
| gagccgaagc | tggaggactt | cctcggcggc | atcagctttt | ccgagcagca | tcataaggcc | 240 |
| aactgcaaca | tgatacccag | cactagcagc | acagtttgct | acgcgagctc | aggtgctagc | 300 |
| accggctacc | atcaccagct | gtaccatcag | cccaccagct | cagcgctcca | cttcgcggac | 360 |
| tccgttatgg | tggcgtcctc | ggccggtgtc | cacgacggcg | gtgccatgct | cagcgcggcc | 420 |
| gccgctaacg | gtgtcgctgg | cgcagcgagt | gccaacggcg | gcggcatcgg | gctctccatg | 480 |
| attaagaact | ggctgcggag | ccaaccggcg | cccatgcagc | cgagggtggc | ggcggctgag | 540 |
| ggcgcgcagg | ggctctctct | ctccatgaac | atggcgggga | cgacccaagg | cgctgctggc | 600 |
| atgccacttc | tcgctggaga | gcgcgcacgg | gcgcccgaga | gtgtatcgac | gtcagcacag | 660 |
| ggtggagccg | tcgtcgtcac | ggccccgaag | gaggatagcg | gtggcagcgg | tgttgccggc | 720 |
| gctctagtag | ccgtgagcac | ggacacgggt | ggcagcggcg | gcgcgtcggc | tgacaacacg | 780 |
| gcaaggaaga | cggtggacac | gttcgggcag | cgcacgtcga | tttaccgtgg | ggtcacaagg | 840 |
| catagatgga | cagggagata | cgaggcacat | ctttgggata | cagttgcag | aagggaaggg | 900 |
| caaactcgta | agggtcgtca | agtctattta | ggtggctatg | ataaagagga | gaaagctgct | 960 |
| agggcttatg | atcttgctgc | tctgaagtac | tggggagcca | caacaacaac | aaattttcca | 1020 |
| gtgtccaact | acgaaaagga | gctcgaggac | atgaagcata | tgacaaggca | ggagtttgta | 1080 |
| gcgtctctga | aaggaaaag | cagtggattc | tccaggggtg | caagcattta | caggggagtg | 1140 |
| actaggcatc | accagcatgg | aagatggcaa | gcacggattg | gacgagttgc | agggaacaag | 1200 |
| gatctttatt | tgggcacctt | tagcacccag | gaagaggcag | cggaggcgta | cgacatcgcg | 1260 |
| gcgatcaagt | ccgcggcct | caacgccgtc | accaacttcg | acatgagccg | ctacgacgtg | 1320 |
| aagagcattc | tggacagcag | cgccctcccc | attggcagcg | cggccaaacg | cctcaaggag | 1380 |
| gccgaggccg | cagcgtccgc | gcagcaccac | cacgccggcg | tggtgagcta | cgacgtcggc | 1440 |
| cgcatcgcct | cgcagctcgg | cgacggggga | gccctggcgg | cggcgtacgg | cgcgcactac | 1500 |
| cacggcgccg | cctggccgac | catcgccttc | agcccggcg | ccgccagcac | aggcctgtac | 1560 |
| cacccgtatg | cgcagcagcc | aatgcgcggc | ggcgggtggt | gcaagcagga | gcaggaccac | 1620 |
| gcggtcatcg | cggccgcgca | cagcctgcag | gacctccacc | atctgaacct | gggcgcggcc | 1680 |
| ggcgcgcacg | acttttttcag | cgcagggcag | caggccgccg | ccgctgcgat | gcacggcctg | 1740 |
| ggaagcatcg | acagtgcgtc | gctcgagcac | agcaccggct | ccaacagcgt | cgtctacaac | 1800 |
| ggcggggtcg | cgacagcaa | cggcgccagc | gccgtcggcg | gcagtggcgg | tggctacatg | 1860 |
| atgccgatga | gcgctgccgg | agcaaccact | acttcggcaa | tggtgagcca | cgagcaggtg | 1920 |
| catgcacggg | cctacgatga | agccaagcag | gctgctcaga | tgggctacga | gagctacctc | 1980 |
| gtgaacgcgg | agaacaatgg | tgggggtagg | atgtctgcat | ggggggacagt | cgtgtctgca | 2040 |
| gccgcggcgg | cagcagcaag | cagcaacgac | aacatggcgg | ccgatgtcgg | ccatggcggc | 2100 |

```
gcgcagctct tcagtgtctg aacgacact taa                              2133
```

<210> SEQ ID NO 7
<211> LENGTH: 2133
<212> TYPE: DNA
<213> ORGANISM: Artificial sequence
<220> FEATURE:
<223> OTHER INFORMATION: Variant of Zm-ODP2 having 92% seq id to SEQ ID
      NO:1.  The ORF encodes the aa seq set forth in SEQ ID NO:2.
<220> FEATURE:
<221> NAME/KEY: misc_feature
<222> LOCATION: (0)..(0)
<223> OTHER INFORMATION: synthesized
<220> FEATURE:
<221> NAME/KEY: misc_feature
<222> LOCATION: (1)..(2133)
<223> OTHER INFORMATION: CDS

<400> SEQUENCE: 7

```
atggccactg tcaacaattg gctggctttt agcctctccc cgcaggagct gccccctcc    60 cagaccacgg actccacact catctcggcg gccaccgccg accacgtgtc cggcgacgtg   120
tgctttaata ttccccagga ttggagcatg aggggatcag agctttcggc gctcgtcgcg   180
gagccgaagc tggaggactt cctcggcggg atctccttct ccgaacaaca tcacaaggcc   240
aactgtaaca tgatacccctc cactagcagc acagtttgct acgcgagctc aggtgcaagc   300
accgggtatc atcaccagct gtaccaccag cccaccagct cagcgctcca cttcgcggac   360
tccgttatgg tggcctcctc ggccggagtc cacgacggcg gtgccatgct gtccgccgcc   420
gccgctaacg gagtggctgg cgctgcctcc gccaacggcg gcgggatcgg gctgagcatg   480
atcaagaact ggctccggag ccaaccggcg cccatgcagc cgagggtggc ggcggctgag   540 gggcccagg gcctctcttt gtccatgaac atggcgggga cgacccaagg cgcagctggc   600
atgcctcttc tggctggaga gcgcgcacgc gcgcccgaga gtgtatcgac gtcagctcaa   660
ggtggagcgg tcgtcgtcac cgcgccgaag aagattccg gtggcagcgg tgttgccggc   720
gctctcgtag cggtcagcac ggacaccggt ggcagcgggg gcgcgtcggc agacaatacg   780
gctaggaaga cggtggacac gttcgggcag cggacgtcga tctaccgtgg ggtgacaagg   840
cacagatgga cagggagata tgaggcacac cttggggata acgttgcag gagggaaggg   900 caaactcgta aaggtagaca agtctatttata ggtggctatg acaaagagga gaaggctgct   960
agggcttacg atcttgcagc tctgaagtac tggggtgcca ctactactac aaatttccca   1020
gtgagtaact acgaaaagga gctggaggac atgaagcaca tgactaggca agagttcgtt   1080
gcgtccctga aagaaaagag cagtggtttc tccagaggtg catccatta caggggagtg   1140 actaggcatc accaacatgg aagatggcag gctcggattg gacgcgtggc aggcaacaaa   1200
gatctgtact tgggcaccctt tagcacccag gaggaagcag cggaggcgta cgacatcgcg   1260
gccatcaaat tccgcggggct caacgcggtg acgaattttg acatgagccg ctacgacgtc   1320
aagagcattc tggatagcag cgccctcccc atcgggagcg ccgccaagcg cctgaaggag   1380
gccgaagccg ctgcgtccgc gcagcatcac cacgccggcg tggtgagcta cgacgtgggc   1440
cgcatcgcct cgcaactcgg cgacggcgga gccctggcgg cggcgtacgg ggcgcactac   1500
cacggcgcgg cctggcccac gatcgcgttc agccgggcg ccgccagcac aggcctctac   1560
cacccgtacg cccagcaacc aatgcgcggg ggcgggtggt gcaagcagga gcaagaccac   1620
gccgtgatcg cggccgcgca cagcctgcag gacctgcatc acctgaacct cggggcggcc   1680
ggcgcccacg acttttttctc ggcagggcaa caggccgcgg ccgctgccat gcacggcctg   1740
```

```
ggtagcatcg atagtgcgtc gctcgaacac agcaccggca gcaactccgt cgtctataac    1800
ggcggcgtcg gcgacagcaa tggggccagc gcggtcggcg gctccggggg tggctatatg    1860
atgcccatga gcgctgccgg tgcaacgaca acaagcgcaa tggtgagcca cgagcaagtc    1920
catgcacggg cctacgacga agccaagcag gctgctcaga tggggtacga gagctacctg    1980
gtcaacgcgg agaacaatgg tggcggaaga atgtctgcat gggggactgt cgtgtctgca    2040
gccgcggcgg cagctgcttc cagcaacgac aacatggccg ccgacgtggg ccatgggggg    2100
gcgcagctct ttagtgtctg gaacgatact taa                                 2133
```

<210> SEQ ID NO 8
<211> LENGTH: 2133
<212> TYPE: DNA
<213> ORGANISM: Artificial sequence
<220> FEATURE:
<223> OTHER INFORMATION: Variant of Zm-ODP2 having 86.3% seq id to SEQ
      ID NO:1. The ORF encodes the  aa seq set forth in SEQ ID NO:2.
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 8

```
atggccacag tgaacaattg gctggctttt agcctctccc cccaagagct gccccgtcc      60 cagacgacgg atagcacact gattagcgcg gccaccgccg accatgtctc cggggacgtc    120
tgcttcaaca tcccccagga ttggagcatg agaggaagcg agctttcggc cctggtcgcg    180
gagcccaagc tggaagattt tctgggcggc attagcttct ccgagcagca tcataaggcg    240
aattgcaaca tgataccgag cacttcctcc actgtttgtt acgcgagcag cggtgctagc    300
acgggctatc accatcaact gtaccaccag ccgaccagct cagcgctcca cttcgcggat    360
agcgtaatgg tggcctcctc ggccggtgtc cacgatgggg gtgccatgct ctccgcggcc    420
gccgctaatg tgtcgctgg cgctgccagt gcgaacggcg gggggatcgg gctctccatg     480
attaagaact ggctgcggag ccagccggcc cccatgcaac cgagggtggc ggccgcagaa    540
ggcgcgcagg ggctctcctt gtccatgaac atggccggca ccacgcaagg cgctgcaggg    600
atgcctcttc tcgctggtga gcgggcacgg gccccggagt ccgtatcgac cagcgcacag    660
ggaggagcgg tcgtggtgac cgcgccgaaa gaggactccg gtggcagcgg tgtggcgggc    720
gctctagttg ccgtgtccac ggacaccgga gggtccggcg gcgcgtcggc tgacaacacc    780
gcaaggaaga ccgtggacac gttcgggcag cgcacgagca tctatcgtgg cgtcacaaga    840
catagatgga ctggcaggta tgaagcacac ctttgggata acagttgcag agagaagggg    900
cagactagaa agggacgtca agtctacctg ggtgggtacg ataagagga aaaagctgct     960 agagcttacg accttgctgc tctcaaatac tgggagcca caacaacaac taatttttcct   1020 gtgagtaatt acgagaaaga gctcgaagat atgaagcaca tgactaggca ggagttcgtt   1080
gcgtccctga aaggaaaag ctccggtttc tccagaggtg cttccatcta tagaggagtc    1140
acaaggcatc atcaacatgg aagatggcag gctcggatcg gacgcgtggc agggaacaag   1200
gatctttatc tcggcacgtt cagcacgcaa gaagaagcag ccgaagcgta cgacatcgcc   1260
gccatcaaat tccgcggcct gaacgccgtc accaatttcg atatgagccg gtacgacgtc   1320
aaaagcattc tggacagcag cgccctcccc atcgggagcg ccgccaagcg gctgaaagag   1380
```

```
gccgaggccg ctgcgagcgc gcagcaccat catgcgggcg tcgtcagcta tgacgtgggg    1440
cggattgcga gccaactggg ggacggcggt gccctggcgg cggcctacgg cgcgcactac    1500
catggcgccg cgtggcccac catcgcgttc aaccgggcg ccgccagcac aggcctctat     1560 caccccctacg cgcaacaacc aatgcgcggg ggcgggtggt gtaagcagga gcaagatcat   1620
gcggtcatcg cggccgccca cagcctccag gatctgcacc acctcaacct gggcgccgcc   1680
ggcgcgcacg acttttcag cgcaggccag caagcggccg ccgcagcgat gcacgggctc     1740
ggaagcatcg atagtgcgtc gctcgagcac agcacgggct ccaattccgt ggtctacaac    1800
ggcggcgtgg gggatagcaa cggcgcctcc gccgtcggcg ggtccggcgg tggctacatg    1860
atgccgatga gcgctgccgg agcaaccact acatcggcaa tggtcagcca tgaacaagtg    1920
catgcacggg cctatgacga agcgaagcaa gctgctcaaa tggggtacga atcctacctg    1980
gtgaacgcgg agaataatgg aggcggaaga atgtctgctt gggggacagt cgtgtccgct    2040
gccgcggcgg ctgcagctag cagcaatgac aatatggcgg cggacgtcgg ccacggcggc    2100
gcgcagctgt tctccgtgtg gaatgacact taa                                 2133
```

<210> SEQ ID NO 9
<211> LENGTH: 2133
<212> TYPE: DNA
<213> ORGANISM: Artificial sequence
<220> FEATURE:
<223> OTHER INFORMATION: Variant of Zm-ODP2 having 81.2% seq id to SEQ
    ID NO:1. The ORF encodes the aa seq set forth in SEQ ID NO:2.
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 9

```
atggcgactg tcaataattg gctggcattt agcctcagcc cccaggagct gccgccgtcc      60
caaacgaccg acagcacact gattagcgcg gcgacggcgg atcacgtgag cggcgatgtg    120
tgtttcaaca ttccccagga ctggtccatg agggggtagcg aacttagcgc gctcgtggcg   180
gaaccgaaac tggaggactt cctgggggc atctcctttt ccgagcagca tcacaaagcg    240
aactgtaaca tgatccccag cactagcagc acagtttgtt atgcctcctc aggtgcttcc    300
acgggctacc accatcagct gtatcaccaa ccgaccagct cagcgctcca ctttgcggat    360
tccgtaatgg tggcctccag cgccggagtc cacgacgggg gtgcgatgct cagcgcggcc    420
gccgctaatg gagtggcagg ggctgcgagt gcgaacggcg gcggcattgg gctctccatg    480
atcaaaaatt ggctgcggtc ccagccgcg ccgatgcagc ccagagtggc cgccgctgaa     540
ggcgcccaag gcctgtccct cagcatgaac atggcgggga cgacccaggg cgcagcaggg    600
atgccacttc tcgcaggtga acgcgctcgc gcgcccgagt ccgtaagcac cagcgcacag    660
ggaggtgcgg tggtggtcac ggccccgaag gaagattccg gagggagcgg agtggccggg    720
gcactcgtag ccgtgagcac ggacaccgga gggtccgggg gggcctcggc agataatacc    780
gctagaaaaa cggtcgacac gtttggccag cgcacgtcga tctatagagg cgtgacaagg    840
cacagatgga caggcagata cgaagctcac ctttgggata acagttgcag aagggaaggg    900
caaactagaa agggacgtca ggtctatctg ggaggctacg acaaagagga gaaggcagca    960
agagcatacg atctggctgc actgaaatac tggggagcca caactactac taattttca   1020
```

```
gtgagtaact acgagaaaga actggaggac atgaagcaca tgactagaca agaattcgta    1080
gcgtctctga ggagaaagag ctccggattc agcaggggtg catccatcta tagggggtgtc   1140 acaaggcacc accagcacgg aagatggcag gctcgcatcg gacgagttgc agggaacaaa    1200
gatctgtatc tcggcacgtt ttccacccag gaagaagcag ccgaggcgta cgacatcgcg    1260
gccatcaaat ttcgcggcct caatgccgtc acgaatttcg atatgagccg ctatgacgtg    1320
aagtccattc tcgatagctc cgcgctcccc atcgggtccg cggcgaagcg cctgaaggag    1380
gccgaggcgg ctgcctccgc ccaacatcat catgccggcg tcgtgtccta cgatgtcggg    1440
cggatcgcga gccagctggg cgatggggga gcgctggccg cggcgtatgg ggcccactac    1500
cacggcgcgg cgtggccgac gatcgcgttt cagcccggcg cggccagcac tggcctgtac    1560 caccccctatg cccaacaacc tatgcggggg ggggctggt gcaaacaaga gcaagaccat    1620
```

(Note: line at 1620 contains "ccccctatg cccaacaacc tatgcggggg ggggctggt gcaaacaaga gcaagaccat")

```
gccgtgattg ccgcggccca ctccctccag gacctgcatc acctcaatct gggggccgcg    1680
ggggcccatg attttttttc ggctggccaa caagcggcgg cggctgcgat gcatgggctg    1740
ggaagcatcg attccgcgag cctcgagcat tccacgggct ccaatagcgt cgtgtataat    1800
gggggcgtgg cgacagcaa tggcgcgagc gcggtcgggg ggagtggcgg agggtacatg    1860
atgccgatga gcgctgcggg tgctaccaca acttcggcaa tggtgagcca cgagcaggtg    1920
catgcacgcg cctatgacga agcgaaacaa gcagcacaaa tgggctacga gagctacctc    1980
gtgaacgccg aaaataacgg tggggtagg atgtctgctt ggggggacagt ggtctccgca    2040 gcggcggccg ctgcagcaag cagcaacgac aacatggcgg cggacgtcgg ccacgggggg    2100
gcccagctgt tctccgtctg gaacgataca taa                                 2133

<210> SEQ ID NO 10
<211> LENGTH: 2133
<212> TYPE: DNA
<213> ORGANISM: Artificial sequence
<220> FEATURE:
<223> OTHER INFORMATION: Variant of Zm-ODP2 having 76.1% seq id to SEQ
      ID NO:1.  The ORF encodes the  aa seq set forth in SEQ ID NO:2.
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 10
atggcgactg tgaataattg gctggctttt agcctgagcc cccaggaact gccccgtcc      60 caaaccaccg attccactct gattagcgcg gccacggccg atcatgtgtc cggcgatgtc    120
tgctttaata ttccgcagga ctggagcatg agaggatcag aactgagcgc cctcgtggcg    180
gaacccaaac tcgaagattt cctggggggg attagcttca gcgaacagca ccacaaagcg    240
aattgtaata tgataccgtc cactagctcc acagtttgtt atgccagcag cggagcaagc    300
acggggtacc accatcagct ctatcatcaa cccacgtcca gcgccctgca ctttgccgat    360
agcgttatgg tggcgtccag cgcgggtgtc catgacggcg gtgcgatgct gagcgcggcc    420
gccgctaacg gagtggcagg ggctgcctcc gcgaatggcg ggggatcgg gctcagcatg    480 attaaaaaact ggctccgctc ccaacccgcc ccgatgcaac ccagagtcgc cgcggctgaa    540
ggggcgcaag gcctgtccct ctccatgaac atggccggga ccacgcaagg ggcagcaggg    600
atgcctctgc tggctggaga acgggctcgc gcgcccgaat ccgtatcgac cagcgctcaa    660
```

```
ggaggtgcgg tggtggtgac ggcgccgaag aagacagcg gtgggagcgg tgtggcgggg    720
gctctagtag cggtctccac cgacaccgga ggcagcggcg gcgcgtcggc tgataatacc    780
gctagaaaga cggtggatac cttcggccag cggaccagca tctatcgtgg ggtcactaga    840
cacaggtgga caggcaggta cgaagctcat ctttgggata attcctgtag aagggagggc    900
cagactagaa agggtagaca ggtgtactta ggtggctacg acaaggaaga aaaggcagca    960
agggcatacg acctggcagc tctcaagtat tggggagcga ctactacaac aaatttccca   1020
gtcagtaact atgagaaaga actggaggat atgaaacata tgacaagaca agaattcgtt   1080
gcctccctca ggagaaaaag cagtggattc tccaggggtg cttccatcta cagggggtgtc   1140 acaaggcacc atcagcatgg aaggtggcag gcacgcatcg gacgcgttgc aggcaataaa   1200
gatctgtacc tcgggacgtt ctccacgcag aagaagcag cggaggcgta tgacattgcg   1260
gccattaagt ttcgggcct caatgcggtc acgaattttg acatgtcccg ctatgatgtc   1320
aaatccattc tcgatagctc cgcgctcccc attggctccg cggcgaagcg cctcaaagaa   1380
gccgaagcgg ctgccagcgc gcaacaccat catgccgggg tggtctccta tgacgtcggg   1440
cggattgcct cgcagctggg ggatgggggt gccctggccg ccgcgtatgg ggcccattac   1500 catggcgcg cctggccgac gatcgccttt cagcccgggg cggcgagcac tgggctgtac   1560
catccctacg cgcaacaacc tatgcgcggg ggggctggt gtaaacaaga acaggaccat   1620
gccgtcattg ccgcggccca ctccctccag gacctgcatc acctgaatct cggggcggcg   1680
ggggcccatg atttcttctc ggctggccaa caggcggcgg cggcagccat gcatgggctg   1740
ggatccattg actccgcctc gctggagcat tccacgggca gcaactccgt cgtgtacaat   1800
ggcggcgtgg gggattccaa tggggcctcc gcggtggggg ggtccggcgg agggtatatg   1860
atgcccatga gcgcagcggg tgcaaccaca acttcggcta tggtctccca tgaacaagtg   1920
cacgctcggg cgtatgatga ggcgaaacaa gcagcacaaa tggggtatga gtcctatctg   1980
gtgaatgccg aaaataacgg aggggggtaga atgtccgctt gggggacagt ggtctccgca   2040
gcggcggcgg ctgctgcaag ctccaacgat aatatggccg cggatgtggg gcacggggg    2100 gcccaactgt tcagtgtgtg gaatgacaca taa                                2133
```

<210> SEQ ID NO 11
<211> LENGTH: 2133
<212> TYPE: DNA
<213> ORGANISM: Artificial sequence
<220> FEATURE:
<223> OTHER INFORMATION: Variant of Zm-ODP2 having 70.6% seq id to SEQ
      ID NO:1. The ORF encodes the aa seq set forth in SEQ ID NO:2.
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 11

```
atggcgacag tcaacaattg gctggcattt agcctgagcc cccaagaact ccccccctcc     60
caaacgaccg atagcactct gattagcgcg gccacggccc atcacgtgag cggggacgtg    120
tgttttaata ttccgcagga ctggagcatg agaggatcag aactttcggc cctggtggcc    180
gagcccaaac tcgaagactt tctggggggg attagcttta gcgaacaaca ccacaaagcc    240
aattgtaaca tgatcccgtc cactagctcc acagtgtgct atgcctccag cggagcttcc    300
```

| | |
|---|---|
| acggggtacc accatcaact ctatcatcaa ccgacgagca gcgccctgca ttttgccgat | 360 |
| agcgttatgg tcgccagcag cgcgggagtg catgatgggg gagcgatgct gtccgccgcg | 420 |
| gcggcaaatg gagtggcagg cgcagcctcc gcgaatgggg gggggattgg cctcagcatg | 480 |
| atcaaaaatt ggctccgctc ccagcccgcc ccgatgcaac ccagagtcgc cgccgcagag | 540 |
| ggggcccaag ggctgtctct cagcatgaat atggcgggca ccacgcaggg ggcagcaggg | 600 |
| atgcctctgc tcgcaggtga acgggcacgc gccccggaaa gtgttagcac ctcagctcaa | 660 |
| ggaggtgccg tggtggtgac cgcgcccaaa gaagactccg gagggtccgg agtggccggg | 720 |
| gctctcgttg ccgtgtccac cgataccggt gggtccgggg gcgccagcgc agataatacc | 780 |
| gctagaaaaa cggtcgatac ctttggccaa cggacgtcga tctatagagg ggtcactagg | 840 |
| cacaggtgga caggcaggta cgaggcacac ctgtgggaca atagttgtag agagaaggc | 900 |
| cagacaagaa aaggacgtca ggtctatctg ggagggtacg acaaggaaga aaaggcagca | 960 |
| agagcatatg acctggcagc tctgaaatat tggggtgcga ctactactac taatttccct | 1020 |
| gtctccaatt atgagaaaga actggaagac atgaaacata tgactagaca agaatttgtt | 1080 |
| gcctccctca ggagaaaaatc ctccggattt agcaggggtg ctagcatcta tagaggtgtc | 1140 |
| acaaggcacc atcaacacgg aagatggcag gctcgcatcg gtcgcgtggc tggcaataaa | 1200 |
| gacctgtatc tcgggacgtt ttccacgcaa gaagaggcag ccgaagccta tgacattgcc | 1260 |
| gcgattaagt ttcgggggct gaatgcggtg accaattttg atatgagccg gtatgacgtc | 1320 |
| aaaagcatcc tcgattcctc cgcgctgccc attgggtccg cggcgaaacg gctgaaagaa | 1380 |
| gcggaagcgg ctgcctccgc ccaacatcat catgcggggg tcgtcagcta tgatgtgggg | 1440 |
| cggattgcga gccaactggg ggatgggggt gccctcgccg ccgcctatgg ggcccattat | 1500 |
| cacggggcgg cgtggcccac gattgccttt caaccgggcg cggcgtccac tgggctctat | 1560 |
| catccctatg cccaacaacc tatgcggggg ggcggctggt gcaagcagga acaagatcat | 1620 |
| gcggtcattg ccgccgccca ttccctgcaa gatctgcatc atctcaatct gggcgcggcg | 1680 |
| ggggcccatg acttcttctc ggctggccaa caagcggcgg cggcagccat gcacgggctc | 1740 |
| ggatccatcg actccgccag cctcgagcat tccaccggga gcaatagcgt ggtgtataat | 1800 |
| gggggcgtgg gcgattccaa tggggcgtcc gcggtcgggg ggagtggggg agggtatatg | 1860 |
| atgcccatgt ccgcagcggg tgctacgaca acttcggcaa tggtgtccca tgaacaagtc | 1920 |
| cacgctcggg cgtatgatga ggcgaaacaa gcagcacaaa tgggctatga aagctatctc | 1980 |
| gtcaacgccg aaaacaacgg aggggggtaga atgtccgctt ggggcactgt cgtctccgct | 2040 |
| gcggccgccg ctgctgcatc cagcaatgat aacatggcgc cggatgtggg gcacgggggg | 2100 |
| gcccaactct tttccgtgtg gaatgacaca taa | 2133 |

<210> SEQ ID NO 12
<211> LENGTH: 2133
<212> TYPE: DNA
<213> ORGANISM: Artificial sequence
<220> FEATURE:
<223> OTHER INFORMATION: Variant of Zm-ODP2 having the ser37 altered
      from tcc to the thr of acc. The ORF encodes the aa seq set forth
      in SEQ ID NO: 19.
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 12

```
atggccactg tgaacaactg gctcgctttc tccctctccc cgcaggagct gccgccctcc    60
cagacgacgg actccacact catctcggcc gccaccgccg accatgtcac cggcgatgtc   120
tgcttcaaca tcccccaaga ttggagcatg aggggatcag agctttcggc gctcgtcgcg   180
gagccgaagc tggaggactt cctcggcggc atctccttct ccgagcagca tcacaaggcc   240
aactgcaaca tgatacccag cactagcagc acagtttgct acgcgagctc aggtgctagc   300
accggctacc atcaccagct gtaccaccag cccaccagct cagcgctcca cttcgcggac   360
tccgtaatgg tggcctcctc ggccggtgtc cacgacggcg gtgccatgct cagcgcggcc   420
gccgctaacg tgtcgctgg cgctgccagt gccaacggcg gcggcatcgg gctgtccatg   480
attaagaact ggctgcggag ccaaccggcg cccatgcagc cgagggtggc ggcggctgag   540
ggcgcgcagg ggctctcttt gtccatgaac atggcgggga cgacccaagg cgctgctggc   600
atgccacttc tcgctggaga gcgcgcacgg gcgcccgaga gtgtatcgac gtcagcacag   660
ggtggagccg tcgtcgtcac ggcgccgaag gaggatagcg gtggcagcgg tgttgccggc   720
gctctagtag ccgtgagcac ggacacgggt ggcagcggcg gcgcgtcggc tgacaacacg   780
gcaaggaaga cggtggacac gttcgggcag cgcacgtcga tttaccgtgg cgtgacaagg   840
catagatgga ctgggagata tgaggcacat ctttgggata acagttgcag aagggaaggg   900
caaactcgta agggtcgtca agtctattta ggtggctatg ataaagagga gaaagctgct   960
agggcttatg atcttgctgc tctgaagtac tggggtgcca caacaacaac aaattttcca  1020
gtgagtaact acgaaaagga gctcgaggac atgaagcaca tgacaaggca ggagtttgta  1080
gcgtctctga aaggaagag cagtggtttc tccagaggtg catccattta caggggagtg  1140
actaggcatc accaacatgg aagatggcaa gcacggattg acgagttgc agggaacaag  1200
gatctttact tgggcacctt cagcacccag gaggaggcag cggaggcgta cgacatcgcg  1260
gcgatcaagt tccgcggcct caacgccgtc accaacttcg acatgagccg ctacgacgtg  1320
aagagcatcc tggacagcag cgccctcccc atcggcagcg ccgccaagcg cctcaaggag  1380
gccgaggccg cagcgtccgc gcagcaccac cacgccggcg tggtgagcta cgacgtcggc  1440
cgcatcgcct cgcagctcgg cgacggcgga gccctggcgg cggcgtacgg cgcgcactac  1500
cacggcgccc cctggccgac catcgcgttc agccgggcg ccgccagcac aggcctgtac  1560
cacccgtacg cgcagcagcc aatgcgcggc ggcgggtggt gcaagcagga gcaggaccac  1620
gcggtgatcg cggccgcgca cagcctgcag gacctccacc acctgaacct gggcgcggcc  1680
ggcgcgcacg acttttctc ggcagggcag caggccgccg ccgctgcgat gcacggcctg  1740
ggtagcatcg acagtgcgtc gctcgagcac agcaccggct ccaactccgt cgtctacaac  1800
ggcggggtcg gcgacagcaa cggcgccagc gccgtcggcg gcagtggcgg tggctacatg  1860
atgccgatga cgctgccgg agcaaccact acatcggcaa tggtgagcca cgagcaggtg  1920
catgcacggg cctacgacga agccaagcag gctgctcaga tggggtacga gagctacctg  1980
gtgaacgcgg agaacaatgg tggcggaagg atgtctgcat ggggggactgt cgtgtctgca  2040
gccgcggcg cagcagcaag cagcaacgac aacatggccg ccgacgtcgg ccatggcggc  2100
gcgcagctct tcagtgtctg gaacgacact taa                               2133
```

<210> SEQ ID NO 13
<211> LENGTH: 2133
<212> TYPE: DNA

```
<213> ORGANISM: Artificial sequence
<220> FEATURE:
<223> OTHER INFORMATION: Variant of Zm-ODP2 having 97.3% seq id to SEQ
      ID NO:3. The ORF encodes the aa seq set forth in SEQ ID NO:2 with
      a single aa alteration (i.e., S37 to T37).
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 13
atggccactg tgaacaactg gctcgctttc tccctctccc cgcaggagct gccgccctcc      60
caaaccacgg actccacact catctcggcc gccaccgccg accatgtcac cggcgatgtc     120
tgcttcaaca tcccccaaga ttggagcatg aggggatcag agctttcggc gctcgtcgcg     180
gagccgaaac tggaggactt cctcgggggc atttccttct ccgagcagca tcacaaggcc     240
aactgcaaca tgatacccct cactagctcc acagtttgct acgcgagctc aggtgctagc     300
accggctacc atcaccagct gtaccaccag cccacctcct cagcgctcca cttcgcggac     360
tccgtaatgg tggcctcctc ggccggtgtc cacgacggcg gtgccatgct cagcgcggcc     420
gccgctaacg gtgtcgctgg cgcagccagt gccaacgggg cggcatcgg gctgtccatg      480 attaagaact ggctgcggag ccaaccggcg cccatgcagc cgagggtggc ggcggctgag     540
ggcgcgcagg ggctctcttt gtccatgaat atggcgggga cgacccaagg cgctgcaggc     600
atgccacttc tcgctggaga gcgcgcacgg gcgcccgaga gtgtatcgac gtcagcacag     660
ggtggagccg tcgtcgtcac cgcgccgaag gaggatagcg gtggcagcgg tgttgccggc     720
gctctagtag ccgtgagcac ggacacgggt ggcagcgggg gcgcgtcggc tgacaacacg     780
gcaaggaaga cggtggacac gtttgggcag cggacgtcga tctaccgtgg cgtgacaaga     840
catagatgga ctgggagata tgaggcacat ctttgggata cagttgcag aagggaaggg      900 caaactcgta agggtcgtca agtctattta ggtggctatg ataaagagga gaaagctgct     960
agggcttatg accttgctgc tctcaagtac tgggggtgcca caacaacaac aaatttccca    1020
gtgagtaact acgaaaagga gctcgaggac atgaagcaca tgacaaggca ggagtttgta    1080
gcgtctctga aaggaagag ctccggtttc tccagaggtg catccattta caggggagtg     1140
actaggcatc accaacatgg aagatggcaa gctcggattg gacgagttgc agggaacaag    1200
gatctttacc tcggcacctt cagcacccag gaggaagctg cggaggcgta cgacatcgcg    1260
gcgatcaaat tccgcggcct caacgccgtc accaacttcg acatgagccg ctacgacgtg    1320
aagagcatcc tggacagcag cgccctgccc atcggcagcg ccgccaagcg cctgaaggag    1380
gccgaggccg cagcgtccgc gcagcaccac cacgccggcg tggtgagcta cgacgtcggg    1440
cgcatcgcct cgcagctcgg cgacggcgga gccctggcgg cggcgtatgg cgcgcactac    1500 cacggggcc cctggccgac catcgcgttc agccgggcg ccgccagcac aggcctgtac      1560 caccctacg cgcagcagcc aatgcgcggc ggcgggtggt gcaagcagga gcaggaccac    1620
gcggtgatcg cggcggcgca cagcctgcag gacctccacc acctgaacct gggcgccgcc    1680
ggcgcgcacg acttttttc ggcagggcag caggccgcc ccgcagccat gcacggcctg      1740
ggtagcatcg acagtgcgtc gctcgaacac tccaccggca gcaactccgt cgtctacaat    1800
ggcggggtcg cgacagcaa cggcgccagc ccgtcggcg ctccggcgg aggctatatg       1860 atgccgatga gcgctgccgg agcaaccaca acatcggcaa tggtgagcca cgagcaggtg    1920
```

| | |
|---|---|
| catgcacggg cctacgacga agccaagcag gctgcacaga tggggtacga gagctacctg | 1980 |
| gtgaacgcgg agaacaatgg tggcggaagg atgtctgcat gggggactgt cgtgtctgca | 2040 |
| gcggcggcgg cagcagcaag cagcaacgac aacatggccg ccgacgtcgg ccatggcggc | 2100 |
| gcgcagctct tcagtgtctg gaacgacact taa | 2133 |

<210> SEQ ID NO 14
<211> LENGTH: 2133
<212> TYPE: DNA
<213> ORGANISM: Artificial sequence
<220> FEATURE:
<223> OTHER INFORMATION: Variant of Zm-ODP2 having 91.9% seq id to SEQ
      ID NO:3. The ORF encodes the aa seq set forth in SEQ ID NO:2 with
      a single aa alteration (i.e., S37 to T37).
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 14

| | |
|---|---|
| atggccacag tgaacaactg gctcgctttt agcctgagcc cgcaggaact gccgccctcc | 60 |
| cagaccacgg actccactct catctcggcc gccaccgccg atcatgtcac cggcgacgtc | 120 |
| tgtttcaata ttccccaaga ttggtccatg aggggatcag agctttcggc gctggtcgcg | 180 |
| gaaccgaaac tggaagactt cctcggcggc atctcctttt ccgaacagca tcataaggcc | 240 |
| aactgcaaca tgatacccag cactagcagc acagtgtgct acgcgagctc aggtgcttcc | 300 |
| accggctacc accatcaact ctaccaccaa ccgacgagct cagcgctcca tttcgccgat | 360 |
| tccgtaatgg tcgcctcctc ggccggtgtc cacgacgggg gtgccatgct ctccgcggcc | 420 |
| gccgctaacg gtgtcgctgg cgctgccagt gcgaacggcg gcggcatcgg gctgagcatg | 480 |
| atcaagaatt ggctgcggag ccaaccggcg cccatgcaac cgagggtggc cgcggctgag | 540 |
| ggggcgcagg ggctgtcttt gagcatgaat atggccggga ccacgcaagg ggctgctggc | 600 |
| atgccacttc tcgctggtga gcgggcacgc gcccccgaga gtgtttcgac gtcagcacag | 660 |
| ggaggtgcgg tggtcgtcac ggcgccgaag gaggatagcg gtggcagcgg tgttgcgggc | 720 |
| gctctcgtag ccgtgagcac ggacacgggt ggcagcggcg gcgcgtcggc tgacaacacg | 780 |
| gcaaggaaga cggtggacac gttcgggcag cggacgtcga tttaccgtgg cgtgacaagg | 840 |
| catagatgga ctgggaggta tgaggcacat ctttgggata cagttgcag aagggagggg | 900 |
| caaactcgta agggtagaca ggtctacctg ggtggctatg ataaagagga aaggctgct | 960 |
| agggcttatg atcttgctgc actgaagtac tggggtgcca ctactacaac aaactttcct | 1020 |
| gtcagtaact atgaaaagga gctcgaggac atgaagcaca tgacaaggca agaatttgtt | 1080 |
| gcgtctctga aaggaagag cagtggttc tccagaggtg catccattta caggggagtg | 1140 |
| actaggcatc accaacatgg tagatggcag gcacgcattg gtcgagttgc agggaacaaa | 1200 |
| gatctgtatt tgggcacctt tagcacccaa gaggaggcag ccgaggcgta cgacatcgcg | 1260 |
| gcgatcaaat tccgcggcct caacgccgtc acgaacttcg atatgagccg ctacgacgtc | 1320 |
| aagagcatcc tggacagcag cgccctcccg atcggcagcg ccgcgaaacg cctcaaggag | 1380 |
| gccgaggccg cagcgtccgc gcagcaccac cacgccggcg tggtcagcta cgacgtcggc | 1440 |
| cgcattgcct cgcagctcgg cgacggcgga gccctggccg cggcgtacgg ggcgcactac | 1500 |

```
cacggggccg cctggccgac catcgccttt cagccgggcg ccgccagcac aggcctgtac    1560
catccgtacg cgcaacaacc aatgcgcggc ggcgggtggt gcaaacagga gcaggaccac    1620
gcggtcattg cggcggccca tagcctgcag gacctccacc acctcaacct gggcgcggcg    1680
ggcgcgcacg acttttctc ggcagggcaa caggccgcgg ccgctgcgat gcacggcctg    1740
ggtagcattg actccgcgtc gctggagcac agcacgggca gcaactccgt cgtgtacaac    1800
ggcggcgtgg cgacagcaa cggcgccagc gccgtcgggg ggagtggggg tgggtacatg    1860
atgcccatga gcgcagccgg agcaaccact actagcgcaa tggtgagcca tgagcaggtg    1920
catgcacggg cctacgacga ggccaaacag gcagcacaaa tggggtatga gagctacctg    1980
gtcaatgccg agaacaatgg tggggtagaa atgtctgcat ggggcactgt cgtgtctgca    2040
gccgcggcgg cagcagctag ctccaacgat aacatggccg ccgacgtcgg ccatggcggg    2100
gcgcaactct tttccgtgtg gaacgatact taa                                 2133

<210> SEQ ID NO 15
<211> LENGTH: 2133
<212> TYPE: DNA
<213> ORGANISM: Artificial sequence
<220> FEATURE:
<223> OTHER INFORMATION: Variant of Zm-ODP2 having 86.6% seq id to SEQ
      ID NO:3. The ORF encodes the aa seq set forth in SEQ ID NO:2 with
      a single aa alteration (i.e., S37 to T37).
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 15
atggcgactg tgaataattg gctcgctttc tccctctccc cccaggagct ccccccctcc      60
cagaccacgg atagcacact catctcggcc gccaccgcgg atcatgtcac cggcgacgtc     120
tgtttcaaca ttccgcagga ctggagcatg agaggttcag agcttagcgc gctcgtcgcg     180
gaaccgaaac tcgaggactt tctcggcggc atctccttct ccgagcagca tcacaaagcg     240
aactgtaaca tgatccccag cactagctcc actgtttgct acgccagctc aggtgctagc     300
acgggctatc atcaccagct gtatcatcag cccaccagct cagcgctgca ttttgccgat     360
agcgtaatgg tggcgtcctc ggcgggtgtg cacgacgggg gagccatgct cagcgcggcc     420
gcggctaatg tgtcgcagg cgcagcgtcc gcgaacggcg ggggcattgg gctgtccatg     480
attaaaaact ggctgcgcag ccagccggcg cccatgcaac cgagagtggc cgcggcagaa     540
ggcgcgcaag gcctctccct cagcatgaac atggccggga ccacgcaggg cgctgcaggg     600
atgccactgc tggcaggtga acgggcacgg gcgcccgaaa gtgtaagcac gtcagcacag     660 ggtgagccg tcgtcgtcac ggcgccgaag gaggactccg gtggcagcgg tgtggcgggc     720
gcactcgttg ccgtgagcac cgatacgggt ggcagcgggg cgccagcgc agacaacacc     780 gcaaggaaga cggtcgacac cttcgggcaa cggacgagca tttaccgtgg ggtgacaaga     840
cacaggtgga cagggagata tgaggctcac ctgtgggata ttcctgcag aagggagggc     900 caaactcgta agggtcgtca agtgtattta ggagggtatg ataaagagga gaaagctgct     960
agagcttatg atcttgctgc tctgaagtac tggggtgcca caactacaac aaactttcca    1020
gtgtccaact atgagaagga gctcgaagac atgaagcata tgacaggca agaatttgtt    1080 gcgtccctga ggagaaagtc cagtggattc tccagggag ctagcatcta tagggagtc    1140
```

```
acaaggcatc accaacacgg aagatggcaa gctcgcattg gtcgagttgc tggcaacaag    1200
gatctttact tgggcacgtt tagcacccaa gaggaggcag cggaagcgta tgatatcgcc    1260
gcgatcaaat tccgcgggct gaatgccgtc acgaacttcg acatgtcccg ctacgatgtg    1320
aagagcattc tcgacagcag cgcgctgccg atcgggagcg ccgcgaagcg cctgaaggaa    1380
gcggaggccg ctgcctccgc ccagcatcat cacgccgggg tggtgtccta cgatgtcggc    1440
cgcattgcct cgcagctcgg ggacggggga cccctcgcgg ccgcgtacgg cgcccactat    1500
cacggcgccg cctggccgac catcgcgttc aaccgggcg cggccagcac tgggctctat    1560
catccgtatg cccagcaacc tatgcgcggc ggcgggtggt gcaaacagga gcaagatcac    1620
gccgtcattg cggcggcgca cagcctccag gacctgcatc acctgaacct gggcgcggcg    1680
ggcgcgcatg acttttctc ggctgggcag caagccgcgg ccgcagcgat gcatggcctg    1740
ggttccatcg attccgcgtc gctggagcac agcaccggct ccaactccgt cgtgtataac    1800
ggcggcgtgg gggacagcaa tggcgcgagc gcggtggggg gcagtggcgg tggctatatg    1860
atgcccatgt ccgctgccgg agctaccact acttcggcaa tggtgtccca cgagcaggtg    1920
catgctcgcg cctacgacga agcgaagcag gcagctcaaa tgggctatga aagctacctc    1980
gtgaatgcgg aaaacaacgg aggcggaagg atgtctgcat ggggcactgt cgtgtccgca    2040
gccgccgcgg ctgctgctag cagcaacgac aatatggccg ccgacgtcgg ccatggcggc    2100
gcgcagctct tcagtgtgtg gaatgatact taa                                2133
```

<210> SEQ ID NO 16
<211> LENGTH: 2133
<212> TYPE: DNA
<213> ORGANISM: Artificial sequence
<220> FEATURE:
<223> OTHER INFORMATION: Variant of Zm-ODP2 having 81.5% seq id to SEQ
      ID NO:3. The ORF encodes the aa seq set forth in SEQ ID NO:2 with
      a single aa alteration (i.e., S37 to T37).
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 16

```
atggcgactg tcaacaattg gctggcattc agcctgtccc cccaagagct gcccccgagc      60
caaacgaccg cacagcacact catctcggcc gcgaccgcgg accacgtcac gggcgacgtc     120
tgcttcaata ttccgcagga ctggagcatg aggggttcag agctgtcggc gctggtggcg     180
gaacccaagc tcgaagattt cctcgggggg atcagcttta gcgagcagca tcataaagcg     240
aactgcaata tgatcccctc cactagctcc actgtttgtt atgcgtcctc aggagcaagc     300
acggggtacc accatcaact gtatcaccaa ccgacgtcct cagccctcca tttcgccgac     360
tccgttatgg tcgccagctc ggcgggtgtg catgacgggg gtgcgatgct cagcgccgcc     420
gccgctaatg gtgtcgcagg cgctgcgtcc gccaacgggg gggatcgg cctgtccatg       480 attaagaatt ggctgcgctc ccaaccggcc cccatgcagc ccagagtggc cgccgcagaa     540 gggcccagg gcctctctct ctccatgaat atggcgggga ccacgcaggg ggcagcaggc      600
atgcctctgc tggctggaga acgcgcacg gcccccgaga gtgttagcac gagcgctcag     660
ggtggtgccg tggtggtgac cgccccgaaa gaggactccg gaggctccgg agttgccggc     720
```

```
gctctagttg ccgtgagcac ggatacgggt ggctccggcg gggcgagcgc tgataatacc      780
gcaagaaaga ccgtcgacac ctttgggcag cgcacgtcga tctacagagg cgtcactaga      840
cataggtgga caggcagata cgaagcacac ctttgggata acagttgtag gagggaaggc      900
caaacacgta aaggtagaca agtctattta ggaggctacg ataaggaaga gaaggctgca      960
agggcatacg accttgctgc actcaagtat tggggtgcca caactactac aaactttcca     1020
gtgagtaact acgaaaaaga actcgaggat atgaaacaca tgactaggca ggagtttgta     1080
gcctccctca gaagaaaatc ctccggattt agcagggtg cttccattta cagaggagtg      1140
acaagacacc accagcatgg taggtggcag gcacggattg gacgagtggc aggcaacaaa     1200
gacctttatc tcggcacctt tagcacgcag gaagaggcag cggaggcgta cgacattgcc     1260
gcgattaaat tccggggcct caatgcggtc acgaactttg atatgtcccg ctatgatgtg     1320
aaaagcatcc tcgacagcag cgccctcccc attggcagcg cggcgaaacg gctcaaagaa     1380
gcggaagcgg ctgccagcgc ccagcaccat catgccgggg tggtcagcta cgatgtgggg     1440
cgcatcgcga gccaactggg cgatgggggt gccctcgccg cggcctatgg cgcccattac     1500
catggcgccg cgtggccgac catcgccttc caacccggcg ccgccagcac tggcctctac     1560 caccccctatg cccaacaacc aatgcgcggc ggcggctggt gtaagcagga gcaagatcat    1620
gccgtgattg cggcggcgca ctccctccag gacctgcatc acctgaatct gggcgccgcg     1680
ggggcccatg atttctttag cgctgggcag caagcggccg ccgcagccat gcacgggctc     1740
ggtagcattg acagtgcctc gctggaacat agcacgggga gcaactccgt ggtctacaac     1800
gggggcgtgg gcgatagcaa cggcgccagc gcggtgggcg gcagtggcgg tggctatatg     1860
atgccgatga gcgctgcggg agctacgaca actagcgcaa tggtctccca cgagcaagtc     1920
cacgctcgcg cgtatgatga agccaaacag gcagctcaga tgggctacga atcctacctg     1980
gtgaatgccg aaaataacgg tggcggaaga atgtccgctt ggggcacagt ggtgtctgca     2040
gccgccgcgc ctgctgcatc cagcaatgac aacatggcgg ccgacgtggg ccatggcggg     2100
gcgcaactct ttagtgtctg gaatgacact taa                                  2133
```

<210> SEQ ID NO 17
<211> LENGTH: 2133
<212> TYPE: DNA
<213> ORGANISM: Artificial sequence
<220> FEATURE:
<223> OTHER INFORMATION: Variant of Zm-ODP2 having 75.9% seq id to SEQ
      ID NO:3.  The ORF encodes the aa seq forth in SEQ ID NO:2 with a
      single aa alteration (i.e., S37 to T37).
<220> FEATURE:
<221> NAME/KEY: misc_feature
<222> LOCATION: (0)..(0)
<223> OTHER INFORMATION: Synthesized
<220> FEATURE:
<221> NAME/KEY: misc_feature
<222> LOCATION: (1)..(2133)
<223> OTHER INFORMATION: CDS

<400> SEQUENCE: 17

```
atggcgactg tcaataattg gctggcattc agcctgagcc cgcaagagct gccccgtcc       60 caaacgacgg attccactct gattagcgcg gccacgccg atcacgtgac ggggacgtg       120 tgttttaaca ttccccagga ttggtccatg agaggatcag agctgtcggc cctggtggcc    180
gagccgaaac tcgaagattt tctcggcggg attagcttta gcgaacaaca ccataaagcg    240
aactgcaaca tgatccccag cacatcctcc actgtttgct atgccagcag cggagcatcc    300
accgggtatc accatcaact ctatcatcag cccacgagca gcgccctgca ctttgccgat    360
```

```
agcgtaatgg tcgcgagcag cgcgggtgtg catgacgggg gagcgatgct gtccgccgcg    420
gcggctaatg gtgtggcagg ggcagcgagt gccaatgggg ggggcattgg cctcagcatg    480
atcaaaaact ggctccgctc ccaaccggcg cccatgcagc ccagagtcgc ggccgcagaa    540
ggcgcccaag gcctgtccct cagcatgaat atggcgggca ccacgcaggg ggctgcaggg    600
atgcctctgc tggctggtga gcgggctcgc gccccggaaa gtgtatcgac cagcgctcaa    660
ggtggtgccg tcgtggtgac cgcccccaaa gaggacagcg gtgggtccgg agtggcgggg    720
gcactcgttg cggtgtccac cgataccgga gggagcgggg gggcctcggc agataacacc    780
gctagaaaga ccgtcgacac ctttggccag cggacgagca tctacagagg cgtcacaaga    840
cacagatgga ctgcaggta cgaagcacac ctttgggaca acagttgtag gagagagggc    900
caaacaagaa aaggaagaca ggtgtattta ggaggctacg acaaggaaga aaaggcagca    960
agggcatatg acctggcagc actcaaatat tggggagcca ctacaactac aaactttcct   1020
gtcagtaact acgaaaaaga actcgaggat atgaaacaca tgactagaca ggaattcgta   1080
gcctccctca ggagaaagtc cagtggattc agcagaggag catccatcta tagaggtgtg   1140
actagacacc accaacacgg taggtggcaa gctcgcatcg gtcgcgtggc tggcaataaa   1200
gatctgtatc tcgggacctt tagcacgcaa gaagaggctg ccgaagccta cgacattgcg   1260
gccattaaat ttcgcgggct caatgcggtc accaactttg atatgtcccg ctacgatgtg   1320
aagtccatcc tcgacagctc cgccctcccg atcgggtccg ccgcgaaacg cctgaaagag   1380
gcggaagcgg ctgcctccgc ccaacatcat catgcggggg tcgtctccta cgacgtgggc   1440
cggatcgcga gccagctggg ggatggcggt gcgctggccg ccgcctatgg cgcccactat   1500
cacggggcgg cgtggcccac gattgcgttt caaccggggg cggcgagcac tgggctgtac   1560
catccctatg cgcaacaacc aatgcgcggg gggggctggt gcaaacaaga acaggatcat   1620
gccgtcattg ccgcggcgca cagcctgcaa gacctccatc atctcaacct cggcgccgcg   1680
ggcgcgcacg atttcttctc ggctgggcag caagcggccg cggctgccat gcatggcctc   1740
ggatccatcg actccgccag cctggaacac agcaccgggt ccaacagcgt cgtgtataac   1800
gggggggtcg gggactccaa tggcgcgagc gcggtggggg ggagtggcgg agggtatatg   1860
atgcccatga gcgctgcggg agctacgaca acatcggcta tggtcagcca tgaacaagtc   1920
catgctcggg cctatgatga ggcgaaacaa gcagcacaaa tggggtacga gtcctatctc   1980
gtcaatgccg aaaataatgg tggcggaagg atgtccgcat gggggacagt ggtctccgct   2040
gccgcggcgc ctgcagcttc ctccaatgat aatatggcgg cggatgtcgg gcacgggggg   2100
gcccagctgt tttccgtgtg gaacgatact taa                                2133
```

<210> SEQ ID NO 18
<211> LENGTH: 2133
<212> TYPE: DNA
<213> ORGANISM: Artificial sequence
<220> FEATURE:
<223> OTHER INFORMATION: Variant of Zm-ODP2 having 70.4% seq id to SEQ
      ID NO:3. The ORF encodes the aa seq set forth in SEQ ID NO:2 with
      a single aa alteration (i.e., S37 to T37).
<220> FEATURE:
<221> NAME/KEY: misc_feature
<222> LOCATION: (0)..(0)
<223> OTHER INFORMATION: synthesized
<220> FEATURE:
<221> NAME/KEY: misc_feature
<222> LOCATION: (1)..(2133)
<223> OTHER INFORMATION: CDS

<400> SEQUENCE: 18

```
atggcgacag tgaataattg gctggcattt agcctgagcc cgcaagaact cccgccgagc      60
caaaccaccg attccactct gatttcggcg gccaccgcgg accacgtgac gggggacgtg     120
tgtttcaata ttccgcaaga ctggtccatg agaggaagcg aactgagcgc cctggtggcc     180
gaacccaaac tcgaagactt tctgggggggg attagcttca gcgaacaaca ccataaggcc     240
aattgtaata tgatcccgtc acttcctcc actgtgtgtt atgcctccag cggagcaagc      300
acgggctatc accatcagct ctaccatcaa ccgacgtcct cagccctcca ctttgccgat     360
agcgttatgg tcgcgagcag cgcgggtgtg catgatgggg gagcgatgct gtccgccgcg     420
gcggcaaatg gagtggcagg ggcagccagt gcgaatgggg ggggattgg cctcagcatg      480
atcaagaatt ggctccgctc ccaaccggcc cccatgcaac cgagagtcgc cgccgcagaa     540
ggggcccaag gcctgtccct cagcatgaac atggccggga cgacgcaggg ggcagcaggg     600
atgcctctgc tggcaggaga acgggcacgc gccccggaaa gtgttagcac cagcgctcaa     660
ggaggtgcgg tggtggtgac cgcccccaag gaagattccg gagggtccgg agtggcgggg     720
gcactcgttg cggtctccac cgataccggt gggtccgggg gggccagcgc agataatacc     780
gctagaaaaa ccgtcgatac cttttggccaa cgcaccagca tctacagagg ggtcactaga     840
cacaggtgga caggcagata cgaagctcac ctgtgggaca atagttgtag gagagagggc     900
cagacaagaa aaggtagaca ggtgtacctg ggaggctacg acaagaagaa aaaggctgca     960
agagcatacg acctggcagc tctcaaatac tggggagcga caactacaac taacttccct    1020
gtctccaatt atgagaaaga gctcgaagat atgaagcata tgactagaca agaatttgtt    1080
gcgtccctca ggagaaaatc cagtggattt agcaggggag ctagcatcta tagaggtgtg    1140
acaagacacc accagcacgg taggtggcaa gctcgcatcg gacgcgtggc tggcaataaa    1200
gacctttatc tcgggacgtt ttccacgcaa gaagaagctg ccgaagccta cgatattgcc    1260
gccattaaat ttcgggggct gaatgccgtg acgaactttg atatgtcccg gtatgatgtc    1320
aaatccattc tcgattcctc cgcgctgccg atcgggagcg ccgcgaaacg gctcaaggag    1380
gcggaagcgg cagccagcgc ccagcatcat cacgcgggcg tcgtgtccta tgacgtgggg    1440
cgcatcgcca gccaactggg ggatgggggt gcgctcgccg ccgcctatgg cgcccattat    1500
catggggcg cgtggcccac cattgcgttt cagcccgggg cggcgtccac tggcctctat    1560
catccctatg cgcaacaacc tatgcggggg ggggggtggt gtaaacaaga acaagaccat    1620
gcggtcattg ccgcggccca ttccctccaa gatctgcatc atctgaacct cggggccgcc    1680
ggggcccatg attttttag cgctggccaa caggcggcg cggctgccat gcatgggctc    1740
ggatccattg atagtgcgag cctggaacat tccacgggt ccaacagcgt ggtgtataat    1800
gggggcgtgg gcgatagcaa tggcgcgtcc gcggtcgggg gctccggggg tgggtatatg    1860
atgcccatgt ccgctgccgg tgctacgaca acttcggcta tggtctccca tgaacaagtc    1920
cacgctcgcg cctatgatga ggcgaaacaa gcagcacaga tgggctatga atcctatctc    1980
gtcaatgccg aaaataatgg aggggggtaga atgtccgctt ggggcactgt ggtctccgct    2040
gcggccgccg ctgcagcttc ctccaatgat aacatggcgg cggacgtggg gcacggcggg    2100
gcccaactct ttagtgtgtg gaatgataca taa                                 2133
```

<210> SEQ ID NO 19
<211> LENGTH: 710
<212> TYPE: PRT
<213> ORGANISM: Artificial sequence

```
<220> FEATURE:
<223> OTHER INFORMATION: Variant of Zm-ODP2 polypeptide having the amino
      acid sequence set forth in SEQ ID NO:2 with a single amino acid
      alteration (i.e., S37 to T37).
<220> FEATURE:
<221> NAME/KEY: MISC_FEATURE
<222> LOCATION: (0)..(0)
<223> OTHER INFORMATION: synthesized

<400> SEQUENCE: 19
```

| Met | Ala | Thr | Val | Asn | Asn | Trp | Leu | Ala | Phe | Ser | Leu | Ser | Pro | Gln | Glu |
|---|---|---|---|---|---|---|---|---|---|---|---|---|---|---|---|
| 1 | | | | 5 | | | | | 10 | | | | | 15 | |

| Leu | Pro | Pro | Ser | Gln | Thr | Thr | Asp | Ser | Thr | Leu | Ile | Ser | Ala | Ala | Thr |
|---|---|---|---|---|---|---|---|---|---|---|---|---|---|---|---|
| | | | 20 | | | | | 25 | | | | | 30 | | |

| Ala | Asp | His | Val | Thr | Gly | Asp | Val | Cys | Phe | Asn | Ile | Pro | Gln | Asp | Trp |
|---|---|---|---|---|---|---|---|---|---|---|---|---|---|---|---|
| | | 35 | | | | | 40 | | | | | 45 | | | |

| Ser | Met | Arg | Gly | Ser | Glu | Leu | Ser | Ala | Leu | Val | Ala | Glu | Pro | Lys | Leu |
|---|---|---|---|---|---|---|---|---|---|---|---|---|---|---|---|
| | 50 | | | | | 55 | | | | | 60 | | | | |

| Glu | Asp | Phe | Leu | Gly | Gly | Ile | Ser | Phe | Ser | Glu | Gln | His | His | Lys | Ala |
|---|---|---|---|---|---|---|---|---|---|---|---|---|---|---|---|
| 65 | | | | | 70 | | | | | 75 | | | | | 80 |

| Asn | Cys | Asn | Met | Ile | Pro | Ser | Thr | Ser | Ser | Thr | Val | Cys | Tyr | Ala | Ser |
|---|---|---|---|---|---|---|---|---|---|---|---|---|---|---|---|
| | | | | 85 | | | | | 90 | | | | | 95 | |

| Ser | Gly | Ala | Ser | Thr | Gly | Tyr | His | His | Gln | Leu | Tyr | His | Gln | Pro | Thr |
|---|---|---|---|---|---|---|---|---|---|---|---|---|---|---|---|
| | | | 100 | | | | | 105 | | | | | 110 | | |

| Ser | Ser | Ala | Leu | His | Phe | Ala | Asp | Ser | Val | Met | Val | Ala | Ser | Ser | Ala |
|---|---|---|---|---|---|---|---|---|---|---|---|---|---|---|---|
| | | 115 | | | | | 120 | | | | | 125 | | | |

| Gly | Val | His | Asp | Gly | Gly | Ala | Met | Leu | Ser | Ala | Ala | Ala | Ala | Asn | Gly |
|---|---|---|---|---|---|---|---|---|---|---|---|---|---|---|---|
| | 130 | | | | | 135 | | | | | 140 | | | | |

| Val | Ala | Gly | Ala | Ala | Ser | Ala | Asn | Gly | Gly | Gly | Ile | Gly | Leu | Ser | Met |
|---|---|---|---|---|---|---|---|---|---|---|---|---|---|---|---|
| 145 | | | | | 150 | | | | | 155 | | | | | 160 |

| Ile | Lys | Asn | Trp | Leu | Arg | Ser | Gln | Pro | Ala | Pro | Met | Gln | Pro | Arg | Val |
|---|---|---|---|---|---|---|---|---|---|---|---|---|---|---|---|
| | | | | 165 | | | | | 170 | | | | | 175 | |

| Ala | Ala | Ala | Glu | Gly | Ala | Gln | Gly | Leu | Ser | Leu | Ser | Met | Asn | Met | Ala |
|---|---|---|---|---|---|---|---|---|---|---|---|---|---|---|---|
| | | | 180 | | | | | 185 | | | | | 190 | | |

| Gly | Thr | Thr | Gln | Gly | Ala | Ala | Gly | Met | Pro | Leu | Leu | Ala | Gly | Glu | Arg |
|---|---|---|---|---|---|---|---|---|---|---|---|---|---|---|---|
| | | 195 | | | | | 200 | | | | | 205 | | | |

| Ala | Arg | Ala | Pro | Glu | Ser | Val | Ser | Thr | Ser | Ala | Gln | Gly | Gly | Ala | Val |
|---|---|---|---|---|---|---|---|---|---|---|---|---|---|---|---|
| | 210 | | | | | 215 | | | | | 220 | | | | |

| Val | Val | Thr | Ala | Pro | Lys | Glu | Asp | Ser | Gly | Gly | Ser | Gly | Val | Ala | Gly |
|---|---|---|---|---|---|---|---|---|---|---|---|---|---|---|---|
| 225 | | | | | 230 | | | | | 235 | | | | | 240 |

| Ala | Leu | Val | Ala | Val | Ser | Thr | Asp | Thr | Gly | Gly | Ser | Gly | Gly | Ala | Ser |
|---|---|---|---|---|---|---|---|---|---|---|---|---|---|---|---|
| | | | | 245 | | | | | 250 | | | | | 255 | |

| Ala | Asp | Asn | Thr | Ala | Arg | Lys | Thr | Val | Asp | Thr | Phe | Gly | Gln | Arg | Thr |
|---|---|---|---|---|---|---|---|---|---|---|---|---|---|---|---|
| | | | 260 | | | | | 265 | | | | | 270 | | |

| Ser | Ile | Tyr | Arg | Gly | Val | Thr | Arg | His | Arg | Trp | Thr | Gly | Arg | Tyr | Glu |
|---|---|---|---|---|---|---|---|---|---|---|---|---|---|---|---|
| | | 275 | | | | | 280 | | | | | 285 | | | |

| Ala | His | Leu | Trp | Asp | Asn | Ser | Cys | Arg | Arg | Glu | Gly | Gln | Thr | Arg | Lys |
|---|---|---|---|---|---|---|---|---|---|---|---|---|---|---|---|
| | 290 | | | | | 295 | | | | | 300 | | | | |

| Gly | Arg | Gln | Val | Tyr | Leu | Gly | Gly | Tyr | Asp | Lys | Glu | Glu | Lys | Ala | Ala |
|---|---|---|---|---|---|---|---|---|---|---|---|---|---|---|---|
| 305 | | | | | 310 | | | | | 315 | | | | | 320 |

| Arg | Ala | Tyr | Asp | Leu | Ala | Ala | Leu | Lys | Tyr | Trp | Gly | Ala | Thr | Thr | Thr |
|---|---|---|---|---|---|---|---|---|---|---|---|---|---|---|---|
| | | | | 325 | | | | | 330 | | | | | 335 | |

| Thr | Asn | Phe | Pro | Val | Ser | Asn | Tyr | Glu | Lys | Glu | Leu | Glu | Asp | Met | Lys |
|---|---|---|---|---|---|---|---|---|---|---|---|---|---|---|---|
| | | | 340 | | | | | 345 | | | | | 350 | | |

| His | Met | Thr | Arg | Gln | Glu | Phe | Val | Ala | Ser | Leu | Arg | Arg | Lys | Ser | Ser |
|---|---|---|---|---|---|---|---|---|---|---|---|---|---|---|---|
| | | 355 | | | | | 360 | | | | | 365 | | | |

```
Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Ala Leu Ala Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
                565                 570                 575

Met His Gly Leu Gly Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605

Ala Ser Ala Val Gly Gly Ser Gly Gly Gly Tyr Met Met Pro Met Ser
    610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Arg Met Ser
            660                 665                 670

Ala Trp Gly Thr Val Val Ser Ala Ala Ala Ala Ala Ala Ser Ser
        675                 680                 685

Asn Asp Asn Met Ala Ala Asp Val Gly His Gly Gly Ala Gln Leu Phe
    690                 695                 700

Ser Val Trp Asn Asp Thr
705                 710

<210> SEQ ID NO 20
<211> LENGTH: 710
<212> TYPE: PRT
<213> ORGANISM: Artificial sequence
<220> FEATURE:
<223> OTHER INFORMATION: Variant of Zm-ODP2 having 97.3% amino acid
      sequence identity to SEQ ID NO:2 (Zm-ODP2).
<220> FEATURE:
<221> NAME/KEY: MISC_FEATURE
<222> LOCATION: (0)..(0)
<223> OTHER INFORMATION: Synthesized
```

<400> SEQUENCE: 20

```
Met Ala Thr Val Asn Asn Trp Leu Ala Phe Ser Leu Ser Pro Gln Glu
1               5                   10                  15

Ile Pro Pro Ser Gln Thr Thr Asp Ser Thr Ile Leu Ser Ala Ala Thr
            20                  25                  30

Ala Asp His Val Ser Gly Asp Val Cys Phe Asn Leu Pro Gln Asp Trp
        35                  40                  45

Ser Met Arg Gly Ser Glu Ile Ser Ala Ile Val Ala Glu Pro Lys Ile
    50                  55                  60

Glu Asp Phe Ile Gly Gly Leu Ser Phe Ser Glu Gln His His Lys Ala
65                  70                  75                  80

Asn Cys Asn Met Leu Pro Ser Thr Ser Ser Thr Val Cys Tyr Ala Ser
                85                  90                  95

Ser Gly Ala Ser Thr Gly Tyr His His Gln Ile Tyr His Gln Pro Thr
            100                 105                 110

Ser Ser Ala Ile His Phe Ala Asp Ser Val Met Val Ala Ser Ser Ala
        115                 120                 125

Gly Val His Asp Gly Gly Ala Met Ile Ser Ala Ala Ala Asn Gly
    130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Ile Ser Ile Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Gly Ser Gly Val Ala Gly
225                 230                 235                 240

Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
```

-continued

```
                405                 410                 415
Tyr Asp Ile Ala Ala Ile Lys Phe Arg Gly Leu Asn Ala Val Thr Asn
            420                 425                 430
Phe Asp Met Ser Arg Tyr Asp Val Lys Ser Ile Leu Asp Ser Ser Ala
        435                 440                 445
Leu Pro Ile Gly Ser Ala Ala Lys Arg Leu Lys Glu Ala Glu Ala Ala
    450                 455                 460
Ala Ser Ala Gln His His His Ala Gly Val Val Ser Tyr Asp Val Gly
465                 470                 475                 480
Arg Val Ala Ser Gln Leu Gly Asp Gly Ala Leu Ala Ala Ala Ala Tyr
                485                 490                 495
Gly Ala His Tyr His Gly Ala Ala Trp Pro Thr Val Ala Phe Gln Pro
            500                 505                 510
Gly Ala Ala Ser Thr Gly Leu Tyr His Pro Tyr Ala Gln Gln Pro Met
        515                 520                 525
Arg Gly Gly Gly Trp Cys Lys Gln Glu Gln Asp His Ala Val Val Ala
    530                 535                 540
Ala Ala His Ser Leu Gln Asp Leu His His Leu Asn Leu Gly Ala Ala
545                 550                 555                 560
Gly Ala His Asp Phe Phe Ser Ala Gly Gln Gln Ala Ala Ala Ala Ala
                565                 570                 575
Met His Gly Leu Gly Ser Val Asp Ser Ala Ser Leu Glu His Ser Thr
            580                 585                 590
Gly Ser Asn Ser Val Val Tyr Asn Gly Gly Val Gly Asp Ser Asn Gly
        595                 600                 605
Ala Ser Ala Val Gly Gly Ser Gly Gly Gly Tyr Met Met Pro Met Ser
    610                 615                 620
Ala Ala Gly Ala Thr Thr Thr Ser Ala Met Val Ser His Glu Gln Val
625                 630                 635                 640
His Ala Arg Ala Tyr Asp Glu Ala Lys Gln Ala Ala Gln Met Gly Tyr
                645                 650                 655
Glu Ser Tyr Leu Val Asn Ala Glu Asn Asn Gly Gly Gly Arg Met Ser
            660                 665                 670
Ala Trp Gly Thr Val Val Ser Ala Ala Ala Ala Ala Ala Ala Ser Ser
        675                 680                 685
Asn Asp Asn Met Ala Ala Asp Val Gly His Gly Gly Ala Gln Leu Phe
    690                 695                 700
Ser Val Trp Asn Asp Thr
705                 710
```

<210> SEQ ID NO 21
<211> LENGTH: 710
<212> TYPE: PRT
<213> ORGANISM: Artificial sequence
<220> FEATURE:
<223> OTHER INFORMATION: Variant of Zm-ODP2 having 92.4% amino acid
      sequence identity to SEQ ID NO:2 (Zm-ODP2).
<220> FEATURE:
<221> NAME/KEY: MISC_FEATURE
<222> LOCATION: (0)..(0)
<223> OTHER INFORMATION: Synthesized

<400> SEQUENCE: 21

```
Met Ala Thr Ile Asn Asn Trp Leu Ala Phe Ser Leu Ser Pro Gln Glu
1               5                   10                  15
Ile Pro Pro Ser Gln Thr Thr Asp Ser Thr Ile Leu Ser Ala Ala Thr
            20                  25                  30
```

-continued

```
Ala Asp His Ile Ser Gly Asp Val Cys Phe Asn Leu Pro Gln Asp Trp
        35                  40                  45

Ser Met Arg Gly Ser Glu Ile Ser Ala Ile Ile Ala Glu Pro Lys Ile
    50                  55                  60

Glu Asp Phe Ile Gly Gly Leu Ser Phe Ser Glu Gln His His Lys Ala
65                  70                  75                  80

Asn Cys Asn Met Leu Pro Ser Thr Ser Ser Thr Ile Cys Tyr Ala Ser
                85                  90                  95

Ser Gly Ala Ser Thr Gly Tyr His His Gln Ile Tyr His Gln Pro Thr
                100                 105                 110

Ser Ser Ala Ile His Phe Ala Asp Ser Ile Met Ile Ala Ser Ser Ala
            115                 120                 125

Gly Ile His Asp Gly Gly Ala Met Ile Ser Ala Ala Ala Asn Gly
        130                 135                 140

Ile Ala Gly Ala Ala Ser Ala Asn Gly Gly Gly Ile Gly Leu Ser Met
145                 150                 155                 160

Ile Lys Asn Trp Leu Arg Ser Gln Pro Ala Pro Met Gln Pro Arg Ile
                165                 170                 175

Ala Ala Ala Glu Gly Ala Gln Gly Ile Ser Ile Ser Met Asn Met Ala
            180                 185                 190

Gly Thr Thr Gln Gly Ala Ala Gly Met Pro Ile Val Ala Gly Glu Arg
        195                 200                 205

Ala Arg Ala Pro Glu Ser Ile Ser Thr Ser Ala Gln Gly Gly Ala Ile
    210                 215                 220

Ile Ile Thr Ala Pro Lys Glu Asp Ser Gly Ser Gly Leu Ala Gly
225                 230                 235                 240

Ala Val Leu Ala Leu Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445
```

```
Leu Pro Ile Gly Ser Ala Ala Lys Arg Leu Lys Glu Ala Glu Ala Ala
    450                 455                 460

Ala Ser Ala Gln His His His Ala Gly Leu Leu Ser Tyr Asp Leu Gly
465                 470                 475                 480

Arg Val Ala Ser Gln Val Gly Asp Gly Ala Val Ala Ala Ala Tyr
                485                 490                 495

Gly Ala His Tyr His Gly Ala Ala Trp Pro Thr Val Ala Phe Gln Pro
            500                 505                 510

Gly Ala Ala Ser Thr Gly Val Tyr His Pro Tyr Ala Gln Gln Pro Met
            515                 520                 525

Arg Gly Gly Gly Trp Cys Lys Gln Glu Gln Asp His Ala Leu Val Ala
530                 535                 540

Ala Ala His Ser Val Gln Asp Val His His Val Asn Val Gly Ala Ala
545                 550                 555                 560

Gly Ala His Asp Phe Phe Ser Ala Gly Gln Gln Ala Ala Ala Ala Ala
            565                 570                 575

Met His Gly Val Gly Ser Val Asp Ser Ala Ser Val Glu His Ser Thr
            580                 585                 590

Gly Ser Asn Ser Val Val Tyr Asn Gly Leu Gly Asp Ser Asn Gly
    595                 600                 605

Ala Ser Ala Leu Gly Gly Ser Gly Gly Gly Tyr Met Met Pro Met Ser
610                 615                 620

Ala Ala Gly Ala Thr Thr Thr Ser Ala Met Leu Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Gly Arg Met Ser
            660                 665                 670

Ala Trp Gly Thr Val Val Ser Ala Ala Ala Ala Ala Ala Ser Ser
            675                 680                 685

Asn Asp Asn Met Ala Ala Asp Val Gly His Gly Ala Gln Leu Phe
    690                 695                 700

Ser Val Trp Asn Asp Thr
705                 710

<210> SEQ ID NO 22
<211> LENGTH: 710
<212> TYPE: PRT
<213> ORGANISM: Artificial sequence
<220> FEATURE:
<223> OTHER INFORMATION: Variant of Zm-ODP2 having 87.3% amino acid
      sequence identity to SEQ ID NO:2 (Zm-ODP2).
<220> FEATURE:
<221> NAME/KEY: MISC_FEATURE
<222> LOCATION: (0)..(0)
<223> OTHER INFORMATION: Synthesized

<400> SEQUENCE: 22

Met Ala Thr Ile Asn Asn Trp Leu Ala Phe Ser Leu Ser Pro Gln Glu
1               5                   10                  15

Ile Pro Pro Ser Gln Thr Thr Asp Ser Thr Ile Leu Ser Gly Gly Thr
                20                  25                  30

Ala Asp His Ile Ser Gly Asp Val Cys Phe Asn Leu Pro Gln Asp Trp
            35                  40                  45

Ser Met Arg Gly Ser Glu Ile Ser Gly Ile Ile Gly Glu Pro Lys Ile
        50                  55                  60

Glu Asp Phe Ile Gly Gly Leu Ser Phe Ser Glu Gln His His Lys Gly
```

-continued

```
                65                  70                  75                  80
Asn Cys Asn Met Leu Pro Ser Thr Ser Ser Thr Ile Cys Tyr Gly Ser
                    85                  90                  95

Ser Gly Gly Ser Thr Gly Tyr His His Gln Ile Tyr His Gln Pro Thr
                100                 105                 110

Ser Ser Gly Ile His Phe Gly Asp Ser Ile Met Ile Gly Ser Ser Gly
                115                 120                 125

Gly Ile His Asp Gly Gly Met Ile Ser Gly Gly Gly Asn Gly
            130                 135                 140

Ile Gly Gly Gly Ser Gly Asn Gly Gly Ile Gly Leu Ser Met
145                 150                 155                 160

Ile Lys Asn Trp Leu Arg Ser Gln Pro Gly Pro Met Gln Pro Arg Ile
                165                 170                 175

Gly Gly Gly Glu Gly Gly Gln Gly Ile Ser Ile Ser Met Asn Met Gly
                180                 185                 190

Gly Thr Thr Gln Gly Gly Gly Met Pro Ile Val Gly Gly Glu Arg
                195                 200                 205

Gly Arg Gly Pro Glu Ser Ile Ser Thr Ser Gly Gln Gly Gly Ile
            210                 215                 220

Ile Ile Thr Ala Pro Lys Glu Asp Ser Gly Ser Gly Leu Ala Gly
225                 230                 235                 240

Ala Val Leu Ala Leu Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
                260                 265                 270

Ser Ile Tyr Arg Gly Val Thr Arg His Arg Trp Thr Gly Arg Tyr Glu
                275                 280                 285

Ala His Leu Trp Asp Asn Ser Cys Arg Arg Glu Gly Gln Thr Arg Lys
            290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
                340                 345                 350

His Met Thr Arg Gln Glu Phe Val Ala Ser Leu Arg Arg Lys Ser Ser
            355                 360                 365

Gly Phe Ser Arg Gly Ala Ser Ile Tyr Arg Gly Val Thr Arg His His
            370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
                420                 425                 430

Phe Asp Met Ser Arg Tyr Asp Val Lys Ser Ile Leu Asp Ser Ser Ala
                435                 440                 445

Leu Pro Ile Gly Ser Ala Ala Lys Arg Leu Lys Glu Ala Glu Ala Ala
                450                 455                 460

Ala Ser Ala Gln His His His Ala Gly Leu Leu Ser Tyr Asp Leu Gly
465                 470                 475                 480

Arg Val Ala Ser Gln Val Gly Asp Gly Gly Ala Val Ala Ala Ala Tyr
                485                 490                 495
```

Gly Ala His Tyr His Gly Ala Ala Trp Pro Thr Val Ala Phe Gln Pro
                500                 505                 510

Gly Ala Ala Ser Thr Gly Val Tyr His Pro Tyr Ala Gln Gln Pro Met
            515                 520                 525

Arg Gly Gly Trp Cys Lys Gln Glu Gln Asp His Ala Leu Val Ala
        530                 535                 540

Ala Ala His Ser Val Gln Asp Val His Val Asn Val Gly Ala Ala
545                 550                 555                 560

Gly Ala His Asp Phe Phe Ser Ala Gly Gln Gln Ala Ala Ala Ala
            565                 570                 575

Met His Gly Val Gly Ser Val Asp Ser Ala Ser Val Glu His Ser Thr
                580                 585                 590

Gly Ser Asn Ser Val Val Tyr Asn Gly Leu Gly Asp Ser Asn Gly
        595                 600                 605

Ala Ser Ala Leu Gly Gly Ser Gly Gly Gly Tyr Met Met Pro Met Ser
        610                 615                 620

Ala Ala Gly Ala Thr Thr Thr Ser Ala Met Leu Ser His Glu Gln Leu
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Gly Arg Met Ser
            660                 665                 670

Ala Trp Gly Thr Leu Leu Ser Ala Ala Ala Ala Ala Ala Ser Ser
        675                 680                 685

Asn Asp Asn Met Ala Ala Asp Val Gly His Gly Gly Ala Gln Leu Phe
            690                 695                 700

Ser Val Trp Asn Asp Thr
705                 710

<210> SEQ ID NO 23
<211> LENGTH: 710
<212> TYPE: PRT
<213> ORGANISM: Artificial sequence
<220> FEATURE:
<223> OTHER INFORMATION: Variant of Zm-ODP2 having 82.4% amino acid
      sequence identity to SEQ ID NO:2 (Zm-ODP2).
<220> FEATURE:
<221> NAME/KEY: MISC_FEATURE
<222> LOCATION: (0)..(0)
<223> OTHER INFORMATION: synthesized

<400> SEQUENCE: 23

Met Ala Thr Ile Asn Asn Trp Leu Ala Phe Ser Leu Ser Pro Gln Glu
1               5                   10                  15

Ile Pro Pro Ser Gln Thr Thr Asp Ser Thr Ile Leu Ser Gly Gly Thr
            20                  25                  30

Ala Asp His Ile Ser Gly Asp Val Cys Phe Asn Leu Pro Gln Asp Trp
        35                  40                  45

Ser Met Arg Gly Ser Glu Ile Ser Gly Ile Ile Gly Glu Pro Lys Ile
    50                  55                  60

Glu Asp Phe Ile Gly Gly Leu Ser Phe Ser Glu Gln His His Lys Gly
65                  70                  75                  80

Asn Cys Asn Met Leu Pro Ser Thr Ser Thr Ile Cys Tyr Gly Ser
                85                  90                  95

Ser Gly Gly Ser Thr Gly Tyr His His Gln Ile Tyr His Gln Pro Thr
            100                 105                 110

```
Ser Ser Gly Ile His Phe Gly Asp Ser Ile Met Ile Gly Ser Ser Gly
        115                 120                 125

Gly Ile His Asp Gly Gly Met Ile Ser Gly Gly Gly Asn Gly
    130                 135                 140

Ile Gly Gly Gly Gly Ser Gly Asn Gly Gly Ile Gly Leu Ser Met
145                 150                 155                 160

Ile Lys Asn Trp Leu Arg Ser Gln Pro Gly Pro Met Gln Pro Arg Ile
                165                 170                 175

Gly Gly Gly Glu Gly Gly Gln Gly Ile Ser Ile Ser Met Asn Met Gly
                180                 185                 190

Gly Thr Thr Gln Gly Gly Gly Met Pro Ile Val Gly Gly Glu Arg
            195                 200                 205

Gly Arg Gly Pro Glu Ser Ile Ser Thr Ser Gly Gln Gly Gly Ile
            210                 215                 220

Ile Ile Thr Gly Pro Lys Glu Asp Ser Gly Gly Ser Gly Leu Gly Gly
225                 230                 235                 240

Gly Val Leu Gly Leu Ser Thr Asp Thr Gly Ser Gly Gly Gly Ser
                245                 250                 255

Gly Asp Asn Thr Gly Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
            275                 280                 285

Ala His Leu Trp Asp Asn Ser Cys Arg Arg Glu Gly Gln Thr Arg Lys
        290                 295                 300

Gly Arg Gln Val Tyr Leu Gly Gly Tyr Asp Lys Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Ala Ala Glu Ala
                405                 410                 415

Tyr Asp Ile Ala Ala Ile Lys Phe Arg Gly Leu Asn Ala Val Thr Asn
                420                 425                 430

Phe Asp Met Ser Arg Tyr Asp Val Lys Ser Ile Leu Asp Ser Ser Ala
            435                 440                 445

Leu Pro Ile Gly Ser Ala Ala Lys Arg Leu Lys Glu Ala Glu Ala Gly
    450                 455                 460

Gly Ser Gly Gln His His His Gly Gly Leu Leu Ser Tyr Asp Leu Gly
465                 470                 475                 480

Arg Val Gly Ser Gln Val Gly Asp Gly Gly Val Gly Gly Gly Tyr
                485                 490                 495

Gly Gly His Tyr His Gly Gly Trp Pro Thr Val Gly Phe Gln Pro
            500                 505                 510

Gly Gly Gly Ser Thr Gly Val Tyr His Pro Tyr Gly Gln Gln Pro Met
        515                 520                 525

Arg Gly Gly Gly Trp Cys Lys Gln Glu Gln Asp His Gly Leu Val Gly
```

```
                530           535            540
Gly Gly His Ser Val Gln Asp Val His Val Asn Val Gly Gly Gly
545                 550            555                 560

Gly Gly His Asp Phe Phe Ser Gly Gln Gln Gly Gly Gly Ala
            565             570             575

Met His Gly Val Gly Ser Val Asp Ser Ala Ser Val Glu His Ser Thr
                580             585             590

Gly Ser Asn Ser Val Val Tyr Asn Gly Gly Leu Gly Asp Ser Asn Gly
                595             600             605

Ala Ser Ala Leu Gly Gly Ser Gly Gly Gly Tyr Met Met Pro Met Ser
610                 615             620

Ala Ala Gly Ala Thr Thr Thr Ser Ala Met Leu Ser His Glu Gln Leu
625                 630             635             640

His Ala Arg Ala Tyr Asp Glu Ala Lys Gln Ala Ala Gln Met Gly Tyr
                645             650             655

Glu Ser Tyr Leu Val Asn Ala Glu Asn Asn Gly Gly Gly Arg Met Ser
                660             665             670

Ala Trp Gly Thr Leu Leu Ser Ala Ala Ala Ala Ala Ala Ser Ser
                675             680             685

Asn Asp Asn Met Ala Ala Asp Val Gly His Gly Gly Ala Gln Leu Phe
690                 695             700

Ser Val Trp Asn Asp Thr
705                 710

<210> SEQ ID NO 24
<211> LENGTH: 710
<212> TYPE: PRT
<213> ORGANISM: Artificial sequence
<220> FEATURE:
<223> OTHER INFORMATION: Consensus sequence of Figure 2.
<220> FEATURE:
<221> NAME/KEY: MISC_FEATURE
<222> LOCATION: (0)..(0)
<223> OTHER INFORMATION: Synthesized

<400> SEQUENCE: 24

Met Ala Thr Ile Asn Asn Trp Leu Ala Phe Ser Leu Ser Pro Gln Glu
1               5                   10                  15

Ile Pro Pro Ser Gln Thr Thr Asp Ser Thr Ile Leu Ser Ala Ala Thr
                20                  25                  30

Ala Asp His Ile Ser Gly Asp Val Cys Phe Asn Leu Pro Gln Asp Trp
            35                  40                  45

Ser Met Arg Gly Ser Glu Ile Ser Ala Ile Ile Ala Glu Pro Lys Ile
50                  55                  60

Glu Asp Phe Ile Gly Gly Leu Ser Phe Ser Gln His His Lys Ala
65                  70                  75                  80

Asn Cys Asn Met Leu Pro Ser Thr Ser Ser Thr Ile Cys Tyr Ala Ser
                85                  90                  95

Ser Gly Ala Ser Thr Gly Tyr His His Gln Ile Tyr His Gln Pro Thr
                100                 105                 110

Ser Ser Ala Ile His Phe Ala Asp Ser Ile Met Ile Ala Ser Ser Ala
            115                 120                 125

Gly Ile His Asp Gly Gly Ala Met Ile Ser Ala Ala Ala Asn Gly
            130                 135                 140

Ile Ala Gly Ala Ala Ser Ala Asn Gly Gly Gly Ile Gly Leu Ser Met
145                 150                 155                 160
```

-continued

```
Ile Lys Asn Trp Leu Arg Ser Gln Pro Ala Pro Met Gln Pro Arg Ile
            165                 170                 175
Ala Ala Ala Glu Gly Ala Gln Gly Ile Ser Ile Ser Met Asn Met Ala
        180                 185                 190
Gly Thr Thr Gln Gly Ala Ala Gly Met Pro Ile Val Ala Gly Glu Arg
        195                 200                 205
Ala Arg Ala Pro Glu Ser Ile Ser Thr Ser Ala Gln Gly Gly Ala Ile
        210                 215                 220
Ile Ile Thr Ala Pro Lys Glu Asp Ser Gly Ser Gly Leu Ala Gly
225                 230                 235                 240
Ala Val Leu Ala Leu Ser Thr Asp Thr Gly Ser Gly Gly Ala Ser
            245                 250                 255
Ala Asp Asn Thr Ala Arg Lys Thr Val Asp Thr Phe Gly Gln Arg Thr
        260                 265                 270
Ser Ile Tyr Arg Gly Val Thr Arg His Arg Trp Thr Gly Arg Tyr Glu
        275                 280                 285
Ala His Leu Trp Asp Asn Ser Cys Arg Arg Glu Gly Gln Thr Arg Lys
        290                 295                 300
Gly Arg Gln Val Tyr Leu Gly Gly Tyr Asp Lys Glu Glu Lys Ala Ala
305                 310                 315                 320
Arg Ala Tyr Asp Leu Ala Ala Leu Lys Tyr Trp Gly Ala Thr Thr Thr
                325                 330                 335
Thr Asn Phe Pro Val Ser Asn Tyr Glu Lys Glu Leu Glu Asp Met Lys
            340                 345                 350
His Met Thr Arg Gln Glu Phe Val Ala Ser Leu Arg Arg Lys Ser Ser
        355                 360                 365
Gly Phe Ser Arg Gly Ala Ser Ile Tyr Arg Gly Val Thr Arg His His
        370                 375                 380
Gln His Gly Arg Trp Gln Ala Arg Ile Gly Arg Val Ala Gly Asn Lys
385                 390                 395                 400
Asp Leu Tyr Leu Gly Thr Phe Ser Thr Gln Glu Glu Ala Ala Glu Ala
                405                 410                 415
Tyr Asp Ile Ala Ala Ile Lys Phe Arg Gly Leu Asn Ala Val Thr Asn
        420                 425                 430
Phe Asp Met Ser Arg Tyr Asp Val Lys Ser Ile Leu Asp Ser Ser Ala
        435                 440                 445
Leu Pro Ile Gly Ser Ala Ala Lys Arg Leu Lys Glu Ala Glu Ala Ala
        450                 455                 460
Ala Ser Ala Gln His His His Ala Gly Leu Leu Ser Tyr Asp Leu Gly
465                 470                 475                 480
Arg Val Ala Ser Gln Val Gly Asp Gly Gly Ala Val Ala Ala Ala Tyr
                485                 490                 495
Gly Ala His Tyr His Gly Ala Ala Trp Pro Thr Val Ala Phe Gln Pro
            500                 505                 510
Gly Ala Ala Ser Thr Gly Val Tyr His Pro Tyr Ala Gln Gln Pro Met
        515                 520                 525
Arg Gly Gly Gly Trp Cys Lys Gln Glu Gln Asp His Ala Leu Val Ala
    530                 535                 540
Ala Ala His Ser Val Gln Asp Val His Val Asn Val Gly Ala Ala
545                 550                 555                 560
Gly Ala His Asp Phe Phe Ser Ala Gly Gln Gln Ala Ala Ala Ala
                565                 570                 575
Met His Gly Val Gly Ser Val Asp Ser Ala Ser Val Glu His Ser Thr
```

```
                580             585             590
Gly Ser Asn Ser Val Val Tyr Asn Gly Gly Leu Gly Asp Ser Asn Gly
                    595                 600                 605

Ala Ser Ala Leu Gly Ser Gly Gly Gly Tyr Met Met Pro Met Ser
    610                 615                 620

Ala Ala Gly Ala Thr Thr Ser Ala Met Leu Ser His Glu Gln Val
625                 630                 635                 640

His Ala Arg Ala Tyr Asp Glu Ala Lys Gln Ala Gln Met Gly Tyr
                645                 650                 655

Glu Ser Tyr Leu Val Asn Ala Glu Asn Asn Gly Gly Gly Arg Met Ser
                    660                 665                 670

Ala Trp Gly Thr Val Val Ser Ala Ala Ala Ala Ala Ala Ser Ser
                675                 680                 685

Asn Asp Asn Met Ala Ala Asp Val Gly His Gly Gly Ala Gln Leu Phe
        690                 695                 700

Ser Val Trp Asn Asp Thr
705                 710
```

<210> SEQ ID NO 25
<211> LENGTH: 2079
<212> TYPE: DNA
<213> ORGANISM: Oryza sativa
<220> FEATURE:
<221> NAME/KEY: misc_feature
<222> LOCATION: (0)..(0)
<223> OTHER INFORMATION: predicted cDNA of OsANT, Genbank Accession
      No.AP003313 (rice ODP2)
<220> FEATURE:
<221> NAME/KEY: misc_feature
<222> LOCATION: (1)..(2079)
<223> OTHER INFORMATION: CDS

<400> SEQUENCE: 25
atggccacca tgaacaactg gctggccttc tccctctccc cgcaggatca gctcccgccg      60
tctcagacca actccactct catctccgcc gccgccacca ccaccaccgc cggcgactcc     120
tccaccggcg acgtctgctt caacatcccc aagattgga gcatgagggg atcggagctc      180
tcggcgctcg tcgccgagcc gaagctggag gacttcctcg gcggcatctc cttctcggag     240
cagcagcatc atcacggcgg caagggcggc gtgatcccga gcagcgccgc cgcttgctac     300
gcgagctccg cagcagcgt cggctacctg taccctcctc caagctcatc ctcgctccag      360
ttcgccgact ccgtcatggt ggccacctcc tcgcccgtcg tcgcccacga cggcgtcagc     420
ggcggcggca tggtgagcgc cgccgccgcc gggcggcca gtggcaacgg cggcattggc      480
ctgtccatga tcaagaactg gctccggagc cagccggcgc cgcagccggc gcaggcgctg     540
tctctgtcca tgaacatggc ggggacgacg acggcgcagg gcggcggcgc catggcgctc     600
ctcgccggcg caggggagcg aggccggacg acgcccgcgt cagagagcct gtccacgtcg     660
gcgcacggag cgacgacggc gacgatggct ggtggtcgca aggagattaa cgaggaaggc     720
agcggcagcg ccggcgccgt ggttgccgtc ggctcggagt caggcggcag cggcgccgtg     780
gtggaggccg gcgcggcggc ggcggcggcg aggaagtccg tcgacacgtt cggccagaga     840
acatcgatct accgcggcgt gacaaggcat agatggacag ggaggtatga ggctcatctt     900
tgggacaaca gctgcagaag agagggccaa actcgcaagg tcgtcaagg tggttatgac      960 aaagaggaaa aagctgctag agcttatgat ttggctgctc tcaaatactg gggcccgacg    1020
acgacgacaa atttttccggt aaataactat gaaaaggagc tggaggagat gaagcacatg    1080

-continued

```
acaaggcagg agttcgtagc ctctttgaga aggaagagca gtggtttctc cagaggtgca    1140
tccatttacc gtggagtaac taggcatcac cagcatggga gatggcaagc aaggatagga    1200
agagttgcag ggaacaagga cctctacttg ggcaccttca gcacgcagga ggaggcggcg    1260
gaggcgtacg acatcgcggc gatcaagttc cgggggctca acgccgtcac caacttcgac    1320
atgagccgct acgacgtcaa gagcatcctc gacagcgctg ccctcccgt cggcaccgcc     1380 gccaagcgcc tcaaggacgc cgaggccgcc gccgcctacg acgtcggccg catcgcctcg    1440
cacctcggcg gcgacggcgc ctacgccgcg cattacggcc accaccacca ctcggccgcc    1500
gccgcctggc cgaccatcgc gttccaggcg gcggcggcgc cgccgccgca cgccgccggg    1560
ctttaccacc cgtacgcgca gccgctgcgt gggtggtgca agcaggagca ggaccacgcc    1620
gtgatcgcgg cggcgcacag cctgcaggat ctccaccacc tcaacctcgg cgccgccgcc    1680
gccgcgcatg acttcttctc gcaggcgatg cagcagcagc acggcctcgg cagcatcgac    1740
aacgcgtcgc tcgagcacag caccggctcc aactccgtcg tctacaacgg cgacaatggc    1800
ggcggaggcg gcggctacat catggcgccg atgagcgccg tgtcggccac ggccaccgcg    1860
gtggcgagca gccacgatca cggcggcgac ggcgggaagc aggtgcagat ggggtacgac    1920
agctacctcg tcggcgcaga cgcctacggc ggcggcggcg ccgggaggat gccatcctgg    1980
gcgatgacgc cggcgtcggc gccggccgcc acgagcagca gcgacatgac cggagtctgc    2040
catggcgcac agctcttcag cgtctggaac gacacataa                          2079
```

<210> SEQ ID NO 26
<211> LENGTH: 692
<212> TYPE: PRT
<213> ORGANISM: Oryza sativa

<400> SEQUENCE: 26

```
Met Ala Thr Met Asn Asn Trp Leu Ala Phe Ser Leu Ser Pro Gln Asp
1               5                   10                  15

Gln Leu Pro Pro Ser Gln Thr Asn Ser Thr Leu Ile Ser Ala Ala Ala
            20                  25                  30

Thr Thr Thr Thr Ala Gly Asp Ser Ser Thr Gly Asp Val Cys Phe Asn
        35                  40                  45

Ile Pro Gln Asp Trp Ser Met Arg Gly Ser Glu Leu Ser Ala Leu Val
    50                  55                  60

Ala Glu Pro Lys Leu Glu Asp Phe Leu Gly Gly Ile Ser Phe Ser Glu
65                  70                  75                  80

Gln Gln His His His Gly Gly Lys Gly Gly Val Ile Pro Ser Ser Ala
                85                  90                  95

Ala Ala Cys Tyr Ala Ser Ser Gly Ser Ser Val Gly Tyr Leu Tyr Pro
            100                 105                 110

Pro Pro Ser Ser Ser Ser Leu Gln Phe Ala Asp Ser Val Met Val Ala
        115                 120                 125

Thr Ser Ser Pro Val Val Ala His Asp Gly Val Ser Gly Gly Gly Met
    130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                165                 170                 175

Ala Gln Ala Leu Ser Leu Ser Met Asn Met Gly Thr Thr Thr Ala
            180                 185                 190

Gln Gly Gly Gly Ala Met Ala Leu Leu Ala Gly Ala Gly Glu Arg Gly
```

```
            195                 200                 205
Arg Thr Thr Pro Ala Ser Glu Ser Leu Ser Thr Ser Ala His Gly Ala
210                 215                 220

Thr Thr Ala Thr Met Ala Gly Gly Arg Lys Glu Ile Asn Glu Glu Gly
225                 230                 235                 240

Ser Gly Ser Ala Gly Ala Val Val Ala Val Gly Ser Glu Ser Gly Gly
                245                 250                 255

Ser Gly Ala Val Val Glu Ala Gly Ala Ala Ala Ala Ala Ala Arg Lys
            260                 265                 270

Ser Val Asp Thr Phe Gly Gln Arg Thr Ser Ile Tyr Arg Gly Val Thr
            275                 280                 285

Arg His Arg Trp Thr Gly Arg Tyr Glu Ala His Leu Trp Asp Asn Ser
            290                 295                 300

Cys Arg Arg Glu Gly Gln Thr Arg Lys Gly Arg Gln Gly Gly Tyr Asp
305                 310                 315                 320

Lys Glu Glu Lys Ala Ala Arg Ala Tyr Asp Leu Ala Ala Leu Lys Tyr
                325                 330                 335

Trp Gly Pro Thr Thr Thr Thr Asn Phe Pro Val Asn Asn Tyr Glu Lys
            340                 345                 350

Glu Leu Glu Glu Met Lys His Met Thr Arg Gln Glu Phe Val Ala Ser
            355                 360                 365

Leu Arg Arg Lys Ser Ser Gly Phe Ser Arg Gly Ala Ser Ile Tyr Arg
370                 375                 380

Gly Val Thr Arg His His Gln His Gly Arg Trp Gln Ala Arg Ile Gly
385                 390                 395                 400

Arg Val Ala Gly Asn Lys Asp Leu Tyr Leu Gly Thr Phe Ser Thr Gln
                405                 410                 415

Glu Glu Ala Ala Glu Ala Tyr Asp Ile Ala Ala Ile Lys Phe Arg Gly
            420                 425                 430

Leu Asn Ala Val Thr Asn Phe Asp Met Ser Arg Tyr Asp Val Lys Ser
            435                 440                 445

Ile Leu Asp Ser Ala Ala Leu Pro Val Gly Thr Ala Ala Lys Arg Leu
450                 455                 460

Lys Asp Ala Glu Ala Ala Ala Tyr Asp Val Gly Arg Ile Ala Ser
465                 470                 475                 480

His Leu Gly Gly Asp Gly Ala Tyr Ala Ala His Tyr Gly His His His
                485                 490                 495

His Ser Ala Ala Ala Ala Trp Pro Thr Ile Ala Phe Gln Ala Ala Ala
            500                 505                 510

Ala Pro Pro Pro His Ala Ala Gly Leu Tyr His Pro Tyr Ala Gln Pro
            515                 520                 525

Leu Arg Gly Trp Cys Lys Gln Glu Gln Asp His Ala Val Ile Ala Ala
            530                 535                 540

Ala His Ser Leu Gln Asp Leu His His Leu Asn Leu Gly Ala Ala Ala
545                 550                 555                 560

Ala Ala His Asp Phe Phe Ser Gln Ala Met Gln Gln Gln His Gly Leu
                565                 570                 575

Gly Ser Ile Asp Asn Ala Ser Leu Glu His Ser Thr Gly Ser Asn Ser
            580                 585                 590

Val Val Tyr Asn Gly Asp Asn Gly Gly Gly Gly Gly Tyr Ile Met
            595                 600                 605

Ala Pro Met Ser Ala Val Ser Ala Thr Ala Thr Ala Val Ala Ser Ser
610                 615                 620
```

His Asp His Gly Gly Asp Gly Gly Lys Gln Val Gln Met Gly Tyr Asp
625                 630                 635                 640

Ser Tyr Leu Val Gly Ala Asp Ala Tyr Gly Gly Gly Ala Gly Arg
            645                 650                 655

Met Pro Ser Trp Ala Met Thr Pro Ala Ser Ala Pro Ala Ala Thr Ser
        660                 665                 670

Ser Ser Asp Met Thr Gly Val Cys His Gly Ala Gln Leu Phe Ser Val
    675                 680                 685

Trp Asn Asp Thr
    690

<210> SEQ ID NO 27
<211> LENGTH: 1794
<212> TYPE: DNA
<213> ORGANISM: Oryza sativa
<220> FEATURE:
<221> NAME/KEY: misc_feature
<222> LOCATION: (0)..(0)
<223> OTHER INFORMATION: predicted OsBNM, Genbank Accession No. AY062180
      (rice ODP2)
<220> FEATURE:
<221> NAME/KEY: misc_feature
<222> LOCATION: (0)..(1794)
<223> OTHER INFORMATION: CDS

<400> SEQUENCE: 27
atggccacca tgaacaactg gctggccttc tccctctccc cgcaggatca gctcccgccg      60
tctcagacca actccacttt catctccgcc gccgccacca ccaccaccgc cggcgactcc     120
tccaccggcg acgtctgctt caacatcccc aagctcacc cctccacgcc ggccattggc      180
aacggcggca ttggcctgtc catgatcaag aactggctcc ggagccagcc ggcgccgcag     240
ccggcgcagg cgctgtctct gtccatgaac atggcgggga cgacgacggc gcagggcggc     300
ggcgccatgg cgctcctcgc cggcgcaggg gagcgaggcc ggacgacgcc cgcgtcagag     360
agcctgtcca cgtcggcgca cggagcgacg acggcgacga tggctggtgg tcgcaaggag     420
attaacgagg aaggcagcgg cagcgccggc gccgtggttg ccgtcggctc ggagtcaggc     480
ggcagcggcg ccgtggtgga ggccggcgcg gcggcggcgg cggcgaggaa gtccgtcgac     540
acgttcggcc agagaacatc gatctaccgc ggcgtgacaa ggcatagatg gacagggagg     600
tatgaggctc atctttggga caacagctgc agaagagagg gccaaactcg caagggtcgt     660
caaggtggtt atgacaaaga ggaaaaagct gctagagctt atgatttggc tgctctcaaa     720
tactggggcc cgacgacgac gacaaatttt ccggtaaata actatgaaaa ggagctggag     780
gagatgaagc acatgacaag gcaggagttc gtagcctctt tgagaaggaa gagcagtggt     840
ttctccagag gtgcatccat ttaccgtgga gtaactaggc atcaccagca tgggagatgg     900
caagcaagga taggaagagt tgcagggaac aaggacctct acttgggcac cttcagcacg     960
caggaggagg cggcgaggc gtacgacatc gcggcgatca gttccgggg gctcaacgcc     1020 gtcaccaact tcgacatgag ccgctacgac gtcaagagca tcctcgacag cgctgccctc     1080
cccgtcggca ccgccgccaa gcgcctcaag gacgccgagg ccgccgccgc ctacgacgtc     1140
ggccgcatcg cctcgcacct cggcggcgac ggcgcctacg ccgcgcatta cggccaccac     1200
caccactcgg ccgccgccgc ctggccgacc atcgcgttcc aggcggcggc ggcgccgccg     1260
ccgcacgccg ccgggcttta ccacccgtac gcgcagccgc tgcgtggggtg gtgcaagcag     1320 gagcaggacc acgccgtgat cgcggcggcg cacagcctgc aggatctcca ccacctcaac     1380

-continued

```
ctcggcgccg ccgccgccgc gcatgacttc ttctcgcagg cgatgcagca gcagcacggc    1440
ctcggcagca tcgacaacgc gtcgctcgag cacagcaccg gctccaactc cgtcgtctac    1500
aacggcgaca atggcggcgg aggcggcggc tacatcatgg cgccgatgag cgccgtgtcg    1560
gccacggcca ccgcggtggc gagcagccac gatcacggcg cgacggcgg gaagcaggtg     1620 cagatggggt acgacagcta cctcgtcggc gcagacgcct acggcggcgg cggcgccggg    1680
aggatgccat cctgggcgat gacgccggcg tcggcgccgg ccgccacgag cagcagcgac    1740
atgaccggag tctgccatgg cgcacagctc ttcagcgtct ggaacgacac ataa          1794
```

<210> SEQ ID NO 28
<211> LENGTH: 597
<212> TYPE: PRT
<213> ORGANISM: Oryza sativa

<400> SEQUENCE: 28

```
Met Ala Thr Met Asn Asn Trp Leu Ala Phe Ser Leu Ser Pro Gln Asp
 1               5                  10                  15

Gln Leu Pro Pro Ser Gln Thr Asn Ser Thr Phe Ile Ser Ala Ala Ala
                20                  25                  30

Thr Thr Thr Thr Ala Gly Asp Ser Ser Thr Gly Asp Val Cys Phe Asn
            35                  40                  45

Ile Pro Gln Ala His Pro Ser Thr Pro Ala Ile Gly Asn Gly Gly Ile
        50                  55                  60

Gly Leu Ser Met Ile Lys Asn Trp Leu Arg Ser Gln Pro Ala Pro Gln
 65                 70                  75                  80

Pro Ala Gln Ala Leu Ser Leu Ser Met Asn Met Ala Gly Thr Thr Thr
                85                  90                  95

Ala Gln Gly Gly Gly Ala Met Ala Leu Leu Ala Gly Ala Gly Glu Arg
           100                 105                 110

Gly Arg Thr Thr Pro Ala Ser Glu Ser Leu Ser Thr Ser Ala His Gly
        115                 120                 125

Ala Thr Thr Ala Thr Met Ala Gly Gly Arg Lys Glu Ile Asn Glu Glu
    130                 135                 140

Gly Ser Gly Ser Ala Gly Ala Val Val Ala Val Gly Ser Glu Ser Gly
145                 150                 155                 160

Gly Ser Gly Ala Val Val Glu Ala Gly Ala Ala Ala Ala Arg
                165                 170                 175

Lys Ser Val Asp Thr Phe Gly Gln Arg Thr Ser Ile Tyr Arg Gly Val
                180                 185                 190

Thr Arg His Arg Trp Thr Gly Arg Tyr Glu Ala His Leu Trp Asp Asn
            195                 200                 205

Ser Cys Arg Arg Glu Gly Gln Thr Arg Lys Gly Arg Gln Gly Gly Tyr
        210                 215                 220

Asp Lys Glu Glu Lys Ala Ala Arg Ala Tyr Asp Leu Ala Ala Leu Lys
225                 230                 235                 240

Tyr Trp Gly Pro Thr Thr Thr Thr Asn Phe Pro Val Asn Asn Tyr Glu
                245                 250                 255

Lys Glu Leu Glu Glu Met Lys His Met Thr Arg Gln Glu Phe Val Ala
            260                 265                 270

Ser Leu Arg Arg Lys Ser Ser Gly Phe Ser Arg Gly Ala Ser Ile Tyr
        275                 280                 285

Arg Gly Val Thr Arg His His Gln His Gly Arg Trp Gln Ala Arg Ile
    290                 295                 300
```

-continued

```
Gly Arg Val Ala Gly Asn Lys Asp Leu Tyr Leu Gly Thr Phe Ser Thr
305                 310                 315                 320

Gln Glu Glu Ala Glu Ala Tyr Asp Ile Ala Ala Ile Lys Phe Arg
            325                 330                 335

Gly Leu Asn Ala Val Thr Asn Phe Asp Met Ser Arg Tyr Asp Val Lys
            340                 345                 350

Ser Ile Leu Asp Ser Ala Ala Leu Pro Val Gly Thr Ala Ala Lys Arg
        355                 360                 365

Leu Lys Asp Ala Glu Ala Ala Ala Tyr Asp Val Gly Arg Ile Ala
    370                 375                 380

Ser His Leu Gly Gly Asp Gly Ala Tyr Ala His Tyr Gly His His
385                 390                 395                 400

His His Ser Ala Ala Ala Trp Pro Thr Ile Ala Phe Gln Ala Ala
            405                 410                 415

Ala Ala Pro Pro Pro His Ala Ala Gly Leu Tyr His Pro Tyr Ala Gln
            420                 425                 430

Pro Leu Arg Gly Trp Cys Lys Gln Glu Gln Asp His Ala Val Ile Ala
    435                 440                 445

Ala Ala His Ser Leu Gln Asp Leu His His Leu Asn Leu Gly Ala Ala
450                 455                 460

Ala Ala Ala His Asp Phe Phe Ser Gln Ala Met Gln Gln Gln His Gly
465                 470                 475                 480

Leu Gly Ser Ile Asp Asn Ala Ser Leu Glu His Ser Thr Gly Ser Asn
            485                 490                 495

Ser Val Val Tyr Asn Gly Asp Asn Gly Gly Gly Gly Gly Tyr Ile
            500                 505                 510

Met Ala Pro Met Ser Ala Val Ser Ala Thr Ala Thr Ala Val Ala Ser
            515                 520                 525

Ser His Asp His Gly Gly Asp Gly Gly Lys Gln Val Gln Met Gly Tyr
    530                 535                 540

Asp Ser Tyr Leu Val Gly Ala Asp Ala Tyr Gly Gly Gly Ala Gly
545                 550                 555                 560

Arg Met Pro Ser Trp Ala Met Thr Pro Ala Ser Ala Pro Ala Ala Thr
            565                 570                 575

Ser Ser Ser Asp Met Thr Gly Val Cys His Gly Ala Gln Leu Phe Ser
        580                 585                 590

Val Trp Asn Asp Thr
        595

<210> SEQ ID NO 29
<211> LENGTH: 655
<212> TYPE: PRT
<213> ORGANISM: Oryza sativa

<400> SEQUENCE: 29

Met Ala Ser Ala Asp Asn Trp Leu Gly Phe Ser Leu Ser Gly Gln Gly
1               5                   10                  15

Asn Pro Gln His His Gln Asn Gly Ser Pro Ser Ala Ala Gly Asp Ala
            20                  25                  30

Ala Ile Asp Ile Ser Gly Ser Gly Asp Phe Tyr Gly Leu Pro Thr Pro
        35                  40                  45

Asp Ala His His Ile Gly Met Ala Gly Glu Asp Ala Pro Tyr Gly Val
    50                  55                  60

Met Asp Ala Phe Asn Arg Gly Thr His Glu Thr Gln Asp Trp Ala Met
65                  70                  75                  80
```

-continued

```
Arg Gly Leu Asp Tyr Gly Gly Ser Ser Asp Leu Ser Met Leu Val
                85                  90                  95
Gly Ser Ser Gly Gly Arg Arg Thr Val Ala Gly Asp Gly Val Gly
            100                 105                 110
Glu Ala Pro Lys Leu Glu Asn Phe Leu Asp Gly Asn Ser Phe Ser Asp
            115                 120                 125
Val His Gly Gln Ala Ala Gly Gly Tyr Leu Tyr Ser Gly Ser Ala Val
        130                 135                 140
Gly Gly Ala Gly Gly Tyr Ser Asn Gly Gly Cys Gly Gly Thr Ile
145                 150                 155                 160
Glu Leu Ser Met Ile Lys Thr Trp Leu Arg Ser Asn Gln Ser Gln Gln
                165                 170                 175
Gln Pro Ser Pro Pro Gln His Ala Asp Gln Gly Met Ser Thr Asp Ala
            180                 185                 190
Ser Ala Ser Ser Tyr Ala Cys Ser Asp Val Leu Val Gly Ser Cys Gly
            195                 200                 205
Gly Gly Gly Ala Gly Gly Thr Ala Ser Ser His Gly Gln Gly Leu Ala
210                 215                 220
Leu Ser Met Ser Thr Gly Ser Val Ala Ala Gly Gly Gly Ala
225                 230                 235                 240
Val Val Ala Ala Glu Ser Ser Ser Glu Asn Lys Arg Val Asp Ser
            245                 250                 255
Pro Gly Gly Ala Val Asp Gly Ala Val Pro Arg Lys Ser Ile Asp Thr
            260                 265                 270
Phe Gly Gln Arg Thr Ser Ile Tyr Arg Gly Val Thr Arg His Arg Trp
            275                 280                 285
Thr Gly Arg Tyr Glu Ala His Leu Trp Asp Asn Ser Cys Arg Arg Glu
        290                 295                 300
Gly Gln Ser Arg Lys Gly Arg Gln Gly Gly Tyr Asp Lys Glu Asp Lys
305                 310                 315                 320
Ala Ala Arg Ala Tyr Asp Leu Ala Ala Leu Lys Tyr Trp Gly Thr Thr
                325                 330                 335
Thr Thr Thr Asn Phe Pro Met Ser Asn Tyr Glu Lys Glu Leu Glu Glu
            340                 345                 350
Met Lys His Met Thr Arg Gln Glu Tyr Ile Ala His Leu Arg Arg Asn
            355                 360                 365
Ser Ser Gly Phe Ser Arg Gly Ala Ser Lys Tyr Arg Gly Val Thr Arg
        370                 375                 380
His His Gln His Gly Arg Trp Gln Ala Arg Ile Gly Arg Val Ala Gly
385                 390                 395                 400
Asn Lys Asp Ile Tyr Leu Gly Thr Phe Ser Thr Glu Glu Ala Ala
                405                 410                 415
Glu Ala Tyr Asp Ile Ala Ala Ile Lys Phe Arg Gly Leu Asn Ala Val
            420                 425                 430
Thr Asn Phe Asp Met Ser Arg Tyr Asp Val Lys Ser Ile Leu Asp Ser
            435                 440                 445
Ser Thr Leu Pro Val Gly Gly Ala Ala Arg Arg Leu Lys Glu Ala Glu
450                 455                 460
Val Ala Ala Ala Ala Gly Gly Val Ile Val Ser His Leu Ala
465                 470                 475                 480
Asp Gly Gly Val Gly Tyr Tyr Tyr Gly Cys Gly Pro Thr Ile Ala
                485                 490                 495
```

```
Phe Gly Gly Gly Gly Gln Gln Pro Ala Pro Leu Ala Val His Tyr Pro
                500                 505                 510

Ser Tyr Gly Gln Ala Ser Gly Trp Cys Lys Pro Glu Gln Asp Ala Val
        515                 520                 525

Ile Ala Ala Gly His Cys Ala Thr Asp Leu Gln His Leu His Leu Gly
    530                 535                 540

Ser Gly Gly Ala Ala Ala Thr His Asn Phe Phe Gln Gln Pro Ala Ser
545                 550                 555                 560

Ser Ser Ala Val Tyr Gly Asn Gly Gly Gly Gly Gly Asn Ala Phe
                565                 570                 575

Met Met Pro Met Gly Ala Val Val Ala Ala Asp His Gly Gly Gln
        580                 585                 590

Ser Ser Ala Tyr Gly Gly Gly Asp Glu Ser Gly Arg Leu Val Val Gly
        595                 600                 605

Tyr Asp Gly Val Val Asp Pro Tyr Ala Ala Met Arg Ser Ala Tyr Glu
    610                 615                 620

Leu Ser Gln Gly Ser Ser Ser Ser Val Ser Val Ala Lys Ala Ala
625                 630                 635                 640

Asn Gly Tyr Pro Asp Asn Trp Ser Ser Pro Phe Asn Gly Met Gly
                645                 650                 655

<210> SEQ ID NO 30
<211> LENGTH: 581
<212> TYPE: PRT
<213> ORGANISM: Arabidopsis thaliana

<400> SEQUENCE: 30

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
                20                  25                  30

Val Asp Val Ala Gly Gly Tyr Cys Phe Asp Leu Ala Ala Pro Ser Asp
            35                  40                  45

Glu Ser Ser Ala Val Gln Thr Ser Phe Leu Ser Pro Phe Gly Val Thr
        50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Asn Glu Gln Asn Gly
                85                  90                  95

Pro Lys Leu Glu Asn Phe Leu Gly Arg Thr Thr Thr Ile Tyr Asn Thr
                100                 105                 110

Asn Glu Thr Val Val Asp Gly Asn Gly Asp Cys Gly Gly Gly Asp Gly
            115                 120                 125

Gly Gly Gly Gly Ser Leu Gly Leu Ser Met Ile Lys Thr Trp Leu Ser
        130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Thr Ser Asp Ser Asn Asn
                165                 170                 175

Tyr Asn Asn Asn Asp Asp Val Val Gln Glu Lys Thr Ile Val Asp Val
                180                 185                 190

Val Glu Thr Thr Pro Lys Lys Thr Ile Glu Ser Phe Gly Gln Arg Thr
            195                 200                 205

Ser Ile Tyr Arg Gly Val Thr Arg His Arg Trp Thr Gly Arg Tyr Glu
        210                 215                 220
```

Ala His Leu Trp Asp Asn Ser Cys Lys Arg Glu Gly Gln Thr Arg Lys
225                 230                 235                 240

Gly Arg Gln Gly Gly Tyr Asp Lys Glu Glu Lys Ala Ala Arg Ala Tyr
            245                 250                 255

Asp Leu Ala Ala Leu Lys Tyr Trp Gly Thr Thr Thr Thr Thr Asn Phe
        260                 265                 270

Pro Leu Ser Glu Tyr Glu Lys Glu Val Glu Glu Met Lys His Met Thr
    275                 280                 285

Arg Gln Glu Tyr Val Ala Ser Leu Arg Arg Lys Ser Ser Gly Phe Ser
290                 295                 300

Arg Gly Ala Ser Ile Tyr Arg Gly Val Thr Arg His His Gln His Gly
305                 310                 315                 320

Arg Trp Gln Ala Arg Ile Gly Arg Val Ala Gly Asn Lys Asp Leu Tyr
                325                 330                 335

Leu Gly Thr Phe Gly Thr Gln Glu Glu Ala Ala Glu Ala Tyr Asp Ile
            340                 345                 350

Ala Ala Ile Lys Phe Arg Gly Leu Ser Ala Val Thr Asn Phe Asp Met
        355                 360                 365

Asn Arg Tyr Asn Val Lys Ala Ile Leu Glu Ser Pro Ser Leu Pro Ile
    370                 375                 380

Gly Ser Ser Ala Lys Arg Leu Lys Asp Val Asn Asn Pro Val Pro Ala
385                 390                 395                 400

Met Met Ile Ser Asn Asn Val Ser Glu Ser Ala Asn Asn Val Ser Gly
                405                 410                 415

Trp Gln Asn Thr Ala Phe Gln His His Gln Gly Met Asp Leu Ser Leu
            420                 425                 430

Leu Gln Gln Gln Gln Glu Arg Tyr Val Gly Tyr Tyr Asn Gly Gly Asn
        435                 440                 445

Leu Ser Thr Glu Ser Thr Arg Val Cys Phe Lys Gln Glu Glu Glu Gln
    450                 455                 460

Gln His Phe Leu Arg Asn Ser Pro Ser His Met Thr Asn Val Asp His
465                 470                 475                 480

His Ser Ser Thr Ser Asp Asp Ser Val Thr Val Cys Gly Asn Val Val
                485                 490                 495

Ser Tyr Gly Gly Tyr Gln Gly Phe Ala Ile Pro Val Gly Thr Ser Val
            500                 505                 510

Asn Tyr Asp Pro Phe Thr Ala Ala Glu Ile Ala Tyr Asn Ala Arg Asn
        515                 520                 525

His Tyr Tyr Tyr Ala Gln His Gln Gln Gln Gln Ile Gln Gln Ser
    530                 535                 540

Pro Gly Gly Asp Phe Pro Val Ala Ile Ser Asn Asn His Ser Ser Asn
545                 550                 555                 560

Met Tyr Phe His Gly Glu Gly Gly Glu Gly Ala Pro Thr Phe Ser
                565                 570                 575

Val Trp Asn Asp Thr
            580

<210> SEQ ID NO 31
<211> LENGTH: 584
<212> TYPE: PRT
<213> ORGANISM: Arabidopsis thaliana

<400> SEQUENCE: 31

Met Asn Ser Met Asn Asn Trp Leu Gly Phe Ser Leu Ser Pro His Asp

-continued

```
1               5                   10                  15
Gln Asn His His Arg Thr Asp Val Asp Ser Ser Thr Thr Arg Thr Ala
                20                  25                  30
Val Asp Val Ala Gly Gly Tyr Cys Phe Asp Leu Ala Ala Pro Ser Asp
                35                  40                  45
Glu Ser Ser Ala Val Gln Thr Ser Phe Leu Ser Pro Phe Gly Val Thr
                50                  55                  60
Leu Glu Ala Phe Thr Arg Asp Asn Asn Ser His Ser Arg Asp Trp Asp
65                  70                  75                  80
Ile Asn Gly Gly Ala Cys Asn Thr Leu Thr Asn Asn Glu Gln Asn Gly
                    85                  90                  95
Pro Lys Leu Glu Asn Phe Leu Gly Arg Thr Thr Thr Ile Tyr Asn Thr
                100                 105                 110
Asn Glu Thr Val Val Asp Gly Asn Gly Asp Cys Gly Gly Gly Asp Gly
                115                 120                 125
Gly Gly Gly Gly Ser Leu Gly Leu Ser Met Ile Lys Thr Trp Leu Ser
            130                 135                 140
Asn His Ser Val Ala Asn Ala Asn His Gln Asp Asn Gly Asn Gly Ala
145                 150                 155                 160
Arg Gly Leu Ser Leu Ser Met Asn Ser Ser Thr Ser Asp Ser Asn Asn
                    165                 170                 175
Tyr Asn Asn Asn Asp Asp Val Val Gln Glu Lys Thr Ile Val Asp Val
                180                 185                 190
Val Glu Thr Thr Pro Lys Lys Thr Ile Glu Ser Phe Gly Gln Arg Thr
                195                 200                 205
Ser Ile Tyr Arg Gly Val Thr Arg His Arg Trp Thr Gly Arg Tyr Glu
210                 215                 220
Ala His Leu Trp Asp Asn Ser Cys Lys Arg Glu Gly Gln Thr Arg Lys
225                 230                 235                 240
Gly Arg Gln Val Tyr Leu Gly Gly Tyr Asp Lys Glu Glu Lys Ala Ala
                245                 250                 255
Arg Ala Tyr Asp Leu Ala Ala Leu Lys Tyr Trp Gly Pro Thr Thr Thr
                260                 265                 270
Thr Asn Phe Pro Leu Ser Glu Tyr Glu Lys Glu Val Glu Glu Met Lys
            275                 280                 285
His Met Thr Arg Gln Glu Tyr Val Ala Ser Leu Arg Arg Lys Ser Ser
            290                 295                 300
Gly Phe Ser Arg Gly Ala Ser Ile Tyr Arg Gly Val Thr Arg His His
305                 310                 315                 320
Gln His Gly Arg Trp Gln Ala Arg Ile Gly Arg Val Ala Gly Asn Lys
                325                 330                 335
Asp Leu Tyr Leu Gly Thr Phe Gly Thr Gln Glu Glu Ala Ala Glu Ala
                340                 345                 350
Tyr Asp Ile Ala Ala Ile Lys Phe Arg Gly Leu Ser Ala Val Thr Asn
                355                 360                 365
Phe Asp Met Asn Arg Tyr Asn Val Lys Ala Ile Leu Glu Ser Pro Ser
            370                 375                 380
Leu Pro Ile Gly Ser Ser Ala Lys Arg Leu Lys Asp Val Asn Asn Pro
385                 390                 395                 400
Val Pro Ala Met Met Ile Ser Asn Asn Val Ser Glu Ser Ala Asn Asn
                405                 410                 415
Val Ser Gly Trp Gln Asn Thr Ala Phe Gln His His Gln Gly Met Asp
            420                 425                 430
```

Leu Ser Leu Leu Gln Gln Gln Glu Arg Tyr Val Gly Tyr Tyr Asn
        435                 440                 445

Gly Gly Asn Leu Ser Thr Glu Ser Thr Arg Val Cys Phe Lys Gln Glu
        450                 455                 460

Glu Glu Gln Gln His Phe Leu Arg Asn Ser Pro Ser His Met Thr Asn
465                 470                 475                 480

Val Asp His His Ser Ser Thr Ser Asp Asp Ser Val Thr Val Cys Gly
                    485                 490                 495

Asn Val Val Ser Tyr Gly Gly Tyr Gln Gly Phe Ala Ile Pro Val Gly
                500                 505                 510

Thr Ser Val Asn Tyr Asp Pro Phe Thr Ala Ala Glu Ile Ala Tyr Asn
            515                 520                 525

Ala Arg Asn His Tyr Tyr Tyr Ala Gln His Gln Gln Gln Gln Gln Ile
        530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Glu Gly Ala Pro
                565                 570                 575

Thr Phe Ser Val Trp Asn Asp Thr
            580

<210> SEQ ID NO 32
<211> LENGTH: 579
<212> TYPE: PRT
<213> ORGANISM: Brassica napus

<400> SEQUENCE: 32

Met Asn Asn Asn Trp Leu Gly Phe Ser Leu Ser Pro Tyr Glu Gln Asn
1               5                   10                  15

His His Arg Lys Asp Val Tyr Ser Ser Thr Thr Thr Val Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Val Asp
    50                  55                  60

Ala Phe Thr Arg Asp Asn Asn Ser His Ser Arg Asp Trp Asp Ile Asn
65              70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Gly Asp Gly
        115                 120                 125

Gly Gly Gly Ser Leu Gly Leu Ser Met Ile Lys Thr Trp Leu Arg Asn
    130                 135                 140

Gln Pro Val Asp Asn Val Asp Asn Gln Glu Asn Gly Asn Ala Ala Lys
145                 150                 155                 160

Gly Leu Ser Leu Ser Met Asn Ser Ser Thr Ser Cys Asp Asn Asn
                165                 170                 175

Asp Ser Asn Asn Asn Val Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu

```
                210                 215                 220
Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
            245                 250                 255

Arg Ala Tyr Asp Leu Ala Ala Leu Lys Tyr Trp Gly Thr Thr Thr Thr
                260                 265                 270

Thr Asn Phe Pro Met Ser Glu Tyr Glu Lys Val Glu Glu Met Lys
            275                 280                 285

His Met Thr Arg Gln Glu Tyr Val Ala Ser Leu Arg Arg Lys Ser Ser
290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
        355                 360                 365

Phe Asp Met Asn Arg Tyr Asn Val Lys Ala Ile Leu Glu Ser Pro Ser
370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Ser Ala Ser Gly Trp Gln Asn Ala Ala Val Gln His His Gln Gly Val
            420                 425                 430

Asp Leu Ser Leu Leu His Gln His Gln Glu Arg Tyr Asn Gly Tyr Tyr
        435                 440                 445

Tyr Asn Gly Gly Asn Leu Ser Ser Glu Ser Ala Arg Ala Cys Phe Lys
450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Ser Val Thr Val
                485                 490                 495

Cys Gly Asn Val Val Gly Tyr Gly Gly Tyr Gln Gly Phe Ala Ala Pro
            500                 505                 510

Val Asn Cys Asp Ala Tyr Ala Ala Ser Glu Phe Asp Tyr Asn Ala Arg
        515                 520                 525

Asn His Tyr Tyr Phe Ala Gln Gln Gln Thr Gln Ser Pro Gly
530                 535                 540

Gly Asp Phe Pro Ala Ala Met Thr Asn Asn Val Gly Ser Asn Met Tyr
545                 550                 555                 560

Tyr His Gly Glu Gly Gly Glu Val Ala Pro Thr Phe Thr Val Trp
            565                 570                 575

Asn Asp Asn

<210> SEQ ID NO 33
<211> LENGTH: 579
<212> TYPE: PRT
<213> ORGANISM: Brassica napus

<400> SEQUENCE: 33

Met Asn Asn Asn Trp Leu Gly Phe Ser Leu Ser Pro Tyr Glu Gln Asn
```

```
  1               5                   10                  15
His His Arg Lys Asp Val Cys Ser Ser Thr Thr Thr Ala Val Asp
            20                  25                  30

Val Ala Gly Glu Tyr Cys Tyr Asp Pro Thr Ala Ser Asp Glu Ser
            35                  40                  45

Ser Ala Ile Gln Thr Ser Phe Pro Ser Pro Phe Gly Val Val Leu Asp
 50                      55                  60

Ala Phe Thr Arg Asp Asn Asn Ser His Ser Arg Asp Trp Asp Ile Asn
 65                  70                  75                  80

Gly Ser Ala Cys Asn Asn Ile His Asn Asp Glu Gln Asp Gly Pro Lys
                 85                  90                  95

Leu Glu Asn Phe Leu Gly Arg Thr Thr Thr Ile Tyr Asn Thr Asn Glu
             100                 105                 110

Asn Val Gly Asp Ile Asp Gly Ser Gly Cys Tyr Gly Gly Gly Asp Gly
             115                 120                 125

Gly Gly Gly Ser Leu Gly Leu Ser Met Ile Lys Thr Trp Leu Arg Asn
         130                 135                 140

Gln Pro Val Asp Asn Val Asp Asn Gln Glu Asn Gly Asn Gly Ala Lys
145                 150                 155                 160

Gly Leu Ser Leu Ser Met Asn Ser Ser Thr Ser Cys Asp Asn Asn Asn
                 165                 170                 175

Tyr Ser Asn Asn Leu Val Ala Gln Gly Lys Thr Ile Asp Asp Ser
             180                 185                 190

Val Glu Ala Thr Pro Lys Lys Thr Ile Glu Ser Phe Gly Gln Arg Thr
             195                 200                 205

Ser Ile Tyr Arg Gly Val Thr Arg His Arg Trp Thr Gly Arg Tyr Glu
     210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                 245                 250                 255

Arg Ala Tyr Asp Leu Ala Ala Leu Lys Tyr Trp Gly Thr Thr Thr Thr
             260                 265                 270

Thr Asn Phe Pro Met Ser Glu Tyr Glu Lys Glu Ile Glu Glu Met Lys
     275                 280                 285

His Met Thr Arg Gln Glu Tyr Val Ala Ser Leu Arg Arg Lys Ser Ser
     290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                 325                 330                 335

Asp Leu Tyr Leu Gly Thr Phe Gly Thr Gln Glu Glu Ala Ala Glu Ala
             340                 345                 350

Tyr Asp Ile Ala Ala Ile Lys Phe Arg Gly Leu Thr Ala Val Thr Asn
             355                 360                 365

Phe Asp Met Asn Arg Tyr Asn Val Lys Ala Ile Leu Glu Ser Pro Ser
     370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Val Ser Glu Ser Glu Asn
                 405                 410                 415

Asn Ala Ser Gly Trp Gln Asn Ala Ala Val Gln His His Gln Gly Val
             420                 425                 430
```

-continued

```
Asp Leu Ser Leu Leu Gln Gln His Gln Glu Arg Tyr Asn Gly Tyr Tyr
        435                 440                 445

Tyr Asn Gly Gly Asn Leu Ser Ser Glu Ser Ala Arg Ala Cys Phe Lys
    450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Asp Ser Val Thr Val
                485                 490                 495

Cys Gly Asn Val Val Gly Tyr Gly Tyr Gln Gly Phe Ala Ala Pro
            500                 505                 510

Val Asn Cys Asp Ala Tyr Ala Ser Glu Phe Asp Tyr Asn Ala Arg
            515                 520                 525

Asn His Tyr Tyr Phe Ala Gln Gln Gln Thr Gln His Ser Pro Gly
        530                 535                 540

Gly Asp Phe Pro Ala Ala Met Thr Asn Asn Val Gly Ser Asn Met Tyr
545                 550                 555                 560

Tyr His Gly Glu Gly Gly Glu Val Ala Pro Thr Phe Thr Val Trp
                565                 570                 575

Asn Asp Asn

<210> SEQ ID NO 34
<211> LENGTH: 565
<212> TYPE: PRT
<213> ORGANISM: Arabidopsis thaliana

<400> SEQUENCE: 34

Met Asn Ser Asn Asn Trp Leu Ala Phe Pro Leu Ser Pro Thr His Ser
1               5                   10                  15

Ser Leu Pro Pro His Ile His Ser Ser Gln Asn Ser His Phe Asn Leu
                20                  25                  30

Gly Leu Val Asn Asp Asn Ile Asp Asn Pro Phe Gln Asn Gln Gly Trp
            35                  40                  45

Asn Met Ile Asn Pro His Gly Gly Gly Glu Gly Gly Glu Val Pro
    50                  55                  60

Lys Val Ala Asp Phe Leu Gly Val Ser Lys Ser Gly Asp His His Thr
65                  70                  75                  80

Asp His Asn Leu Val Pro Tyr Asn Asp Ile His Gln Thr Asn Ala Ser
                85                  90                  95

Asp Tyr Tyr Phe Gln Thr Asn Ser Leu Leu Pro Thr Val Val Thr Cys
            100                 105                 110

Ala Ser Asn Ala Pro Asn Asn Tyr Glu Leu Gln Glu Ser Ala His Asn
        115                 120                 125

Leu Gln Ser Leu Thr Leu Ser Met Gly Ser Thr Gly Ala Ala Ala Ala
    130                 135                 140

Glu Val Ala Thr Val Lys Ala Ser Pro Ala Glu Thr Ser Ala Asp Asn
145                 150                 155                 160

Ser Ser Ser Thr Thr Asn Thr Ser Gly Gly Ala Ile Val Glu Ala Thr
                165                 170                 175

Pro Arg Arg Thr Leu Glu Thr Phe Gly Gln Arg Thr Ser Ile Tyr Arg
            180                 185                 190

Gly Val Thr Arg His Arg Trp Thr Gly Arg Tyr Glu Ala His Leu Trp
        195                 200                 205

Asp Asn Ser Cys Arg Arg Glu Gly Gln Ser Arg Lys Gly Arg Gln Gly
    210                 215                 220
```

-continued

```
Gly Tyr Asp Lys Glu Glu Lys Ala Ala Arg Ala Tyr Asp Leu Ala Ala
225                 230                 235                 240

Leu Lys Tyr Trp Gly Pro Ser Thr Thr Thr Asn Phe Pro Ile Thr Asn
            245                 250                 255

Tyr Glu Lys Glu Val Glu Glu Met Lys Asn Met Thr Arg Gln Glu Phe
        260                 265                 270

Val Ala Ser Ile Arg Arg Lys Ser Ser Gly Phe Ser Arg Gly Ala Ser
    275                 280                 285

Met Tyr Arg Gly Val Thr Arg His His Gln His Gly Arg Trp Gln Ala
290                 295                 300

Arg Ile Gly Arg Val Ala Gly Asn Lys Asp Leu Tyr Leu Gly Thr Phe
305                 310                 315                 320

Ser Thr Glu Glu Glu Ala Ala Glu Ala Tyr Asp Ile Ala Ala Ile Lys
                325                 330                 335

Phe Arg Gly Leu Asn Ala Val Thr Asn Phe Glu Ile Asn Arg Tyr Asp
            340                 345                 350

Val Lys Ala Ile Leu Glu Ser Asn Thr Leu Pro Ile Gly Gly Gly Ala
        355                 360                 365

Ala Lys Arg Leu Lys Glu Ala Gln Ala Leu Glu Ser Ser Arg Lys Arg
    370                 375                 380

Glu Glu Met Ile Ala Leu Gly Ser Asn Phe His Gln Tyr Gly Ala Ala
385                 390                 395                 400

Ser Gly Ser Ser Ser Val Ala Ser Ser Ser Arg Leu Gln Leu Gln Pro
                405                 410                 415

Tyr Pro Leu Ser Ile Gln Gln Pro Phe Glu His Leu His His Gln
            420                 425                 430

Pro Leu Leu Thr Leu Gln Asn Asn Asn Asp Ile Ser Gln Tyr His Asp
        435                 440                 445

Ser Phe Ser Tyr Ile Gln Thr Gln Leu His Leu His Gln Gln Gln Thr
    450                 455                 460

Asn Asn Tyr Leu Gln Ser Ser Ser His Thr Ser Gln Leu Tyr Asn Ala
465                 470                 475                 480

Tyr Leu Gln Ser Asn Pro Gly Leu Leu His Gly Phe Val Ser Asp Asn
                485                 490                 495

Asn Asn Thr Ser Gly Phe Leu Gly Asn Asn Gly Ile Gly Ile Gly Ser
            500                 505                 510

Ser Ser Thr Val Gly Ser Ser Ala Glu Glu Glu Phe Pro Ala Val Lys
        515                 520                 525

Val Asp Tyr Asp Met Pro Pro Ser Gly Gly Ala Thr Gly Tyr Gly Gly
    530                 535                 540

Trp Asn Ser Gly Glu Ser Ala Gln Gly Ser Asn Pro Gly Gly Val Phe
545                 550                 555                 560

Thr Met Trp Asn Glu
                565

<210> SEQ ID NO 35
<211> LENGTH: 540
<212> TYPE: PRT
<213> ORGANISM: Arabidopsis thaliana

<400> SEQUENCE: 35

Met Asp Asn Pro Phe Gln Thr Gln Glu Trp Asn Met Ile Asn Pro His
1               5                   10                  15

Gly Gly Gly Gly Asp Glu Gly Gly Glu Val Pro Lys Val Ala Asp Phe
```

```
                20                  25                  30
Leu Gly Val Ser Lys Pro Asp Glu Asn Gln Ser Asn His Leu Val Ala
            35                  40                  45
Tyr Asn Asp Ser Asp Tyr Tyr Phe His Thr Asn Ser Leu Met Pro Ser
        50                  55                  60
Val Gln Ser Asn Asp Val Val Ala Ala Cys Asp Ser Asn Thr Pro
65                  70                  75                  80
Asn Asn Ser Ser Tyr His Glu Leu Gln Glu Ser Ala His Asn Leu Gln
                85                  90                  95
Ser Leu Thr Leu Ser Met Gly Thr Thr Ala Gly Asn Asn Val Val Asp
            100                 105                 110
Lys Ala Ser Pro Ser Glu Thr Thr Gly Asp Asn Ala Ser Gly Gly Ala
            115                 120                 125
Leu Ala Val Val Glu Thr Ala Thr Pro Arg Arg Ala Leu Asp Thr Phe
            130                 135                 140
Gly Gln Arg Thr Ser Ile Tyr Arg Gly Val Thr Arg His Arg Trp Thr
145                 150                 155                 160
Gly Arg Tyr Glu Ala His Leu Trp Asp Asn Ser Cys Arg Arg Glu Gly
                165                 170                 175
Gln Ser Arg Lys Gly Arg Gln Gly Gly Tyr Asp Lys Glu Asp Lys Ala
            180                 185                 190
Ala Arg Ser Tyr Asp Leu Ala Ala Leu Lys Tyr Trp Gly Pro Ser Thr
            195                 200                 205
Thr Thr Asn Phe Pro Ile Thr Asn Tyr Glu Lys Glu Val Glu Glu Met
        210                 215                 220
Lys His Met Thr Arg Gln Glu Phe Val Ala Ala Ile Arg Arg Lys Ser
225                 230                 235                 240
Ser Gly Phe Ser Arg Gly Ala Ser Met Tyr Arg Gly Val Thr Arg His
                245                 250                 255
His Gln His Gly Arg Trp Gln Ala Arg Ile Gly Arg Val Ala Gly Asn
            260                 265                 270
Lys Asp Leu Tyr Leu Gly Thr Phe Ser Thr Glu Glu Ala Ala Glu
        275                 280                 285
Ala Tyr Asp Ile Ala Ala Ile Lys Phe Arg Gly Leu Asn Ala Val Thr
        290                 295                 300
Asn Phe Glu Ile Asn Arg Tyr Asp Val Lys Ala Ile Leu Glu Ser Ser
305                 310                 315                 320
Thr Leu Pro Ile Gly Gly Gly Ala Ala Lys Arg Leu Lys Glu Ala Gln
                325                 330                 335
Ala Leu Glu Ser Ser Arg Lys Arg Glu Ala Glu Met Ile Ala Leu Gly
            340                 345                 350
Ser Ser Phe Gln Tyr Gly Gly Ser Ser Thr Gly Ser Gly Ser Thr
            355                 360                 365
Ser Ser Arg Leu Gln Leu Gln Pro Tyr Pro Leu Ser Ile Gln Gln Pro
        370                 375                 380
Leu Glu Pro Phe Leu Ser Leu Gln Asn Asn Asp Ile Ser His Tyr Asn
385                 390                 395                 400
Asn Asn Asn Ala His Asp Ser Ser Phe Asn His His Ser Tyr Ile
                405                 410                 415
Gln Thr Gln Leu His Leu His Gln Gln Thr Asn Asn Tyr Leu Gln Gln
            420                 425                 430
Gln Ser Ser Gln Asn Ser Gln Gln Leu Tyr Asn Ala Tyr Leu His Ser
            435                 440                 445
```

```
Asn Pro Ala Leu Leu His Gly Leu Val Ser Thr Ser Ile Val Asp Asn
    450                 455                 460

Asn Asn Asn Gly Gly Ser Ser Gly Ser Tyr Asn Thr Ala Ala Phe
465             470                 475                 480

Leu Gly Asn His Gly Ile Gly Ile Gly Ser Ser Thr Val Gly Ser
                485                 490                 495

Thr Glu Glu Phe Pro Thr Val Lys Thr Asp Tyr Asp Met Pro Ser Ser
            500                 505                 510

Asp Gly Thr Gly Gly Tyr Ser Gly Trp Thr Ser Glu Ser Val Gln Gly
        515                 520                 525

Ser Asn Pro Gly Gly Val Phe Thr Met Trp Asn Glu
    530                 535                 540

<210> SEQ ID NO 36
<211> LENGTH: 516
<212> TYPE: PRT
<213> ORGANISM: Arabidopsis thaliana

<400> SEQUENCE: 36

Met Ile Asn Pro His Gly Gly Gly Glu Gly Gly Glu Val Pro Lys
1               5                   10                  15

Val Ala Asp Phe Leu Gly Val Ser Lys Ser Gly Asp His His Thr Asp
            20                  25                  30

His Asn Leu Val Pro Tyr Asn Asp Ile His Gln Thr Asn Ala Ser Asp
        35                  40                  45

Tyr Tyr Phe Gln Thr Asn Ser Leu Leu Pro Thr Val Val Thr Cys Ala
    50                  55                  60

Ser Asn Ala Pro Asn Asn Tyr Glu Leu Gln Glu Ser Ala His Asn Leu
65              70                  75                  80

Gln Ser Leu Thr Leu Ser Met Gly Ser Thr Gly Ala Ala Ala Glu
            85                  90                  95

Val Ala Thr Val Lys Ala Ser Pro Ala Glu Thr Ser Ala Asp Asn Ser
            100                 105                 110

Ser Ser Thr Thr Asn Thr Ser Gly Gly Ala Ile Val Glu Ala Thr Pro
        115                 120                 125

Arg Arg Thr Leu Glu Thr Phe Gly Gln Arg Thr Ser Ile Tyr Arg Gly
    130                 135                 140

Val Thr Arg His Arg Trp Thr Gly Arg Tyr Glu Ala His Leu Trp Asp
145                 150                 155                 160

Asn Ser Cys Arg Arg Glu Gly Gln Ser Arg Lys Gly Arg Gln Gly Gly
                165                 170                 175

Tyr Asp Lys Glu Glu Lys Ala Ala Arg Ala Tyr Asp Leu Ala Ala Leu
            180                 185                 190

Lys Tyr Trp Gly Pro Ser Thr Thr Thr Asn Phe Pro Ile Thr Asn Tyr
        195                 200                 205

Glu Lys Glu Val Glu Glu Met Lys Asn Met Thr Arg Gln Glu Phe Val
    210                 215                 220

Ala Ser Ile Arg Arg Lys Ser Ser Gly Phe Ser Arg Gly Ala Ser Met
225                 230                 235                 240

Tyr Arg Gly Val Thr Arg His His Gln His Gly Arg Trp Gln Ala Arg
                245                 250                 255

Ile Gly Arg Val Ala Gly Asn Lys Asp Leu Tyr Leu Gly Thr Phe Ser
            260                 265                 270

Thr Glu Glu Glu Ala Ala Glu Ala Tyr Asp Ile Ala Ala Ile Lys Phe
```

```
                275                 280                 285
Arg Gly Leu Asn Ala Val Thr Asn Phe Glu Ile Asn Arg Tyr Asp Val
    290                 295                 300
Lys Ala Ile Leu Glu Ser Asn Thr Leu Pro Ile Gly Gly Ala Ala
305                 310                 315                 320
Lys Arg Leu Lys Glu Ala Gln Ala Leu Glu Ser Arg Lys Arg Glu
                325                 330                 335
Glu Met Ile Ala Leu Gly Ser Asn Phe His Gln Tyr Gly Ala Ala Ser
            340                 345                 350
Gly Ser Ser Ser Val Ala Ser Ser Arg Leu Gln Leu Gln Pro Tyr
                355                 360                 365
Pro Leu Ser Ile Gln Gln Pro Phe Glu His Leu His His Gln Pro
370                 375                 380
Leu Leu Thr Leu Gln Asn Asn Asn Asp Ile Ser Gln Tyr His Asp Ser
385                 390                 395                 400
Phe Ser Tyr Ile Gln Thr Gln Leu His Leu His Gln Gln Thr Asn
                405                 410                 415
Asn Tyr Leu Gln Ser Ser Ser His Thr Ser Gln Leu Tyr Asn Ala Tyr
                420                 425                 430
Leu Gln Ser Asn Pro Gly Leu Leu His Gly Phe Val Ser Asp Asn Asn
            435                 440                 445
Asn Thr Ser Gly Phe Leu Gly Asn Asn Gly Ile Gly Ile Gly Ser Ser
            450                 455                 460
Ser Thr Val Gly Ser Ser Ala Glu Glu Glu Phe Pro Ala Val Lys Val
465                 470                 475                 480
Asp Tyr Asp Met Pro Pro Ser Gly Gly Ala Thr Gly Tyr Gly Trp
                485                 490                 495
Asn Ser Gly Glu Ser Ala Gln Gly Ser Asn Pro Gly Gly Val Phe Thr
                500                 505                 510
Met Trp Asn Glu
        515

<210> SEQ ID NO 37
<211> LENGTH: 65
<212> TYPE: PRT
<213> ORGANISM: Artificial sequence
<220> FEATURE:
<223> OTHER INFORMATION: Consensus sequence of Figure 1
<220> FEATURE:
<221> NAME/KEY: MISC_FEATURE
<222> LOCATION: (0)..(0)
<223> OTHER INFORMATION: Synthesized

<400> SEQUENCE: 37

Met Ser Asn Asn Trp Leu Gly Phe Ser Leu Ser Pro Asp Gln Ser Ser
1               5                   10                  15
Ala Val Asp Ala Phe Ile Gly Ser Val Asp Phe Asn Ser His Arg Asp
                20                  25                  30
Asn Ala Asn Ile Asn Ser Gly Pro Glu Asn Phe Ser Ile Gly Gly Gly
            35                  40                  45
Gly Gly Ile Gly Leu Ser Met Ile Lys Thr Trp Leu Arg Asn Gln Pro
        50                  55                  60
Asn
65

<210> SEQ ID NO 38
<211> LENGTH: 62
```

```
<212> TYPE: PRT
<213> ORGANISM: Artificial sequence
<220> FEATURE:
<223> OTHER INFORMATION: APETALA2 PFAM consensus sequence
<220> FEATURE:
<221> NAME/KEY: MISC_FEATURE
<222> LOCATION: (0)..(0)
<223> OTHER INFORMATION: Synthesized

<400> SEQUENCE: 38

Ser Lys Tyr Arg Gly Val Arg Gln Arg Pro Trp Gly Lys Trp Val Ala
1               5                   10                  15

Glu Ile Arg Asp Pro Arg Lys Gly Thr Arg Val Trp Leu Gly Thr Phe
            20                  25                  30

Asp Thr Ala Glu Glu Ala Ala Arg Ala Tyr Asp Val Ala Ala Leu Lys
        35                  40                  45

Leu Arg Gly Pro Ser Ala Val Leu Asn Phe Pro Asn Glu Leu
        50                  55                  60
```

That which is claimed:

1. A method for producing haploid plant embryos comprising expressing in a pollen cell, an OVULE DEVELOPMENT PROTEIN 2 (ODP2) polypeptide comprising an amino acid sequence selected from the group consisting of:
   (a) the amino acid sequence of SEQ ID NO: 26; and
   (b) an amino acid sequence having at least 85% sequence identity to SEQ ID NO: 26, or 28, wherein said polypeptide comprises two APETALA2 (AP2) domains and has ODP2 activity rendering pollen cells embryogenic; and,
thereby inducing embryogenesis in the pollen cells;
culturing the pollen cells to produce haploid plant embryos; and
selecting a haploid plant embryo.

2. The method of claim 1, wherein said pollen cell is a microspore.

3. The method of claim 1, further comprising providing to the pollen cell a Wuschel polypeptide.

4. The method of claim 2, wherein said ODP2 nucleotide sequence is under the control of a tissue specific promoter that is active in a microspore or a promoter that is active during microspore development.

5. The method of claim 4, wherein said promoter is selected from the group consisting of: NTM19 promoter, BCP1 promoter, PG47 promoter, ZmG13 promoter, and BNM1 promoter.

6. The method of claim 1, wherein said ODP2 nucleotide sequence is under the control of a chemically inducible promoter.

7. The method of claim 1, further comprising generating a haploid plant from a haploid plant embryo.

8. The method of claim 1, further comprising exposing the haploid embryo to a doubling agent.

9. The method of claim 8, wherein said doubling agent is colchicine.

10. The method of any of claim 1-3 or 4-9, wherein said haploid plant embryo is a maize haploid plant embryo and said pollen cell is a maize haploid pollen cell.

11. A method of promoting embryogenesis in a microspore or anther culture, wherein said method comprises introducing into a plant or a plant cell an OVULE DEVELOPMENT PROTEIN 2 (ODP2) nucleotide sequence that encodes an ODP2 polypeptide comprising an amino acid sequence selected from the group consisting of:
   (a) the amino acid sequence of SEQ ID NO: 26; and
   (b) an amino acid sequence having at least 85% sequence identity to SEQ ID NO: 26, wherein said polypeptide comprises two APETALA2 (AP2) domains and has ODP2 activity rendering the microspore or anther cultures embryogenic; and, thereby inducing embryogenesis in the microspore or anther cultures; and selecting an embryogenic microspore or embryogenic anther culture.

12. The method of claim 11, wherein said ODP2 nucleotide sequence is under the control of a tissue specific promoter that is active in a microspore.

13. The method of claim 11, wherein said ODP2 nucleotide sequence is under the control of a promoter that is active during microspore development.

14. The method of claim 13, wherein said promoter that is active during microspore development is the maize PG47 promoter or the zm-G13 promoter.

15. The method of claim 11, wherein the ODP2 nucleotide sequence is under the control of an inducible promoter.

16. The method of claim 11, wherein the ODP2 nucleotide sequence is under the control of a promoter that is an inducible pollen-specific promoter.

* * * * *